United States Patent
Papadimitrakopoulos et al.

(10) Patent No.: US 8,193,430 B2
(45) Date of Patent: Jun. 5, 2012

(54) METHODS FOR SEPARATING CARBON NANOTUBES

(75) Inventors: Fotios Papadimitrakopoulos, West Hartford, CT (US); Sang-Yong Ju, Ithaca, NY (US)

(73) Assignee: The University of Connecticut, Farmington, CT (US)

( * ) Notice: Subject to any disclaimer, the term of this patent is extended or adjusted under 35 U.S.C. 154(b) by 681 days.

(21) Appl. No.: 12/348,631

(22) Filed: Jan. 5, 2009

(65) Prior Publication Data

US 2010/0044230 A1    Feb. 25, 2010

Related U.S. Application Data

(60) Provisional application No. 61/009,853, filed on Jan. 3, 2008.

(51) Int. Cl.
*B01D 21/26*    (2006.01)
*C02F 1/38*    (2006.01)

(52) U.S. Cl. ........ 977/845; 210/767; 210/749; 210/759; 210/787; 977/742; 977/751; 977/842

(58) Field of Classification Search .................. None
See application file for complete search history.

(56) References Cited

U.S. PATENT DOCUMENTS

| | | | |
|---|---|---|---|
| 7,131,537 | B2 | 11/2006 | Papadimitrakopoulos |
| 7,374,649 | B2 | 5/2008 | Jagota et al. |
| 2006/0045838 | A1* | 3/2006 | Malenfant et al. ......... 423/447.1 |
| 2006/0054555 | A1 | 3/2006 | Sun |
| 2008/0008643 | A1 | 1/2008 | Landi et al. |

FOREIGN PATENT DOCUMENTS

WO    2004082794 A2    9/2004

OTHER PUBLICATIONS

Guiseppi-Elie et al. Direct electron transfer of glucose oxidase on carbon nanotubes. Nanotechnology, vol. 13 (2002) 559-564.*
G.S. Duesberg, et al. "Separation of Carbon Nanotubes by Size Exclusion Chromatography" Chem. Commun. (1998) pp. 435-436.
C.S. Lin, et al. "Geometric and Electronic Structures of Carbon Nanoturbes Adsorbed with Flavin Adenine Dinucleotide: A Theoretical Study" The Journal of Physical Chemistry C (Feb. 23, 2007) pp. 4069-4073, vol. 111 (11), ACS Publications.
S-Y. Ju, et al. "Synthesis and Redox Behavior of Flavin Mononucleotide-Functionalized Single-Walled Carbon Nanotubes" Journal of the American Chemical Society (Dec. 15, 2007) pp. 655-664, vol. 130 (2), ACS Publications.
S-Y. Ju, et al. "Selection of Carbon Nanotubes with Specific Chiralities Using Helical Assemblies of Flavin Mononucleotide" Nature Nanotechnology (Jun. 2008) pp. 356-362, vol. 3, Nature Publishing Group.
J.H. Kim, et al. "Diameter-Selective Separation of Double-Walled Carbon Nanotubes" Applied Physics Letters (Dec. 3, 2008) 93, 223107-1, American Institute of Physics.

* cited by examiner

*Primary Examiner* — Krishnan S Menon
*Assistant Examiner* — Katherine Zalasky
(74) *Attorney, Agent, or Firm* — Cantor Colburn LLP

(57) ABSTRACT

Disclosed herein too is a method that includes dispersing nanotubes in media that comprises flavin moieties substituted with solubilizing side chains, and/or non-flavin containing molecular species; self-assembling the flavin moieties and other non-flavin containing molecular species in a pattern that is orderly wrapped around the nanotubes to form a composite; introducing desired amounts of an optional reagent that competes with self-assembly in order to disturb the wrapping around nanotubes with moderate order; and centrifuging the mass of the nanotubes and the composites to extract the composite from other nanotubes that are not in composite form.

55 Claims, 44 Drawing Sheets

Figure 4

METHODS FOR SEPARATING CARBON NANOTUBES

CROSS-REFERENCE TO RELATED APPLICATIONS

This reference claims priority to U.S. Provisional Application No. 61/009,853, filed on Jan. 3, 2008, the entire contents of which are hereby incorporated by reference.

BACKGROUND

This disclosure relates to methods for separating carbon nanotubes, specifically for separating single wall carbon nanotubes.

Single wall carbon nanotubes generally have a single carbon wall with outer diameters of greater than or equal to about 0.7 nanometers (nm). Single wall carbon nanotubes generally have various lengths and can have aspect ratios that are from about 5 to about 10,000. In general single wall carbon nanotubes exist in the form of rope-like-aggregates. These aggregates are commonly termed "ropes" and are formed as a result of Van der Waal's forces between the individual carbon nanotubes. The individual nanotubes in the ropes may slide against one another and rearrange themselves within the rope in order to minimize the free energy. Ropes generally have between 10 and $10^5$ nanotubes. In another embodiment, the single wall carbon nanotubes exist in the form of metallic nanotubes and semi-conducting nanotubes. Metallic nanotubes are those that display electrical characteristics similar to metals, while the semi-conducting nanotubes are those, which are electrically semi-conducting.

In general, the manner in which the graphene sheet is rolled up produces nanotubes of various helical structures. These structures as well as the lattice vectors (a1 and a2) are shown in FIG. 1. As may be seen from the FIG. 1, the integer numbers (n or m) of the lattice vectors (a1 and a2, respectively) n and m are added together and the tail and head of the resulting vector are placed on top of each other in the final nanotube structure. Zigzag nanotubes have (n,0) lattice vector values, while armchair nanotubes have (n,n) lattice vector values. Zigzag and armchair nanotubes constitute the two possible achiral confirmations, all other (m,n) lattice vector values yield chiral nanotubes. The right or left helical patterns of different (n,m) chirality carbon nanotubes are referred to as "handedness" and correspond to either (n,m) or (m,n) structures.

Carbon nanotubes can be used for a wide variety of applications such as for rendering plastics electrically conducting, in semiconductors, opto-electronic and electro-optical device applications, and the like. In each of the aforementioned applications, it is generally desirable to separate carbon nanotubes from the ropes that hold them together. In addition, it is desirable to separate carbon nanotubes according to diameter, length, chirality, handedness, electrical conductivity characteristics, and the like.

Separation of single wall carbon nanotubes based on their electrical conductivity characteristics has been conducted by amine-based selective solubilization, deoxyribonucleic acid (DNA) based anionic chromatography, dielectrophoresis, electrophoresis, selective reactivity against reactive reagents, density gradient centrifugation, and by other methods. Separation of single wall carbon nanotubes based on their lengths has been mainly accomplished by size-exclusion chromatographic techniques, capillary electrophoresis, and field-flow fractionation. Separation of single wall carbon nanotubes by diameter has been demonstrated by density gradient centrifugation as well as by DNA-based anionic chromatography. Separation of single wall carbon nanotubes based on their handedness or chirality was recently demonstrated by the interaction of a chiral bi-porphyrin moiety with single wall carbon nanotubes. As will be noted, DNA and other surfactant moieties are often used to facilitate the separation of single wall carbon nanotubes from ropes or small bundles that contain each other, i.e., the effective nanotube solubilization.

In addition, DNA affords multi-level separation of nanotubes according to type (electrical conductivity characteristics), length, diameter and chirality. Such separation is afforded only for specific DNA sequences (i.e., $d(GT)_n$ oligomers), which clearly is a major hurdle in terms of commercialization and scale-up due to the prohibitive cost of DNA. Moreover, the natural difficulty to desorb these DNA oligomers from the single wall carbon nanotubes in order to clean them and further process them adds another layer of complexity to DNA-processed single wall carbon nanotubes.

It is therefore desirable to find cheaper and more efficient methods of separating carbon nanotubes from each other.

SUMMARY

Disclosed herein too is a method comprising dispersing a plurality of (n,m)-nanotubes in media that comprises flavin moieties and/or non-flavin containing molecular species to form a mixture; the flavin moieties being substituted with solubilizing side chains; self-assembling the flavin moieties and other non-flavin containing molecular species in a pattern that is orderly wrapped around the nanotubes to form a composite; introducing an effective amount of a surfactant into the mixture to disturb the wrapping of the flavin moieties and other non-flavin containing molecular species around (8,6) nanotubes; the disturbing resulting in a partially surfactant-replaced nanotube; and centrifuging the mixture to extract the (8,6) nanotubes from the plurality of (n,m)-nanotubes.

Disclosed herein too is a method that includes dispersing nanotubes in media that comprises flavin moieties substituted with solubilizing side chains, and/or non-flavin containing molecular species; self-assembling the flavin moieties and other non-flavin containing molecular species in a pattern that is orderly wrapped around the nanotubes to form a composite; introducing desired amounts of an optional reagent that competes with self-assembly in order to disturb the wrapping around nanotubes with moderate order; and centrifuging the mass of the nanotubes and the composites to extract the composite from other nanotubes that are not in composite form.

Disclosed herein too is a composite comprising a nanotube; and flavin moieties and/or non-flavin containing molecular species that self-assemble to around the nanotube; the flavin moieties and/or non-flavin containing molecular species undergoing a charge transfer with the nanotube; the flavin moieties and/or non-flavin containing molecular species undergoing two-dimensional hydrogen bonding with each other, the hydrogen bonding facilitating the formation of the helix; the flavin moieties and/or a non-flavin containing molecular aromatic species having substituents that render the composite soluble in an aqueous solvent, an organic solvent, or a combination comprising at least an aqueous solvent and an organic solvent.

BRIEF DESCRIPTION OF FIGURES

FIG. 4 is an exemplary depiction of sequential separation of different (n,m) chirality nanotubes based on their affinity to the flavin wrapping that renders them soluble. This separation takes place by introduction of a specific reagent that depending its concentration it causes selective precipitation of different (n,m) chirality nanotubes according to the affinity of flavin wrapping for the given nanotube;

FIGS. 12(a) through 12(c) illustrate PLE maps of FMN/HiPco-SWNT dispersion centrifuged at different values of the acceleration due to gravity "g". FIGS. 12(d) and 12(e) illustrates PLE maps of SDBS-replaced SWNT of FIGS. 12(b) and 12(c), respectively;

FIG. 13(b) illustrates the corresponding background-removed and 733 nm normalized spectra;

FIG. 33(*b*) illustrates the quantum yield (QY) dependence of (6,5)-SWNT versus the solubility of FC12 in various solvents. Note that the x-axis is plotted logarithmically. The solubility of FC12 in the given solvent is proportional to ability of the solvent to disrupt H-bonding. Low FC12 solubility solvents in turn, causes the FC12 wrapped helix to be extremely tight and difficult to be disrupted (since the flavin helix is stabilized by H-bonds). As an outcome of this, the QY increases in these solvents through the displacement of oxygen-adsorbed nanotube species. On the other hand, for ethylacetate, acetone and THF, the solubility of FC12 is so high that the helix gets readily disturbed that causes profound aggregation and consequently very low QYs;

FIG. 38(*b*) shows adenine derivatives.

DETAILED DESCRIPTION

Figure 1:
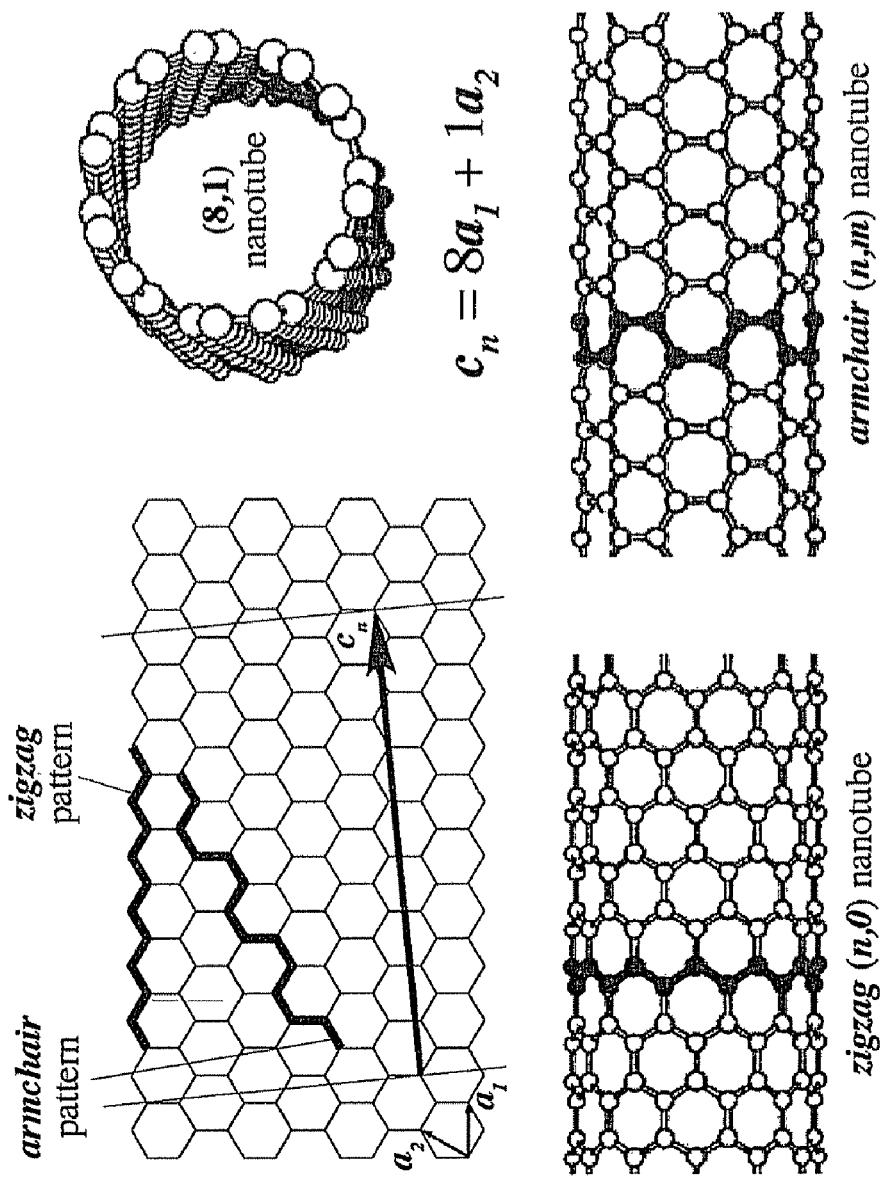
FIG. 1 shows the different chirality (n,m) nanotubes.

Disclosed herein is a method of separating nanotubes by type (metallic vs. semiconducting) diameter, chirality and handedness by using molecules that comprise flavin moieties. Small molecular weight aromatic moieties that can undergo charge transition interactions with the nanotubes and hydrogen bonding interactions with each other to form a periodic ordered array around the nanotubes can be used to separate nanotubes based on diameter, length, chirality, handedness and/or electrical conductivity characteristics. The small molecular weight aromatic moieties are flavin containing moieties (also referred to as flavin moieties) and non-flavin containing molecular aromatic species that have molecular weights of less than or equal to about 1,500 grams per mole. The small molecular weight aromatic moieties may include nucleic acids, however it is to be noted that the nucleic acids do not undergo any charge transfer interactions (e.g., $\pi$-$\pi$ interactions) with the side-walls of the nanotubes. The small molecular weight aromatic moieties form composites (also referred to as an assembly or assemblies) with the nanotubes.

Flavin moieties, such as, for example, flavin mononucleotide, flavin adenine dinucleotide (FAD), and other flavin derivatives (described in detail below) exhibit strong $\pi$-$\pi$ interaction with the side-walls of the single wall carbon nanotubes. This strong $\pi$-$\pi$ interaction with the carbon nanotube can be used to produce effective dispersion and solubilization of the carbon nanotubes that are devoid of carbonaceous impurities. The tight helical wrapping of the self-assembled helix also affords the epitaxial selection of a single (n,m) chirality nanotube along with the exclusion of physisorbed or chemisorbed impurities on the nanotube side walls. The seamless flavin helix around nanotubes provides a uniform, protecting sheath that excludes oxygen, a well-known electron acceptor, which leads to hole doping and luminescence quenching through non-radiative Auger processes. This opens an array of new frontiers in SWNT photophysics and device applications, where semiconductor purity is combined with hierarchical organization for the manipulation of nanostructured systems.

In addition to the flavin containing moieties, other small-molecular weight aromatic moieties such as, for example, non-flavin containing molecular aromatic species that can undergo charge transfer interactions with the nanotubes while simultaneously undergoing multiple hydrogen-bonding interactions with each other around the nanotube, can also be used. The small-molecular weight aromatic moieties generally have molecular weights of less than or equal to about 1,500 grams per mole. The small-molecular weight aromatic moieties generally comprise monomers, dimers, trimers, quadrimers and/or pentamers.

Unlike DNA, whose oligomeric or polymeric sugar-phosphate main chain provides the backbone for helical wrapping of the carbon nanotubes, in the case of molecules that comprise flavin moieties, such wrapping is afforded via (i) charge-transfer (between the flavin moieties and the carbon nanotubes) along the nanotube side walls and (ii) hydrogen-bonding (between adjacent flavin moieties) to propagate the helix. This renders the formation of a self-assembled structure, which can be readily dissolved away, unlike DNA.

The nanotubes can comprise carbon, boron, nitrogen, phosphorus, silicon, silicon nanotubes, germanium nanotubes, tungsten disulfide nanotubes ($WS_2$), molybdenum disulfide ($MoS_2$) nanotubes, cadmium selenide (CdSe) nanotubes, cadmium sulfide (CdS) nanotubes, cadmium telluride (CdTe) nanotubes, zinc sulfide (ZnS), palladium sulfide (PdS), palladium selenide (PdSe), and the like, and a combination comprising at least one of the foregoing nanotubes. The aforementioned nanotubes can have a single wall, double wall or multiple walls (more than two walls). The nanotubes that comprise carbon can be single wall carbon nanotubes, double wall carbon nanotubes, multiwall carbon nanotubes, boron-carbon nanotubes ($BC_3$), boron-carbon-nitrogen nanotubes ($BC_2N$), carbon-nitrogen nanotubes (CN) nanotubes, or the like, or a combination comprising at least one of the foregoing forms of carbon nanotubes.

Figure 2:
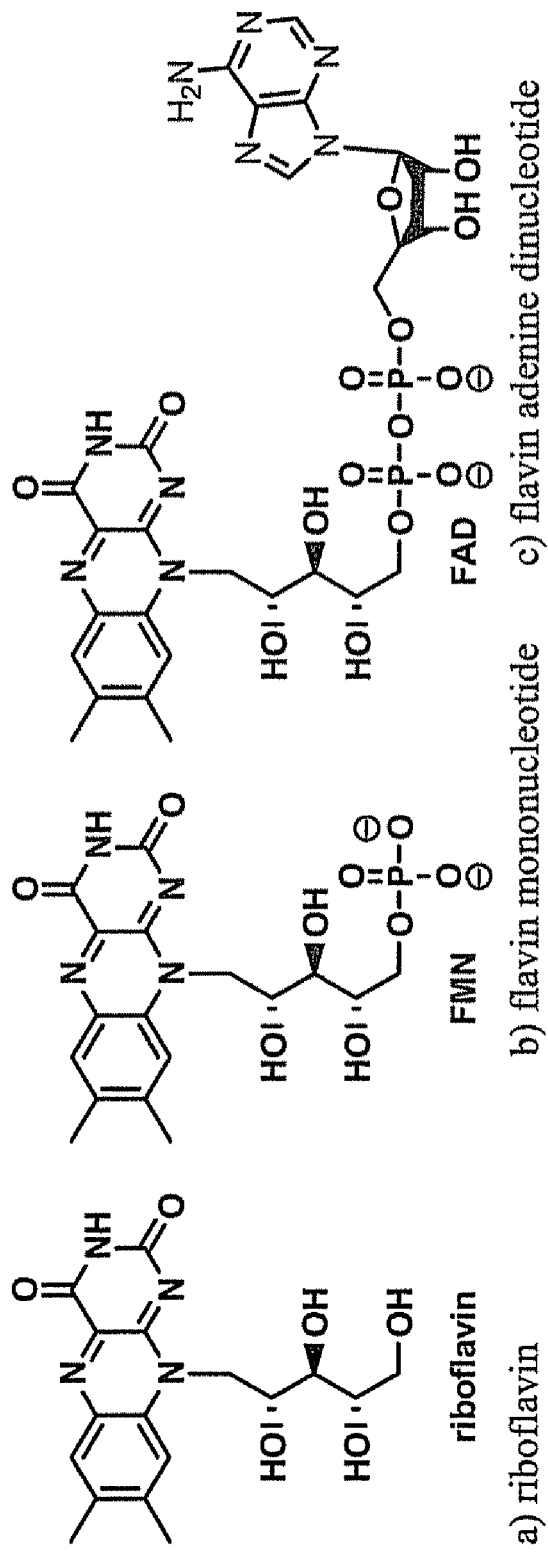
FIG. 2 shows the chemical structures of riboflavin, flavin mononucleotide (FMN) and flavin adenine dinucleotide (FAD)

In one embodiment, the flavin-containing molecule combines with the carbon nanotube to produce a flavin-moiety-carbon nanotube composite (hereinafter flavin-carbon nanotube composite). The molecules that comprise flavin moieties can comprise naturally occurring riboflavin, flavin mononucleotides (FMN) and FAD, the chemical structures of which are shown in the FIG. 2. In one embodiment, the molecules that comprise flavin moieties can be flavin derivatives. A flavin moiety with ring numbering is shown in the Formula (I) below:

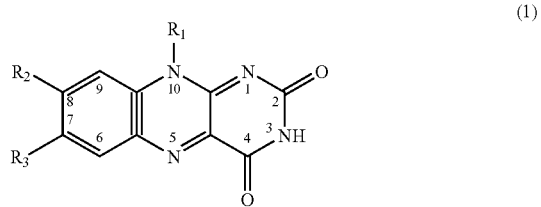

(1)

The flavin derivatives are generally obtained by reacting substitutents onto the flavin moiety at $R_1$, $R_2$ and/or $R_3$. In one embodiment, the substitutent can be a side chain that can be linear or branched and can comprise polar and/or non-polar moieties that facilitate solubility of the flavin-carbon nanotube composite in a variety of polar and non-polar solvents. As can be seen in the Formula (I), the substituents can be reacted to the flavin moiety at the 7, 8 and the 10 positions.

By changing the end groups and pendent groups on the flavin-containing molecules, the carbon nanotubes can be dispersed in various media (e.g., water, acetone, tetrahydrofuran, ethyl acetate, N,N-dimethylformamide, pyridine, and the like). Spectroscopic (UV-Vis-NIR and photoluminescence) measurements and transmission electron microscopy (TEM) results detailed below support the formation of such charge-transfer flavin-based helix on the side-walls of single wall carbon nanotubes. Circular dichroism (CD) spectroscopy indicates that flavin-containing molecules (e.g., those comprising flavin mononucleotides, hereinafter termed flavin mononucleotide-nanotube composites) can combine with carbon nanotubes in a manner that is effective to facilitate a separation of carbon nanotubes based on chirality and handedness.

When flavin mononucleotide-nanotube composite solutions are freeze-dried, the dried sample exhibits a crystalline matrix with a long-range order flavin mononucleotide crystals. In addition, the flavin-carbon nanotube composites are very sensitive to the diameter and electronic structure of the nanotubes that they organize on and as a result, afford diameter- and electrical conductivity-based enrichment avenues, respectively. Last but not least, these flavin-carbon nanotube composites are photoresponsive, an aspect that can be further used for the separation of some types of carbon nanotubes from others based upon chirality and handedness.

As noted above, the flavin derivatives are generally obtained by reacting substituents onto the flavin moiety. The flavin mononucleotide or d-ribityl alloxazine (RA) can be substituted with substituents at various positions and brought into contact with carbon nanotubes to form the flavin-carbon nanotube composite. As noted above, the flavin-containing molecule can undergo hydrogen-bonding and charge-transfer interactions with each other via the polar end groups and pendent groups as shown in the FIG. 3. The ability to form hydrogen bonding and charge-transfer interactions with each other permits the formation of extended flavin mononucleotide and d-ribityl alloxazine structures that form helical structures with tight helical wrapping of the nanotube.

In one embodiment, the flavin mononucleotide or d-ribityl alloxazine (RA) can be substituted in a variety of positions to obtain molecules that can wrap helically around the carbon nanotubes to form the flavin-carbon nanotube composite. These substituents permit the flavin-carbon nanotube composite to be suspended in organic media as well as in aqueous media. The substituent can be linear or branched alkyl chains, in which number of carbon atoms can be from about 1 to about 200, specifically about 2 to about 150 and more specifically about 3 to about 50. These alkyl substituents permit the flavin-containing molecule to be soluble in an organic solvent. In one embodiment, these alkyl substituents can be terminated with polar groups. In addition, polar groups may be added as pendent groups on to the alkyl chains. Examples of these polar groups are hydroxyl groups, amine groups, carboxylic acid groups, aldehydecarboxylic acid groups, phenylene groups, thiol groups, acrylate groups, styryl groups, norbornene groups, aminoacids side groups, and the like. In one embodiment, a branched alkyl substituent can be terminated with a hydroxyl group, an amine group, a carboxylic acid group, a phenylene group, a thiol group, or the like.

In one embodiment, the flavin derivatives comprise ethylene oxide sidechains, where number of ethylene oxide is ranging from 1 to 200. The ethylene oxide sidechain can be terminated hydroxyl, amine, carboxylic acid, phenylene, and thiol group.

In one embodiment, the substituent comprises a complex chiral center such as R- or L-ribityl, R- or L-ribityl phosphate, R- and L-ribityl diphosphatic adenine, R- or L-arabityl, R- or L-arabityl phosphate, R- and L-arabityl diphosphatic adenine, R- or L-xylityl, R- or L-xylityl phosphate, R- and L-xylityl diphosphatic adenine, R- or L-xylityl, R- or L-xylityl phosphate, R- and L-xylityl diphosphatic adenine, R- or L-lyxytyl, R- or L-lyxytyl phosphate, and R- and L-lyxytyl diphosphatic adenine.

In one embodiment, the flavin mononucleotide or d-ribityl alloxazine (RA) can be substituted in the 7, 8 or 10 positions.

The substitutions can be the same or different and are generally independent of each other. In one embodiment, the flavin mononucleotide or d-ribityl alloxazine can be substituted by alkyl moieties and olefins. Examples of alkyl moieties are methyl, ethyl, propyl, isopropyl, butyl, pentyl, hexyl, heptyl, octyl, nonyl, decyl, undecyl, dodecyl, pentadecyl, hexadecyl heptadecyl, and the like. As noted above, the alkyl moieties and olefins can be bonded to other polar species at the chain ends or in pendent positions.

In one embodiment, the substituent for the 7, 8 and 10 positions can be an organic polymer. The organic polymer can be an oligomer, a homopolymer, a copolymer, a block copolymer, an alternating block copolymer, a random polymer, a random copolymer, a random block copolymer, a graft copolymer, a star block copolymer, a dendrimer, or the like, or a combination comprising at last one of the foregoing thermoplastic polymers. The organic polymer can be an amorphous polymer or a semi-crystalline polymer that facilitates solubility of the flavin-nanotube composite in a solvent. In an exemplary embodiment, it is desirable for the substituent to comprise a crystallizable polymer. In another exemplary embodiment, it is desirable for the polymer to be a liquid crystalline polymer, specifically a lyotropic liquid crystalline polymer. In yet another exemplary embodiment, the polymers, specifically the liquid crystalline polymers can be copolymerized with a soft flexible polymeric block. The soft flexible polymeric blocks generally have a glass transition temperature that is lower than room temperature.

Examples of suitable polymers that can be used as substituents are polyolefins, polyacetals, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polyimidazopyrrolones, polypyrrolidines, polycarboranes, polyoxabicyclononanes, polydibenzofurans, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polysiloxanes, cellulose, nucleic acids, polypeptides, proteinaceous polymers, polysaccharides, chitosans, or the like, or a combination comprising at least one of the foregoing polymers.

Examples of polymers that are used in the soft blocks are elastomers such as polyethylene glycols, polydimethylsiloxanes, polybutadienes, polyisoprenes, polyolefins, nitrile rubbers, or the like, or a combination comprising at least one of the foregoing elastomers.

In an exemplary embodiment, the nitrogen atom of the isoalloxazine ring in the 10 position can be substituted by polymers that comprise nucleic acids, protein nucleic acids, peptides, (meth)acrylic acids, saccharides, chitosans, hyaluronic acids, vinyl ethers, vinyl chlorides, acrylonitriles, vinyl alcohols, styrenes, (meth)acrylates, norbornenes, copolymers of divinyl styrene and norbornadiene, pyrroles, thiophenes, anilines, phenylenes phenylene-vinylenes, phenylene-acetylenes, esters, amides, imides, carbonates, urethanes, ureas phenosl, oxadiazoles, oxazolines, thiazoles, furans, cyclopentadienes, hydroxyquinones, azides, acetylenes, benzoxazoles, benzothiazinophenothiazines, benzothiazoles, pyrazinoquinoxalines, pyromellitimides, quinoxalines, benzimidazoles, oxindoles, oxoisoindolines, dioxoisoindolines, triazines, pyridazines, piperazines, pyridines, piperidines, triazoles, pyrazoles, pyrrolidines, carboranes, oxabicyclononanes, dibenzofurans, phthalides, acetals, anhydrides, with degree of polymerization of about 1 to about 200 with degree of polymerization between 1 and 200. In one embodiment, the substitution can be conducted using hydroxyl, amine, aldehyde, carboxylic acid, ether, carbonyl, ester, acid anhydride, nitro, amide, vinyl, acetylene, diacetylene and acid halide side groups. In addition, as noted above, the polymer substituents can be reacted to end-groups comprising hydroxyl, amine, aldehyde, carboxylic acid, ether, carbonyl, ester, acid anhydride, nitro, amide, vinyl, acetylene, diacetylene, acid halides, and the like, and a combination comprising at least one of the foregoing groups. Substituents that comprise nitrogen and phosphorus can also be used.

In one embodiment, the substituent to the flavin moiety or the molecular aromatic moiety can be a nanocrystal. The nanocrystal can comprise a metal or a semiconductor. In one embodiment, the nanocrystal can comprise nanoparticles having a very narrow particle size distribution. In other words, the polydispersity index of the nanoparticles may be about 1 to about 1.5, if desired. Examples of nanoparticles are gold (e.g., $Au_{64}$) silver, cadmium selenide, cadmium telluride, zinc sulfide, silicon, silica, germanium, gallium nitride (GaN), gallium phosphoride (GaP), gallium arsenide (GaAs), and the like.

In another embodiment, the substitutent can be a low molecular weight organic moiety having a molecular weight of less than or equal to about 1,000 grams per mole. The low molecular weight organic moiety can be a crystallizable drug. The crystallizable drug can be dexamethasone, doxorubicin, methadone, morphine, and the like.

In another embodiment, the substituent can be a therapeutic and pharmaceutic biologically active agents including anti-proliferative/antimitotic agents including natural products such as vinca alkaloids (e.g., vinblastine, vincristine, and vinorelbine), paclitaxel, epipodophyllotoxins (e.g., etoposide, teniposide), antibiotics (e.g., dactinomycin, actinomycin D, daunorubicin, doxorubicin and idarubicin), anthracyclines, mitoxantrone, bleomycins, plicamycin, mithramycin and mitomycin, enzymes (L-asparaginase, which systemically metabolizes L-asparagine and deprives cells which do not have the capacity to synthesize their own asparagine), antiplatelet agents such as G(GP) IIb/IIIa inhibitors and vitronectin receptor antagonists, anti-proliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC), anti-proliferative/antimitotic antimetabolites such as folic acid analogs (e.g., methotrexate), pyrimidine analogs (e.g., fluorouracil, floxuridine, cytarabine), purine analogs and related inhibitors (e.g., mercaptopurine, thioguanine, pentostatin and 2-chlorodeoxyadenosine {cladribine}), platinum coordination complexes (e.g., cisplatin, carboplatin), procarbazine, hydroxyurea, mitotane, aminoglutethimide, hormones (e.g., estrogen), anti-coagulants (e.g., heparin, synthetic heparin salts and other inhibitors of thrombin), fibrinolytic agents (e.g., tissue plasminogen activator, streptokinase and urokinase), aspirin, dipyridamole, ticlopidine, clopidogrel, abciximab, antimigratory, antisecretory (e.g., breveldin), anti-inflammatory: such as adrenocortical steroids (e.g., cortisol, cortisone, fludrocortisone, prednisone, prednisolone, 6α-methylprednisolone, triamcinolone, betamethasone, and dexamethasone), non-steroidal agents (e.g., salicylic acid derivatives such as aspirin, para-aminophenol derivatives such as acetominophen, indole and indene acetic acids (e.g., indomethacin, sulindac, etodalac), heteroaryl acetic acids (e.g., tolmetin, diclofenac, ketorolac), arylpropionic acids (e.g., ibuprofen and derivatives), anthranilic acids (e.g., mefenamic acid, meclofenamic acid), enolic acids (e.g., piroxicam, tenoxicam, phenylbutazone, oxyphenthatrazone), nabumetone, gold compounds (e.g., auranofin, aurothioglucose, gold sodium thiomalate), immunosuppressives (e.g., cyclosporine, tacrolimus (FK-506), sirolimus (e.g., rapamycin, azathioprine, mycophenolate mofetil), angiogenic agents such as vascular endothelial growth factor (VEGF), fibroblast growth factor (FGF), angiotensin receptor blockers, nitric oxide donors, anti-sense oligionucleotides and combinations thereof, cell cycle inhibitors, mTOR inhibitors, and growth factor receptor signal transduction kinase inhibitors, retenoids, cyclin/CDK inhibitors, HMG co-enzyme reductase inhibitors (statins), protease inhibitors. The substituents can also include time-release drugs and agents.

In one embodiment, a low molecular weight organic moiety attached to the said aromatic moiety is made from a dye or a pigment, the dye or pigment being carotenoids, sexithiophenes, porphyrines, metalloporphyrines, oxazolines, quinizarines rhodamines, anthranones and their derivatives; anthraquinones and their derivatives; croconines and their derivatives; monoazos, disazos, trisazos and their derivatives; benzimidazolones and their derivatives; diketo pyrrole pyrroles and their derivatives; dioxazines and their derivatives; diarylides and their derivatives; indanthrones and their derivatives; isoindolines and their derivatives; isoindolinones and their derivatives; naphtols and their derivatives; perinones and their derivatives; perylenes and their derivatives such as perylenic acid anhydride or perylenic acid imide; ansanthrones and their derivative; dibenzpyrenequinones and their derivatives; pyranthrones and their derivatives; bioranthorones and their derivatives; isobioranthorone and their derivatives; diphenylmethane, and triphenylmethane type pigments; cyanine and azomethine type pigments; indigoid type pigments; bisbenzoimidazole type pigments; azulenium salts; pyrylium salts; thiapyrylium salts; benzopyrylium salts; phthalocyanines and their derivatives, pryanthrones and their derivatives; quinacidones and their derivatives; quinophthalones and their derivatives; squaraines and their derivatives; squarilylums and their derivatives; leuco dyes and their derivatives, deuterated leuco dyes and their derivatives; leuco-azine dyes; acridines; di- and tri-arylmethane, dyes; quinoneamines; o-nitro-substituted arylidene dyes, aryl nitrone dyes, C60, C70, and other substituted fullerenes, planar graphene moieties, or the like, or a combination comprising at least one of the foregoing dyes and pigments.

In one embodiment, the substituent is a protein, the protein being crystallizable. The protein can be an oxidoreductase, a transferace, a hydrolase, a lyase, an isomerase, a ligase, a protein, an ion channel protein and a visual protein. Examples of oxidoreductase are myogrobin, horseradish peroxidase, glucose oxidase, glucose dehydrogenase, lactate oxidase, alcohol dehydrogenase, Cytochrome P450, or the like, or a combination comprising at least one of the foregoing oxidoreductases.

In one embodiment, the substituent is a nucleic acid oligomer, where the nucleic acid oligomer binds onto a polymeric single stranded nucleic acid with complementary bases. In another embodiment, the substituent attached to the said aromatic moiety is a protein nucleic acid oligomer, where the protein nucleic acid oligomer binds onto a polymeric single stranded nucleic acid with complementary bases. In yet another embodiment, the protein nucleic acid oligomers binds onto a polymeric double stranded nucleic acid through Hoogstein base pairing. In yet another embodiment, the protein nucleic acid oligomers bind onto a polymeric single stranded protein nucleic acid with complementary bases. In yet another embodiment, the protein nucleic acid oligomers binds onto a polymeric double stranded protein nucleic acid through Hoogstein base pairing.

In another embodiment, the substituent attached to the said aromatic moiety can be a salt.

In an exemplary embodiment, the nitrogen atom of the isoalloxazine ring in the 10 position the flavin mononucleotide or d-ribityl alloxazine (RA) can be substituted by alkyl moieties and olefins. Examples of alkyl moieties are listed above. The alkyl moieties and olefins can be bonded to other polar species at the chain ends or in pendent positions. In one embodiment, the nitrogen atom of the isoalloxazine ring in the 10 position can be substituted by the polymers listed above that have a degree of polymerization of about 1 to about 200. As noted above, the substituent in the 10 position can comprise hydroxyl, amine, aldehyde, carboxylic acid, ether, carbonyl, ester, acid anhydride, nitro, amide, vinyl, acetylene, diacetylene and acid halide side groups. In an exemplary embodiment, the substituent in the fifth position for the flavin mononucleotide or d-ribityl alloxazine can comprise a hydrocarbon, nitrogen or phosphorus. The substituents can include all of the aforementioned molecules and moieties, dyes, drugs, liquid crystalline polymers, pigments, and the like.

In another exemplary embodiment, the substituent in the seventh and eighth positions for the flavin mononucleotide or d-ribityl alloxazine are independent of each other and can be the same or different. Examples of substituents for the seventh and the eighth position are those that comprise ethyl, propyl, isopropyl, butyl, chloride, bromide, fluoride, iodide, nitrile, hydroxyl, methyl ester, alkene, alkyne, amine, amide, nitro, thiol, and thioether.

In one embodiment other molecular aromatic species can be used instead of the flavin nucleotide or d-ribityl alloxazine. The molecular aromatic species therefore do not contain a flavin nucleotide (flavin moiety) or d-ribityl alloxazine. It is desirable for the molecular aromatic species to be capable of undergoing π-π interactions with the carbon nanotube as well as undergoing hydrogen bonding interactions with one another so as to form a helical configuration around the nanotube as shown in the FIG. 2 for the flavin mononucleotide. In one embodiment, these non-flavin containing molecular species are hydrogen-bonding prone agents that stabilize self-assembly of the flavin moieties on the nanotubes. The hydrogen-bonding prone agents are sugars, monosaccharides, D-glucose, L-glucose, D-galactose, L-galactose, D-mannose, L-mannose, disaccharides, sucrose, lactose, maltose, trehalose, cellobiose, oligosaccharides, and a combination comprising at least one of the foregoing non-flavin containing low molecular weight species.

Examples of such molecular aromatic species are 1-dodecyl-1H-pyrrolo[3,2-c]pyridine-4,6-diamine, 1-dodecyl-1H-benzo[h]quinazoline-2,4-dione, 2-amino-5-dodecyl-3,5-dihydro-pyrrolo[3,2-d]pyrimidin-4-one, 3-amino-5-dodecyl-5H-benzo[b][1,6]naphthyridin-1-one, 3-amino-5-dodecyl-5H-2,5-diaza-naphthacen-1-one, 3-amino-9-dodecyl-2,9-dihydro-2,4,9-triaza-fluoren-1-one, 3-amino-11-dodecyl-2,11-dihydro-2,4,11-triaza-benzo[b]fluoren-1-one, 3-amino-13-dodecyl-2,13-dihydro-2,4,13-triaza-indeno[1,2-b]

anthracen-1-one, 3,7-diamino-9,10-didodecyl-2,6-diaza-anthracene-1,5-dione, 3,10-diamino-5,12-didodecyl-5,12-dihydro-2,5,7,9,12,14-hexaaza-pentacene-1,8-dione, 4-dodecyl-4H-benzo[f]quinazoline-1,3-dione, 5-dodecyl-5H-pyrido[4,3-b]indole-1,3-diamine, 5-dodecyl-5H-benzo[f]pyrido[4,3-b]indole-1,3-diamine, 5,10-dodecyl-pyrimido[4,5-g]quinazoline-2,4,7,9-tetraone, 7-amino-1-dodecyl-1H-[1,6]naphthyridin-5-one, 7-octyl-7H-pyrrolo[2,3-d]pyrimidin-4-ylamine, 7,14-didodecyl-7,14-dihydro-1,3,5,7,8,10,12,14-octaaza-pentacene-2,4,9,11-tetraone, 8-dodecyl-8H-pteridine-2,4-dione, 9-dodecyl-9H-1,3,9-triaza-fluoren-4-ylamine, 8,9-dimethyl-12-dodecyl-12H-1,3,5,12-tetraaza-naphthacene-2,4-dione, 1'-dodecyl-9H-1,3,11-triaza-benzo[b]fluoren-4-ylamine, 12-dodecyl-12H-1,3,5,12-tetraaza-naphthacene and 14-dodecyl-4H-1,3,5,12-tetraaza-pentacene-2,4-dione.

The aforementioned molecular aromatic species can be substituted in a variety of positions with substituents that can facilitate solubility of the molecular species-nanotube composite in a variety of solvents. For example, the 1-dodecyl-1H-pyrrolo[3,2-c]pyridine-4,6-diamine can be substituted in the 1 position with linear or branched alkyl chains having about 1 to about 200 repeat units. Examples of the alkyl chains are given above. The substitution in the 1 position can also be conducted with oligomers having about 1 to about 200 repeat units. Lists of the repeat units used for the oligomers are provided above. As noted above, the substitution can be conducted using hydroxyl, amine, aldehyde, carboxylic acid, ether, carbonyl, ester, acid anhydride, nitro, amide, vinyl, acetylene, diacetylene and acid halide side groups. In a similar manner, the 1-dodecyl-1H-benzo[h]quinazoline-2,4-dione, can be substituted in the 1, 7, 8 and/or the 9 positions; the 2-amino-5-dodecyl-3,5-dihydro-pyrrolo[3,2-d]pyrimidin-4-one can be substituted in the 5, 6 and/or the 7 positions; the 3-amino-5-dodecyl-5H-benzo[b][1,6]naphthyridin-1-one can be substituted in the 5, 7, 8 and/or the 10 positions; the 3-amino-5-dodecyl-5H-2,5-diaza-naphthacen-1-one can be substituted in the 5, 8, 9 and/or the 12 positions; the 3-amino-9-dodecyl-2,9-dihydro-2,4,9-triaza-fluoren-1-one can be substituted in the 6, 7 and/or the 9 positions; the 3-amino-11-dodecyl-2,11-dihydro-2,4,11-triaza-benzo[b]fluoren-1-one can be substituted in the 7, 8 and/or in the 11 position; the 3-amino-13-dodecyl-2,13-dihydro-2,4,13-triaza-indeno[1,2-b]anthracen-1-one can be substituted in the 8, 9 and/or in the 13 position; the 3,7-diamino-9,10-didodecyl-2,6-diaza-anthracene-1,5-dione can be substituted in the 9 and/or in the 10 position; the 3,10-diamino-5,12-didodecyl-5,12-dihydro-2,5,7,9,12,14-hexaaza-pentacene-1,8-dione can be substituted in the 5 and/or in the 12 position; the 4-dodecyl-4H-benzo[f]quinazoline-1,3-dione can be substituted in the 4, 7, 8 and/or 9 positions; the 5-dodecyl-5H-pyrido[4,3-b]indole-1,3-diamine can be substituted in the 5, 7 and/or 8 positions; the 5-dodecyl-5H-benzo[f]pyrido[4,3-b]indole-1,3-diamine can be substituted in the 5, 8 and/or 9 positions; the 5,10-dodecyl-pyrimido[4,5-g]quinazoline-2,4,7,9-tetraone can be substituted in the 5 and/or 10 positions; the 7-amino-1-dodecyl-1H-[1,6]naphthyridin-5-one is substituted in the 1, 2, 3 and/or 4 positions; the 7-octyl-7H-pyrrolo[2,3-d]pyrimidin-4-ylamine can be substituted in the 4, 5 and/or the 7 positions; the 7,14-didodecyl-7,14-dihydro-1,3,5,7,8,10,12,14-octaaza-pentacene-2,4,9,11-tetraone can be substituted in the 1, 7, 8 and/or the 14 positions; the 8-dodecyl-8H-pteridine-2,4-dione can be substituted in the 5, 6, 7 and/or 8 positions; the 9-dodecyl-9H-1,3,9-triaza-fluoren-4-ylamine can be substituted in the 6, 7 and/or 9 positions; the 8,9-dimethyl-12-dodecyl-12H-1,3,5,12-tetraaza-naphthacene-2,4-dione can be substituted in the 5, 8 and 9 positions; the 11-dodecyl-9H-1,3,11-triaza-benzo[b]fluoren-4-ylamine can be substituted in the 7, 8 and 11 positions; the 12-dodecyl-12H-1,3,5,12-tetraaza-naphthacene can be substituted in the 12 position; and the 14-dodecyl-4H-1,3,5,12-tetraaza-pentacene-2,4-dione can be substituted in the 14 position.

In one embodiment, the molecular aromatic species that form the helix can comprise isoalloxazine or alloxazine moieties that are reacted to 1H-benzo[h]quinazoline-2,4-dione, 3,5-dihydro-pyrrolo[3,2-d]pyrimidin-4-one, 5H-benzo[b][1,6]naphthyridin-1-one, 5H-2,5-diaza-naphthacen-1-one, 2,9-dihydro-2,4,9-triaza-fluoren-1-one, 2,11-dihydro-2,4,11-triaza-benzo[b]fluoren-1-one, 2,13-dihydro-2,4,13-triaza-indeno[1,2-b]anthracen-1-one, 2,6-diaza-anthracene-1,5-dione, 5,12-dihydro-2,5,7,9,12,14-hexaaza-pentacene-1,8-dione, 4H-benzo[f]quinazoline-1,3-dione, 5H-pyrido[4,3-b]indole-1,3-diamine, 5H-benzo[f]pyrido[4,3-b]indole-1,3-diamine, pyrimido[4,5-g]quinazoline-2,4,7,9-tetraone, 1H-[1,6]naphthyridin-5-one, 7H-pyrrolo[2,3-d]pyrimidin-4-ylamine, 7,14-dihydro-1,3,5,7,8,10,12,14-octaaza-pentacene-2,4,9,11-tetraone, 8H-pteridine-2,4-dione, 9H-1,3,9-triaza-fluoren-4-ylamine, 12H-1,3,5,12-tetraaza-naphthacene-2,4-dione, 9H-1,3,11-triaza-benzo[b]fluoren-4-ylamine, 12H-1,3,5,12-tetraaza-naphthacene or 4H-1,3,5,12-tetraaza-pentacene-2,4-dione.

In an exemplary embodiment, the molecular aromatic species that form the helix can comprise isoalloxazine or alloxazine moieties that are reacted to 1H-pyrrolo[3,2-c]pyridine-4,6-diamine, 5H-pyrido[4,3-b]indole-1,3-diamine, 5H-benzo[f]pyrido[4,3-b]indole-1,3-diamine, 8H-pteridine-2,4-dione, 7-octyl-7H-pyrrolo[2,3-d]pyrimidin-4-ylamine, 9H-1,3,9-triaza-fluoren-4-ylamine, 9H-1,3,11-triaza-benzo[b]fluoren-4-ylamine, or 13H-1,3,13-triaza-indeno[1,2-b]anthracen-4-ylamine.

In one embodiment, two or more different kinds of the molecular aromatic species can co-organize in a sequential fashion through π-π interactions or hydrogen interactions with the nanotube to take a helical configuration that enables a molecular wrapping of the nanotube. The helical configuration forms a periodic lattice structure that prevents the adsorption of other species on the nanotubes. The helical configuration also permits for the formation of long-range order between the composites themselves or between the composites and other nanotubes. The co-organization also occurs because of hydrogen interactions between the different molecular aromatic species that form the helix. In one embodiment, it is to be noted that the two or more of the aforementioned molecular aromatic species can alternate with each other to form the helix that wraps tightly around the nanotube.

For example, any two of the following molecular aromatic species from amongst 1-dodecyl-1H-pyrrolo[3,2-c]pyridine-4,6-diamine, 1-dodecyl-1H-benzo[h]quinazoline-2,4-dione, 2-amino-5-dodecyl-3,5-dihydro-pyrrolo[3,2-d]pyrimidin-4-one, 3-amino-5-dodecyl-5H-benzo[b][1,6]naphthyridin-1-one, 3-amino-5-dodecyl-5H-2,5-diaza-naphthacen-1-one, 3-amino-9-dodecyl-2,9-dihydro-2,4,9-triaza-fluoren-1-one, 3-amino-11-dodecyl-2,1,1-dihydro-2,4,1,1-triaza-benzo[b]fluoren-1-one, 3-amino-13-dodecyl-2,13-dihydro-2,4,13-triaza-indeno[1,2-b]anthracen-1-one, 3,7-diamino-9,10-didodecyl-2,6-diaza-anthracene-1,5-dione, 3,10-diamino-5,12-didodecyl-5,12-dihydro-2,5,7,9,12,14-hexaaza-pentacene-1,8-dione, 4-dodecyl-4H-benzo[f]quinazoline-1,3-dione, 5-dodecyl-5H-pyrido[4,3-b]indole-1,3-diamine, 5-dodecyl-5H-benzo[f]pyrido[4,3-b]indole-1,3-diamine, 5,10-dodecyl-pyrimido[4,5-g]quinazoline-2,4,7,9-tetraone, 7-amino-1-dodecyl-1H-[1,6]naphthyridin-5-one, 7-octyl-7H-pyrrolo[2,3-d]pyrimidin-4-ylamine, 7,14-didodecyl-7, 14-dihydro-1,3,5,7,8,10,12,14-octaaza-pentacene-2,4,9,11-tetraone, 8-dodecyl-8H-pteridine-2,4-dione, 9-dodecyl-9H-1,3,9-triaza-fluoren-4-ylamine, 8,9-dimethyl-12-dodecyl-12H-1,3,5,12-tetraaza-naphthacene-2,4-dione, 11-dodecyl-9H-1,3,11-triaza-benzo[b]fluoren-4-ylamine, 12-dodecyl-12H-1,3,5,12-tetraaza-naphthacene and 14-dodecyl-4H-1,3,5,12-tetraaza-pentacene-2,4-dione can interact with one another via hydrogen interactions to form a helix around a nanotube. It is to be noted that substituted versions (derivatives) of the aforementioned molecular aromatic species can also be used to form the helix.

The aforementioned non-flavin containing molecular aromatic species have the following ring structures and ring positions, some of which can be substituted as will be indicated below:

a) 1-dodecyl-1H-pyrrolo[3,2-c]pyridine-4,6-diamine in Formula (2),

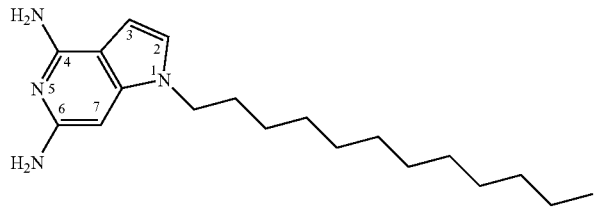

(2)

b) 1-dodecyl-1H-benzo[h]quinazoline-2,4-dione in Formula (3),

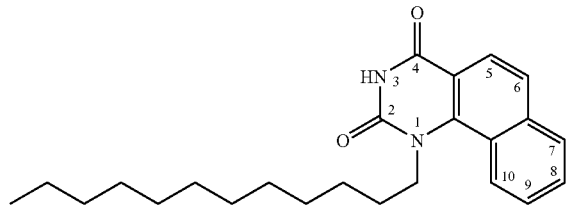

(3)

c) 2-amino-5-dodecyl-3,5-dihydro-pyrrolo[3,2-d]pyrimidin-4-one in Formula (4),

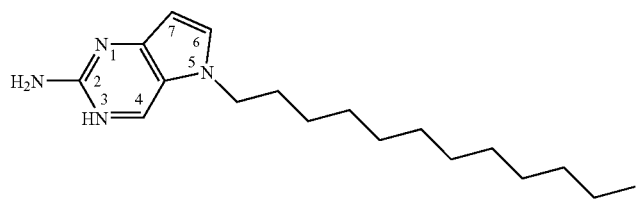

(4)

d) 3-amino-5-dodecyl-5H-benzo[b][1,6]naphthyridim-1-one in Formula (5),

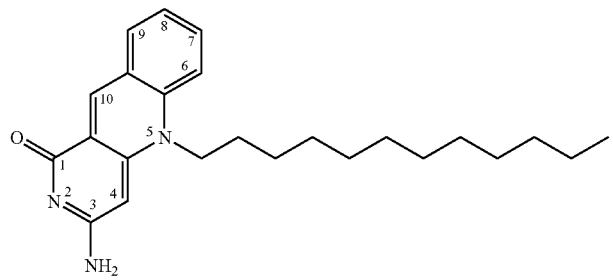

(5)

e) 3-amino-5-dodecyl-5H-2,5-diaza-naphthacen-1-one in Formula (6),

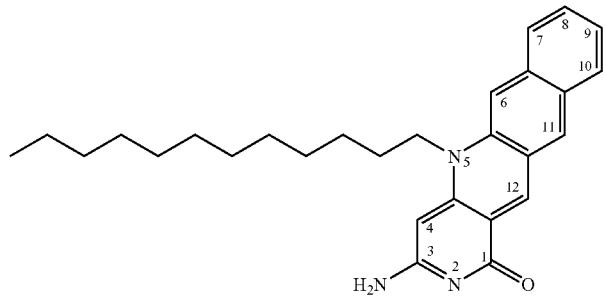

(6)

f) 3-amino-9-dodecyl-2,9-dihydro-2,4,9-triaza-fluoren-1-one in Formula (7),
(7)
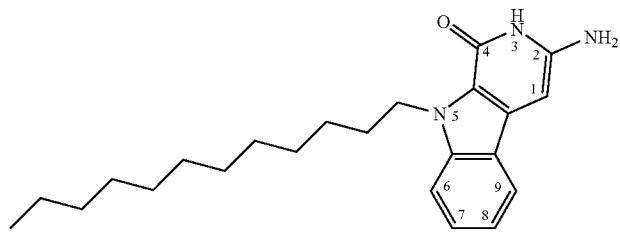
g) 3-amino-11-dodecyl-2,11-dihydro-2,4,11-triaza-benzo[b]fluoren-1-one in Formula (8)
(8)
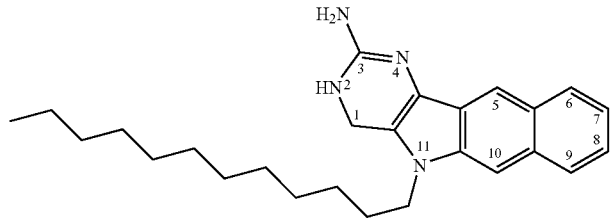
h) 3-amino-13-dodecyl-2,13-dihydro-2,4,13-triaza-indeno[1,2-b]anthracen-1-one in Formula (9),
(9)
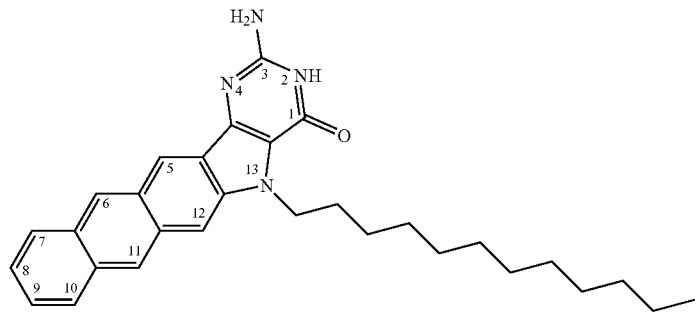
i) 3,7-diamino-9,10-dididecyl-2,6-diaza-anthracene-1,5-dione in Formula (10),
(10)
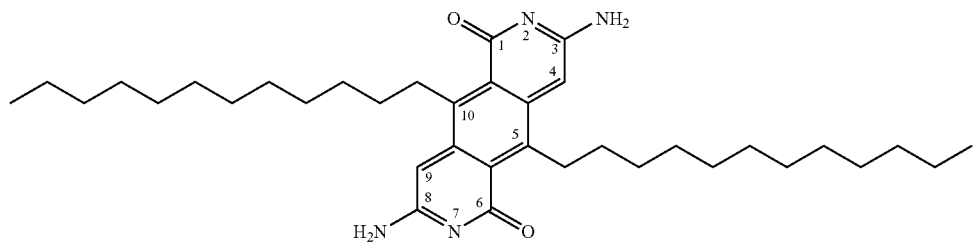
j) 3,10-diamino-5,12-didodecyl-5,12-dihydro-2,5,7,9,12,14-hexaaza-pentacene-1,8dione, in Formula (11)
(11)
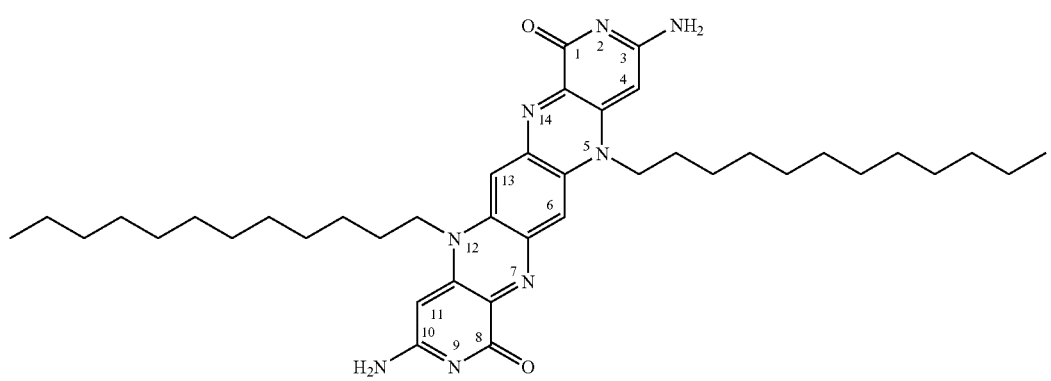

k) 4-dodecyl-4H-benzo[f]quinazoline-1,3-dione in Formula (12),
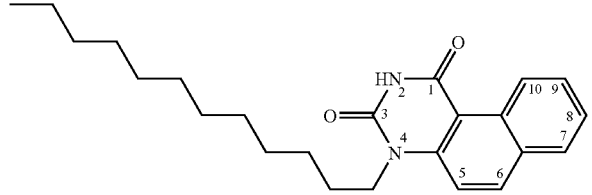
(12)
l) 5-dodecyl-5H-pyrido[4,3-b]indole-1,3-diamine in Formula (13),
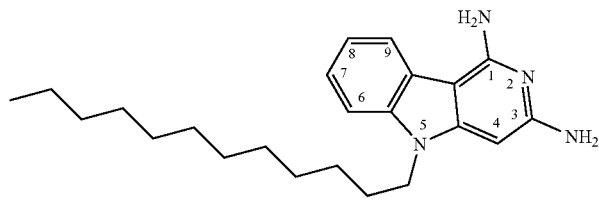
(13)
m) 5-dodecyl-5H-benzo[f]pyrido[4,3-b]indole-1,3-diamine in Formula (14)
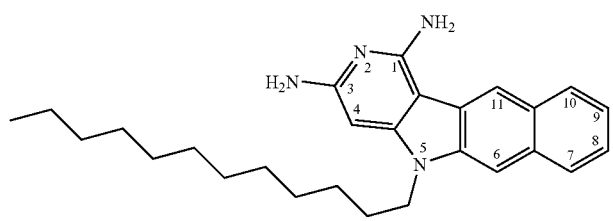
(14)
n) 5,10-didodecyl-pyrimido[4,5-g]quinazoline-2,4,7,9-tetraone in Formula (15)
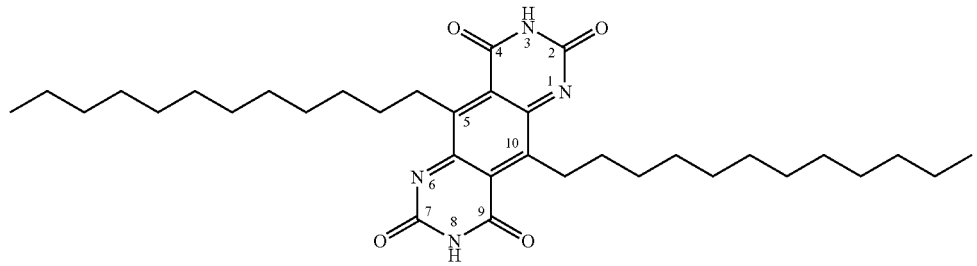
(15)
o) 7-amino-1-dodecyl-1H-[1,6]naphthyridin-5-one in Formula (2),
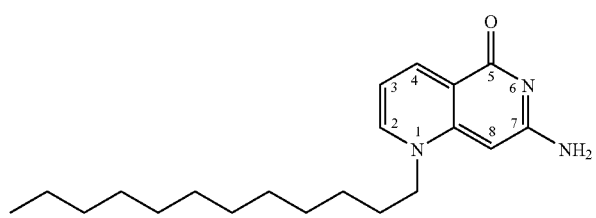
(16)
p) 7-octyl-7H-pyrrolo[2,3-d]pyrimidin-4-ylamine in Formula (17),
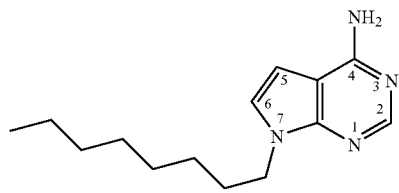
(17)

-continued
q) 7,14-didodecyl-7,14-dihydro-1,3,5,7,8,10,12,14-octaaza-pentacene-2,4,9,11-tetraone in Formula (18),
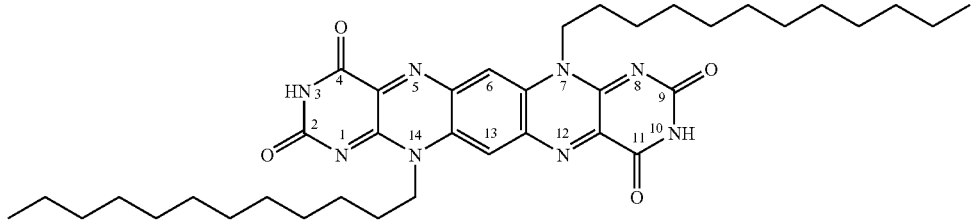
(18)
r) 8-dodecyl-8H-pteridine-2,4-dione in Formula (19),
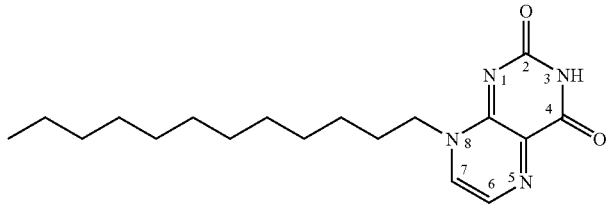
(19)
s) 9-dodecyl-9H-1,3,9-triaza-fluoren-4-ylamine in Formula (20),
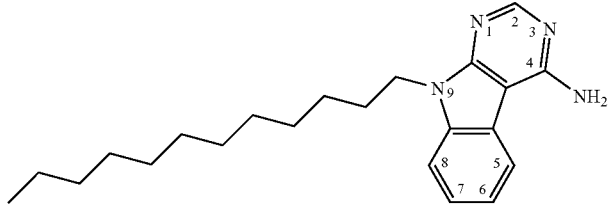
(20)
t) 8,9-dimethyl-12-dodecyl-12H-1,3,5,12-tetraaza-naphthacene-2,4-dione in Formula (21),
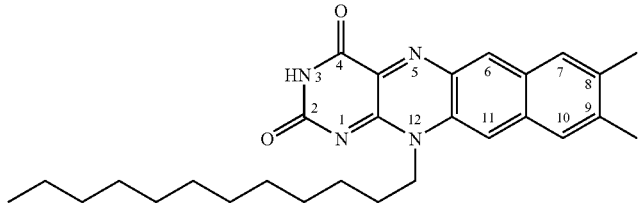
(21)
u) 11-dodecyl-9H-1,3,11-triaza-benzo[b]fluoren-4-ylamine in Formula (22),
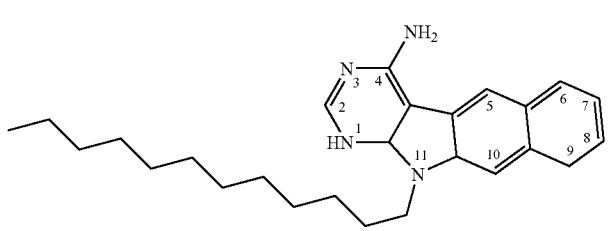
(22)
v) 12-dodecyl-12H-1,3,5,12-tetraaza-naphthacene in Formula (23)
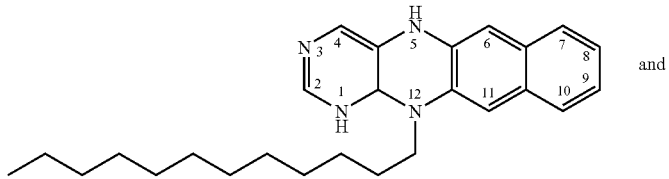
and
(23)

w) 14-dodecyl-4H-1,3,5,12-tetraaza-pentacene-2,4-dione in Formula (24)

(24)

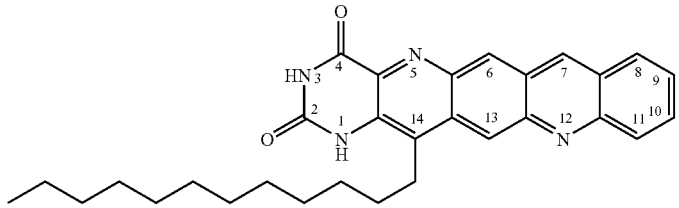

In an exemplary embodiment, one molecular aromatic species from amongst 2-amino-5-dodecyl-3,5-dihydro-pyrrolo[3,2-d]pyrimidin-4-one, 3-amino-9-dodecyl-2,9-dihydro-2,4,9-triaza-fluoren-1-one, 3-amino-11-dodecyl-2,11-dihydro-2,4,11-triaza-benzo[b]fluoren-1-one, or 3-amino-13-dodecyl-2,13-dihydro-2,4,13-triaza-indeno[1,2-b]anthracen-1-one, and their respective derivatives and the other molecular aromatic species from amongst 7-amino-1-dodecyl-1H-[1,6]naphthyridin-5-one, 3-amino-5-dodecyl-5H-benzo[b][1,6]naphthyridin-1-one, 3-amino-5-dodecyl-5H-2,5-diaza-naphthacen-1-one, or 3-amino-5-dodecyl-5H-2,5-diaza-pentacen-1-one, and their respective derivatives can interact to form a helix around a carbon nanotube.

In yet another embodiment, one of the aromatic species that form the helix can be a flavin mononucleotide or d-ribityl alloxazine, while the other can be selected from amongst 1-dodecyl-1H-pyrrolo[3,2-c]pyridine-4,6-diamine, 1-dodecyl-1H-benzo[h]quinazoline-2,4-dione, 2-amino-5-dodecyl-3,5-dihydro-pyrrolo[3,2-d]pyrimidin-4-one, 3-amino-5-dodecyl-5H-benzo[b][1,6]naphthyridin-1-one, 3-amino-5-dodecyl-5H-2,5-diaza-naphthacen-1-one, 3-amino-9-dodecyl-2,9-dihydro-2,4,9-triaza-fluoren-1-one, 3-amino-11-dodecyl-2,1-dihydro-2,4,1,1-triaza-benzo[b]fluoren-1-one, 3-amino-13-dodecyl-2,13-dihydro-2,4,13-triaza-indeno[1,2-b]anthracen-1-one, 3,7-diamino-9,10-didodecyl-2,6-diaza-anthracene-1,5-dione, 3,10-diamino-5,12-didodecyl-5,12-dihydro-2,5,7,9,12,14-hexaaza-pentacene-1,8-dione, 4-dodecyl-4H-benzo[f]quinazoline-1,3-dione, 5-dodecyl-5H-pyrrolo[4,3-b]indole-1,3-diamine, 5-dodecyl-5H-benzo[f]pyrido[4,3-b]indole-1,3-diamine, 5,10-dodecyl-pyrimido[4,5-g]quinazoline-2,4,7,9-tetraone, 7-amino-1-dodecyl-1H-[1,6]naphthyridin-5-one, 7-octyl-7H-pyrrolo[2,3-d]pyrimidin-4-ylamine, 7,14-didodecyl-7,14-dihydro-1,3,5,7,8,10,12,14-octaaza-pentacene-2,4,9,11-tetraone, 8-dodecyl-8H-pteridine-2,4-dione, 9-dodecyl-9H-1,3,9-triaza-fluoren-4-ylamine, 8,9-dimethyl-12-dodecyl-12H-1,3,5,12-tetraaza-naphthacene-2,4-dione, 11-dodecyl-9H-1,3,11-triaza-benzo[b]fluoren-4-ylamine, 12-dodecyl-12H-1,3,5,12-tetraaza-naphthacene and 14-dodecyl-4H-1,3,5,12-tetraaza-pentacene-2,4-dione, and their respective derivatives.

In another exemplary embodiment, one of the aromatic species that form the helix can be a flavin mononucleotide or d-ribityl alloxazine, while the other can be selected from amongst 1-dodecyl-1H-pyrrolo[3,2-c]pyridine-4,6-diamine, 5-dodecyl-5H-pyrido[4,3-b]indole-1,3-diamine, 5-dodecyl-5H-benzo[f]pyrido[4,3-b]indole-1,3-diamine, 8-dodecyl-8H-pteridine-2,4-dione, 7-octyl-7H-pyrrolo[2,3-d]pyrimidin-4-ylamine, 9-dodecyl-9H-1,3,9-triaza-fluoren-4-ylamine, 11-dodecyl-9H-1,3,11-triaza-benzo[b]fluoren-4-ylamine, or 13-dodecyl-13H-1,3,13-triaza-indeno[1,2-b]anthracen-4-ylamine and their respective derivatives.

In one embodiment, in one method of manufacturing the flavin-containing-nanotube composite or the non-flavin containing molecular aromatic species-nanotube composite, the flavin moiety or the molecular aromatic species are first blended in an appropriate solvent with the nanotubes to form a mixture. The solvents used for the blending can vary depending upon the substituents contained by the flavin moieties, the d-ribityl alloxazine moieties and/or the non-flavin containing molecular aromatic species.

The solvents can be liquid aprotic polar solvents, polar protic solvents, non-polar solvents or a combination comprising at least one of the foregoing solvents. Liquid aprotic polar solvents such as water, propylene carbonate, ethylene carbonate, butyrolactone, acetonitrile, benzonitrile, nitromethane, nitrobenzene, sulfolane, dimethylformamide, N-methylpyrrolidone, or the like, or a combination comprising at least one of the foregoing solvents are generally desirable. Polar protic solvents such as, but not limited to, water, methanol, acetonitrile, nitromethane, ethanol, propanol, isopropanol, butanol, or the like, or a combination comprising at least one of the foregoing polar protic solvents may be used. Other non-polar solvents such a benzene, toluene, ortho-xylene, meta-xylene, para-xylene, chlorobenzene, methylene chloride, chloroform, carbon tetrachloride, hexane, diethyl ether, tetrahydrofuran, or the like, or a combination comprising at least one of the foregoing solvents may also be used. Exemplary solvents include water, alcohols such as methanol, ethanol, and the like, acetonitrile, butyrolactone, propylene carbonate, ethylene carbonate, ethylene glycol, diglyme, triglyme, tetraglyme, nitromethane, nitrobenzene, benzonitrile, methylene chloride, chloroform and other solvents, as well as high viscosity solvents like glucose, molten sugars and various oligomers, pre-polymers and polymers.

As a result of π-π interactions between the flavin-containing molecule and/or the non-flavin containing molecular aromatic species with the nanotubes and also as a result of hydrogen bonding and charge transfer interactions between the flavin-containing molecule themselves, the non-flavin containing molecular aromatic species themselves or the interactions between the flavin-containing molecule and the non-flavin containing molecular aromatic species, the flavin-containing molecules and the non-flavin containing molecular aromatic species form a tight helix around the nanotubes. The substitutents generally are disposed radially outwards from the nanotube and can facilitate solvation of the composite in an appropriate solvent.

It is to be noted that the blending can be conducted in a solution or in the melt and can be conducted in devices that use shear force, extensional force, compressive force, ultrasonic energy, electromagnetic energy, thermal energy or combinations comprising at least one of the foregoing forces or forms of energy and is conducted in processing equipment wherein the aforementioned forces are exerted by a single screw, multiple screws, intermeshing co-rotating or counter rotating screws, non-intermeshing co-rotating or counter rotating screws, reciprocating screws, screws with pins, barrels with pins, rolls, rams, helical rotors, sound energy, or combinations comprising at least one of the foregoing forces or forms of energy. Blending involving the aforementioned forces or forms of energy may be conducted in machines such as sonicators, single or multiple screw extruders, Buss kneader, Henschel, helicones, Ross mixer, Banbury, roll mills, molding machines such as injection molding machines, vacuum forming machines, blow molding machines, or then like, or combinations comprising at least one of the foregoing machines. It is to be noted that single or multiple screw extruders, Buss kneader, Henschel, helicones, Ross mixer, Banbury, roll mills, molding machines such as injection molding machines, vacuum forming machines, blow molding machine can be combined with sonicators to provide the composite.

As noted above, the composite is formed depending upon the interactions between the flavin-containing molecule and/or the non-flavin containing molecular aromatic species with the nanotubes and with each other. The interactions result in the preferential formation of composites based on the length, diameter, handedness, chirality and electrical conductivity characteristics (e.g., metallicity) of the nanotubes. As a result, the nanotubes can then be separated from each based on the length, diameter, chirality, handedness and electrical conductivity characteristics.

The separation can be conducted by processes involving centrifugation, filtration, size-exclusion based chromatography, density gradient centrifugation, anionic chromatography, silica gel columns, dielectrophoresis, to obtain a desired type and diameter separation of carbon nanotubes. In one embodiment, the dispersion and separation of nanotubes can be further processed with species having an azide group to improve metallicity-based separation of carbon nanotubes. In another embodiment, the dispersion and separation of carbon nanotube can be further processed with capillary electrophoresis, field-flow fractionation technique, and/or with DNA to improve separation based upon diameter, length, electrical conductivity and chirality of the nanotubes.

Following the separation of the nanotubes based upon diameter, length, electrical conductivity and chirality, the flavin moieties, the d-ribityl alloxazine, and/or the non-flavin containing molecular aromatic species can be removed from the nanotube surface by reducing agents, dialysis, thermal treatment and photobleaching to recover a plurality of the nanotubes. In an exemplary embodiment, the separated nanotubes are carbon nanotubes. In another embodiment, the separated nanotubes are single wall carbon nanotubes.

In another embodiment, the dispersion and separation of the nanotubes can be further accomplished with reducing agents to precipitate nanotubes, where the reducing agent is sodium dithionite, potassium dithionite, lithium aluminum hydride, sodium borohydride, hydrazine, zinc-mercury amalgam, diisobutylaluminum hydride, a Lindler catalyst, oxalic acid, sodium amalgam, ferrous ions, hydrogen, or a combination comprising at least one of the foregoing reducing agents. Without being limited to theory, these agents reduce FMN to $FMNH_2$, which lowers substantially the flavin moiety/nanotube $\pi$-$\pi$ interactions, by breaking the conjugation with the iso-alloxazine ring.

In one embodiment, the separation of the nanotubes from the composite based upon length, diameter, chirality, handedness and electrical conductivity characteristics can be conducted by first dispersing the carbon nanotubes in an aqueous media that contains flavin moieties, d-ribityl alloxazine, and/or the non-flavin containing molecular aromatic species. The dispersion is conducted in a sonicating environment to form the composite. As noted above the composite contains flavin moieties, d-ribityl alloxazine, and/or the non-flavin containing molecular aromatic species wrapped around the nanotubes. Following the formation of a composite, the mixture containing the composite and the remaining nanotubes is subjected to centrifugation to remove bundled nanotubes, carbonaceous impurities, as well as metallic impurities. The solubilized composite can then be extracted from the centrifuged mass and extracted against a variety of reagents (i.e., ethyl acetate) to remove some of the aforementioned impurities (i.e. carbonaceous substances) that remain suspended. The process of dispersion, centrifugation and/or extraction can be continued until the desired amount of composites are removed.

In one embodiment, metallic carbon nanotubes can be separated from the semiconducting carbon nanotubes by first dispersing the nanotubes and removing the bundled nanotubes and metallic impurities from the composite (where the composite comprises flavin moieties, d-ribityl alloxazine, and/or the non-flavin containing molecular aromatic species such as for example melamine derivatives, cytosine derivatives, and the like, wrapped around the nanotubes) as detailed above. The composite in the solution is then subjected to an optional centrifugation at higher centrifugation speeds, which enriches the precipitant with metallic nanotubes, leaving a supernatant enriched with semiconducting nanotubes. The forces for this centrifugation are from about 2 g (where g is the acceleration due to gravity) to about 500,000 g, specifically about 5 g to about 250,000 g, specifically about 10 g to about 200,000 g, specifically about 50 g to about 100,000 g, and more specifically about 100 g to about 50,000 g. The dispersion and precipitation of the semiconducting nanotube enriched supernatant can be repeated until the desired mass of metallic nanotubes is removed. In an exemplary embodiment, the metallic and semi-conducting carbon nanotubes are single wall carbon nanotubes.

In another embodiment, the diameter and chirality separation of the nanotubes is conducted by first dispersing the nanotubes and removing the bundled nanotubes and metallic impurities from the composite (e.g., flavin moieties, d-ribityl alloxazine, and/or the non-flavin containing molecular aromatic species wrapped around the nanotubes) as detailed above. The composite in the solution is then subjected to an optional centrifugation at higher centrifugation speeds, which enriches the precipitant with metallic nanotubes, leaving a supernatant enriched with narrower diameter nanotubes or with nanotubes having a different chirality and/or handedness. The forces for this centrifugation are from about 2 g to about 500,000 g. The dispersion, precipitation and/or extraction cycles for enriching semiconducting nanotubes in the supernatant can be repeated until the desired mass of metallic nanotubes is removed. In an exemplary embodiment, the metallic and semi-conducting carbon nanotubes are single wall carbon nanotubes.

In yet another embodiment pertaining to an optional separation of the metallic from semiconducting nanotubes, a mass of nanotubes is first blended with flavin moieties, d-ribityl alloxazine, and/or the non-flavin containing molecular aromatic species to form the composite. This blending is generally conducted in an aqueous solution. Bundled nanotubes and metallic impurities are removed from the composite. The composite is then subjected to centrifugation at speeds, which enrich the supernatant with narrower diameter nanotubes. The forces for this centrifugation are from about 2 g to about 500,000 g. The supernatant may also be enriched with semiconducting nanotubes and/or nanotubes based upon chirality.

It is to be noted that the nanotubes in the supernatant are in the composite form, i.e., they are wrapped around by the flavin moieties, d-ribityl alloxazine, and/or the non-flavin containing molecular aromatic species. The narrower diameter nanotubes, semiconducting nanotubes and nanotubes present in the supernatant based upon chirality may be precipitated. The precipitated nanotubes may be subjected to re-dispersion in aqueous media using the flavin moieties. The centrifugation steps may be conducted a plurality of times to obtain even narrower diameter nanotubes, or to obtain a richer percentage of nanotubes having a desired chirality. For example, the centrifugation may be conducted two or more times to enhance the separation of the nanotubes based upon a desired characteristic. The precipitation and re-dispersion steps may be repeated until the desired amount of diameter and chirality enrichment is achieved.

In another embodiment pertaining to the chirality separation of carbon nanotubes, carbonaceous materials are first removed from the centrifuged aqueous nanotube-composite dispersion. First, an optional enrichment of said metallic from semiconducting nanotubes may be performed. If desired, an optional enrichment of nanotubes based on diameter and/or chirality enriched may also be performed. The nanotubes that are precipitated based upon diameter and chirality are washed out with FMN and re-dispersed with d-ribityl alloxazine (RA), which enriches a different chirality semiconducting nanotube. Following this the centrifuged aqueous RA/nanotube dispersion is subjected to centrifugation at higher centrifugation speeds, which enriches the supernatant with narrower diameter and chirality semiconducting nanotubes. This permits the precipitation of narrower diameter and chirality semiconducting nanotubes. The re-dispersion in the aqueous RA solution and the subsequent precipitation using centrifugation may be continued until the desired amount of diameter and chirality enrichment are achieved.

In yet another embodiment, the carbon nanotubes may be separated based upon chirality or handedness by first removing carbonaceous materials from a centrifuged composite (e.g., aqueous FMN/nanotube) dispersion. An optional enrichment of metallic nanotubes from semiconducting nanotubes may be conducted as described above. Following this an optional enrichment of nanotubes based upon a desired diameter range and chirality may be conducted. Following this, the centrifuged FMN/nanotube dispersion may be subjected to increasing centrifugation speed which provides nanotubes having the opposite nanotube chirality.

In one embodiment, the composite may optionally be treated with a reagent that displaces the flavin moiety or the non-flavin containing molecular aromatic species from a portion of the carbon nanotube. Examples of such reagents are surfactants. The surfactants can be anionic surfactants, cationic surfactants, zwitterionic surfactants, and the like. The reagent competes with self-assembly of the flavin moieties and the non-flavin containing molecular aromatic species on the nanotube and perturbs the helical wrapping around the nanotubes. Examples of suitable surfactants that can displace flavin moieties or non-flavin containing aromatic species are sodium dodecyl sulfate (SDS), sodium dodecyl benzene sulfonate (SDBS), sodium cholate, deoxyribonucleic acid, block copolymers, and the like.

In another embodiment, the non-flavin containing molecular species comprise reagents that enhance stability of the self-assembly of the flavin moiety on the nanotubes. Examples of reagents that stabilize the flavin assembly are hydrogen-bonding prone agents; the hydrogen-bonding prone agents being sugars, monosaccharides, D-glucose, L-glucose, D-galactose, L-galactose, D-mannose, L-mannose, disaccharides, sucrose, lactose, maltose, trehalose, cellobiose, oligosaccharides, and a combination comprising at least one of the foregoing reagents.

In yet another embodiment, (8,6) carbon nanotubes may be separated from nanotubes by first optionally removing carbonaceous materials from said centrifuged composite (e.g., aqueous FMN/nanotube) dispersion. Following this, an optional centrifugation of the centrifuged aqueous FMN/nanotube dispersion at higher centrifugation speeds may be conducted, which enriches the precipitant with metallic nanotubes, leaving a supernatant enriched with semiconducting nanotubes. A selective replacement of the FMN/nanotube using the desired amount of second surfactant such as SDBS may be conducted. The FMN is displaced by the SDBS. A partially SDBS-replaced nanotube is then precipitated with the desired amount of salt (e.g., NaCl). Following this, an optional heat treatment of said (8,6) enriched SWNT is conducted to destabilize and precipitate SDBS-wrapped nanotube. In one embodiment, an optional pH change of the (8,6) enriched SWNT may be conducted to destabilize and precipitate SDBS-wrapped nanotube. In another embodiment, an optional light treatment of the (8,6) enriched SWNT may be conducted to destabilize and precipitate FMN-wrapped (8,6) SWNT. In yet another embodiment, an optional hydrogen peroxide treatment of said (8,6) enriched SWNT may be conducted to destabilize and precipitate FMN-wrapped (8,6) SWNT. In yet another embodiment, the addition of a specific reagent that stabilizes certain helical patterns more than other can be added to increase the stability of a given chirality(ies) nanotubes. Such specific reagents can be monosaccharides, oligosaccharides, sugars, aromatic and donor-acceptor moieties with H-bonding groups, and the like. Following these processes, an optional centrifugation of said centrifuged aqueous partially SDBS-replaced FMN/nanotube dispersion at higher centrifugation speeds may be conducted which precipitates SDBS-wrapped nanotube, leaving (8,6)-enriched FMN-wrapped SWNTs behind.

Figure 4:
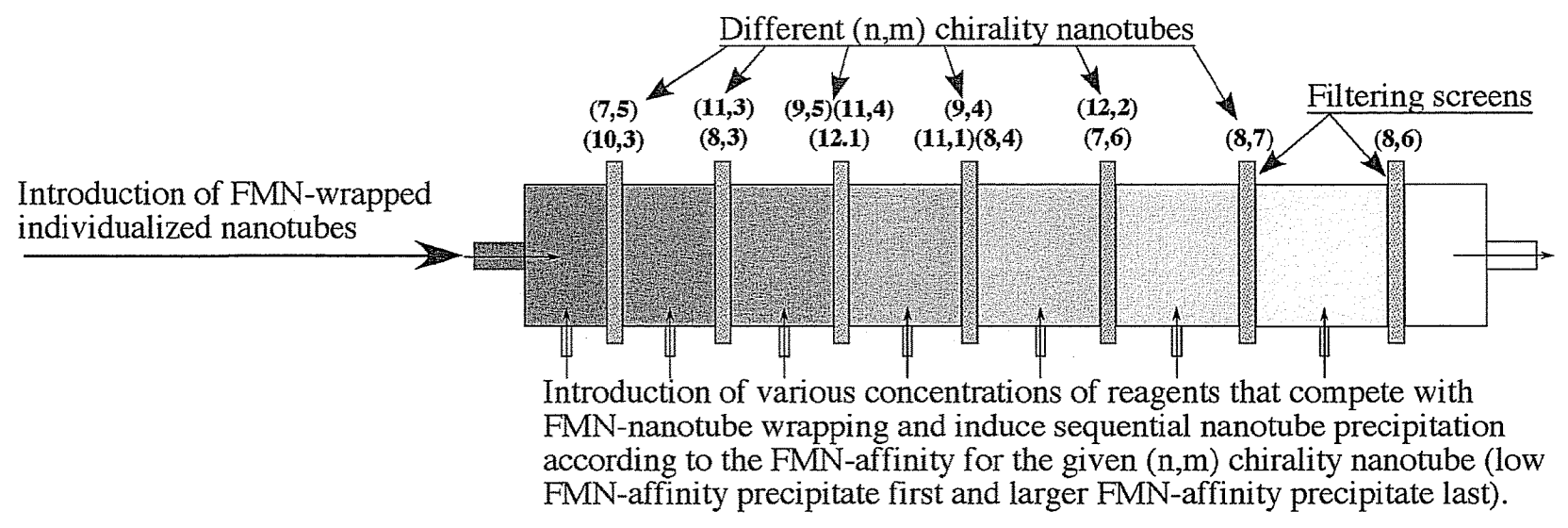

In yet another embodiment the sequential removal of various (n,m)-SWNTs according to the affinity constant (Ka) of the FMN-wrapping for each (n,m) chirality species. This utilizes the introduction of a controlled amount of a reagent that induces controlled aggregation by the nanotubes that their FMN helix have been replaced. This causes flocculation and precipitation of the reagent-exchanged nanotubes, while FMN-wrapped SWNTs (with higher Kas) remain soluble and pass to the next chamber (see FIG. 4). Precipitated groups with multiple SWNT chiralities can be further separated into their individual components using different combinations of surfactants or mixtures thereof.

The invention will now be demonstrated by the following examples, which are meant to be non-limiting.

EXAMPLES

Materials and Instrumentation

Riboflavin, riboflavin tetrabutyrate were obtained from Acros Organics. Flavin mononucleotide (FMN) and flavin adenine dinucleotide (FAD) were purchased from Sigma-Aldrich. Other flavin derivatives have been synthesized and purified as described in this disclosure or in other references that are disclosed herein. Single wall carbon nanotubes (SWNTs) having different diameter distributions were used in this study.

SWNT prepared by high pressure carbon monoxide process (HiPco) with diameter ($d_t$) distribution 1±0.35 nm) were obtained from Carbon Nanotechnologies Inc. Cobalt-molybdenum (Co—Mo) synthesized SWNTs (CoMoCAT) with diameter ($d_t$) distribution 0.8±0.2 nm) were obtained from the University of Oklahoma. SWNTs prepared by Co-substituted MCM-41 molecular sieves (Co-MCM-41) with diameter ($d_t$) distribution 0.85±0.15 nm were obtained from Yale University. SWNTs produced by water-assisted CVD process (H-SWNT) with diameter ($d_t$) distribution between 1 to 3 nm were obtained from the National Institute of Advanced Industrial Science and Technology (AIST), Japan. SWNT produced by laser-ablation (N-SWNT), with diameter ($d_t$) distribution 1.4±0.2 nm were obtained from NASA.

All reagents were purchased from Sigma-Aldrich unless otherwise mentioned. All solvents were reagent grade. Precautions were taken to avoid prolonged exposure of isoalloxazine derivatives to direct sunlight and the blue/UV part of the visible spectra by carrying the experiments in a laboratory lit with yellow fluorescent bulbs. Silica gel having particle sizes of 230 to 400 mesh were used for flash chromatography. Millipore quality deionized water with a resistivity greater than 18 mega ohms (MΩ) was used for all experiments. Fluorescence spectroscopy measurements were conducted on a Jobin-Yvon Spex Fluorolog 3-211 spectrofluorometer equipped with a PMT near-infrared (NIR) detector. Both excitation and emission light intensities were corrected against instrumental variations using Spex Fluorolog sensitivity correction factors. The UV-Vis-NIR absorption spectra were measured with a Perkin-Elmer lambda 900 UV-Vis-NIR spectrometer. Circular dichroism (CD) spectra was obtained by Pi Star (Applied Photophysics) equipped with water circulator to maintain tight control at various temperatures.

X-ray diffraction was conducted on a Xcalibur PX Ultra (Oxford Diffraction) equipped with 165 millimeter (mm) Onyx CCD. X-ray crystallography was recorded using CuKα (1.54 Å) radiation as an X-ray source. The X-ray chamber was purged with Argon during the measurement to protect the optics. Conventional transmission electron microscopy (TEM) investigations of FMN-HiPco samples were carried out on a Philip EM420 microscope operating at 100 kilovolt (kV). High-resolution TEM (HRTEM) investigations were performed on a JEOL 2010 FasTEM ultra high-resolution (UHR) microscope operating at 200 kV.

Dispersion of Flavin Derivatives with SWNT

The dispersion of flavin derivatives with SWNTs were conducted to produce the composite. A mixture of 1 mg of SWNT and 2.2×10$^{-3}$ M of flavin derivatives was added into 4 mL of either aqueous or organic media. The solution was sonicated for 4 hrs in a sonicator at 300 W intensity. In the case of water-soluble, natural flavin derivatives (i.e. riboflavin, FMN, and FAD), the resulting solution was centrifuged at 5,000-200,000 g for 2 hours and the supernatant (upper 70 to 80%) was collected. For organic solvent soluble flavin derivatives, the organic solution was centrifuged 1,500 g for 15 minutes and the upper 70 to 80% of the supernatant was collected.

Lowering the pH in $D_2O$-Dispersed FMN/HiPco-SWNT Composites by the Addition of DCl:

To avoid unwanted absorption from water, deuterated hydrochloric acid (DCl) was prepared. 100 mL of 36% w/w HCl solution was dropped into 200 mL of concentrated $H_2SO_4$ solution (98%). The collected HCl gas was again passing through 50 mL of another concentrated $H_2SO_4$ solution and bubbled into 50 mL of a 100% deuterated water ($D_2O$) solution until all of the HCl solution was consumed. The resulting DCl solution was stored in glass container. A pH probe, pre-rinsed with $D_2O$, was immersed into FMN/SWNT solution and a few μL of DCl were added until the desired pH was obtained.

Preparation of Solid FMN-HiPco Sample for X-Ray Measurements 20 mL of the FMN-HiPco dispersion obtained after centrifugation (15 kg=15,000 g and subjected to higher centrifugation forces (65 kg) for 4 hrs to precipitate the majority of dispersed FMN-HiPco SWNT composites. Following decantation of 95% of the 65 kg supernatant, the remaining precipitate (in a form of pellet) was briefly sonicated (at mild sonication power c.a. 75 watts (W)) to produce a homogeneous blackish-green suspension (with volume of ca. 2 mL). This suspension was freeze-dried for 2 days, which left behind a shiny greenish-black FMN-SWNT aerogel-like composite. This FMN-SWNT aerogel-lie composite was carefully inserted into an X-ray microcapillary, prior to conducting X-ray diffraction on it.

Preparation of Pure FMN for X-Ray Measurements 200 mg of FMN (85%, Aldrich) was loaded into flash column chromatograph, equipped with a C-18 reverse column. The chromatography was performed using mobile phase from a gradient that varied from 100% water to final ratio of 70:30=water:methanol at a rate of 3 milliliters per minute (mL/min). At about a 2.5 column volume, the desired FMN can be detected by monitoring 350 nm wavelength. The collected solution was freeze-dried for 2 days and stored in amber vial, to avoid ultraviolet-visible (UV/Vis) radiation.

Preparation of Solid FMN-HiPco Composite Samples for Transmission Electron Micrograph (TEM) Measurements:

The 15 kg FMN-HiPco composite sample was further diluted (100 times) and the solution was drop cast onto a holey carbon TEM grid. The excess water was carefully wicked off from the grid using paper towel and dried in air. The dried TEM sample was further stained with 1 wt % uracil acetate. TEM-based crystallization studies were performed on solid FMN-HiPco samples by suspending ca. 0.1 mg of solid FMN-HiPco into 5 mL of n-hexane and subjecting this suspension to mild-sonication for 10 minutes. The resulting suspension was drop cast on the holey carbon TEM grid.

Replacement of FMN with SDBS in FMN-HiPco Sample:

Initially, 2 mL of FMN-HiPco composite sample was filtered using a Centricon™ Millipore, 3000 molecular weight cut off filter via centrifugation at 5 kg for 1 hour (hr). 2 ml of 1 wt % of sodium dodecyl benzene sulfate (SDBS) in $D_2O$ was added to this filtrate, shaken mildly and re-filtered after 1 hr. This process was repeated for at least 7 to 8 times until the resulting filtrate was devoid of the distinct green fluorescence emission from the FMN. The resulting precipitate was resuspended in 4 ml of 1 wt % of SDBS in $D_2O$ in order to accommodate the limited solubility of SWNT in aqueous SDBS and was bath-sonicated for 6 hr at 20° C. to individualize the majority of nanotubes.

Photoreduction Experiment:

A $D_2O$ dispersion of the FMN-HiPco composite was purged with argon for 1 hr, prior to obtaining both photoluminescence (PL) emission and ultraviolet-visible-near infrared (UV-Vis-NIR) absorption spectra in a sealed cuvette. Special precautions were taken to minimize the possible irradiation by ambient light. Subsequently, the $D_2O$ dispersion of FMN-HiPco composite was irradiated with 365 nm handheld UV light source for 10 minutes and once again both PL emission and UV-Vis-NIR absorption spectra were obtained. Following this, the cuvette seal was broken and air (containing $O_2$) was introduced via bubbling, and both PL emission and UV-Vis-NIR absorption spectra were collected at given time intervals.

Synthesis of the Flavin Derivative—N-Dodecyl-4,5-dimethyl-benzene-1,2-diamine (Hereinafter Compound "2")

A mixture of 4.08 g (30 millimoles (mmol)) of 4,5-dimethyl-benzene-1,2-diamine (hereinafter compound "1") and 2.04 grams (g) (10 mmol) of 1-chloro-dodecane in 20 milliliters (mL) of triethylamine was stirred at 130° C. for 6 hrs under argon. After cooling and addition of dichloromethane (100 mL), the organic solution was washed with aqueous $Na_2CO_3$ solution (10%, 40 mL). The aqueous layer was extracted twice with dichloromethane (2×100 mL). The combined organic extracts were dried over $MgSO_4$ and rotary evaporated to dryness. The thin-layer chromatography retention factor ($R_f$) of the target compound (2) was 0.55 with dichloromethane (MC):methanol (MeOH) (95:5) mixture. Compound (2) was purified by flash chromatography on silica gel in MC:MeOH (95:5) to produce 1.8 g of reddish crystals (60% yield); mp 53-54° C.; $^1$H NMR (400 MHz, $CDCl_3$) δ 6.56 (1H, s), 6.50 (1H, s), 3.20 (3H, broad s), 3.1 (2H, t, J=8 Hz), 2.26 (3H, s), 2.21 (3H, s), 1.68 (2H, q, J=7 Hz), 1.46 (2H, m), 1.34 (16H, s), 0.92 (3H, t, J=8 Hz); $^{13}$C NMR (100 MHz, $CDCl_3$) δ 136.0, 131.8, 128.1, 125.9, 118.4, 113.93, 44.7, 31.9, 29.9, 29.69, 29.65, 29.5, 29.4; Anal. Calcd. for $C_{20}H_{36}N_2$ (MW=304.51): C, 78.88; H, 11.92; N, 9.20. Found: C, 78.95; H, 12.16; N, 9.32.

Figure 5:
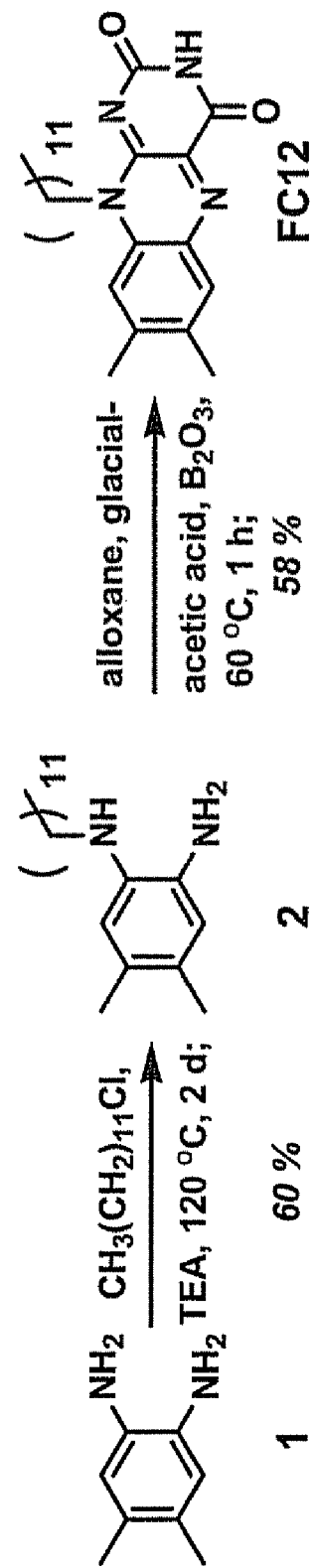
FIG. 5 depicts the reaction conditions for the synthesis of the flavin derivative—10-dodecyl-7,8-dimethyl-10H-benzo[g]pteridine-2,4-dione (FC12)

Synthesis of the Flavin Derivative—10-dodecyl-7,8-dimethyl-10H-benzo[g]pteridine-2,4-dione (FC12) (FIG. 5)

A mixture of 0.578 g (1.9 millimoles (mmol)) of compound (2), 0.284 g (2 mmol) of alloxane monohydrate, 0.42 g (6 mmol) of boric oxide and 60 mL of glacial acetic acid was stirred at 60° C. for 1 hr. The resulting solution was quenched with 100 mL of water and the yellow precipitates were filtered and vacuum-dried. The thin-layer chromatography retention factor ($R_f$) of FC12 was 0.85 with MC:MeOH=95:5 mixture. FC12 was purified by flash chromatography on silica gel in MC:MeOH (95:5) to produce 0.46 g of yellow crystals (58% yield); mp 223-224° C.; $^1$H NMR (400 MHz, $CDCl_3$) δ 8.85 (1H, s), 8.08 (1H, s), 7.41 (1H, s), 4.71 (2H, broad t), 2.59 (3H, s), 2.48 (3H, s), 1.88 (2H, q, J=8 Hz), 1.57 (2H, q, J=8 Hz), 1.51 (2H, m), 1.29 (14H, s), 0.90 (3H, t, J=8 Hz); $^{13}$C NMR (100 MHz, $CDCl_3$) δ 159.6, 155.2, 148.2, 137.0, 136.2, 135.0, 132.9, 131.1, 115.3, 45.36, 31.9, 29.61, 29.59, 29.54, 29.50, 29.32, 29.29, 27.16, 26.9, 22.7, 21.7, 19.5, 14.1; $\lambda_{max}$(∈) 443 nm (11 964); Anal. Calcd. for $C_{24}H_{34}N_4O_2$ (MW=410.55): C, 70.21; H, 8.35; N, 13.65; 0, 7.79. Found: C, 70.09; H, 8.85; N, 13.41.

Dynamic light scattering (DLS) was performed using NiCOMP 380/DLS submicron particle size analyzer equipped with a 633 nm laser (operating at a power of 5 mW), in which scattered light was collected at 90 degrees. Prior to conducting the measurements, all samples were equilibrated at least for 10 minutes (min) at 20° C. to establish thermal and convectional stability.

Deconvolution of Vis-NIR Absorption Spectra were carried out by subtracting a power-law function ($a\lambda^{-b}$, where λ is the wavelength and a, b are fitted parameters). The b value was obtained from an optimum fit of the background signal. Peak deconvolution using Lorentzian peak profiles were found to produce an optimum fit. In the case of slightly bundled nanotube samples, deconvolution of their NIR absorption spectra was performed using Voigt peak profiles.

Photoluminescence (PL) Quantum Yield (QY) Measurements were performed using Styryl-13 (2-[p-dimethylaminophenyl)-2,4-neopentylene-1,3,5,7-octatetraenyl]-3-ethyl-(6,7-benzo)-benzothiazolium perchlorate) as a reference dye, with 11% reported QY ($\eta_{ref}$) according to Crochet et al. (*J. Am. Chem. Soc.* 2007, 129, (26), 8058-8059). The sample QY ($\eta_s$) was determined based on equation (1), $$\eta_s = \eta_{ref} \times \frac{I_s \times \alpha_{ref} \times n_s^2}{I_{ref} \times \alpha_s \times n_{ref}^2} \quad (1)$$

where I is the integrated area of photoluminescence emission, α is the extinction coefficient at the excitation wavelength, and n is the refractive index of the solvent, for the sample (s) and reference (ref), respectively. The extinction coefficient α was obtained from the respective peak height of the absorption band at the excitation wavelength. The concentration of all samples was adjusted to similar absorption values (i.e. less than 0.05) at 580 nm. The emission spectra of Styryl-13 (in methanol), FC12/SWNTs (in toluene), and SDS/SWNTs (in $D_2O$) were recorded at 580, 583, and 569 nm, excitation wavelengths, using the same slit widths for the mercury lamp as well as the excitation and emission monochrometers. In order to determine the concentration dependence of PL QY of SDS-dispersed SWNTs, a stock SDS/SWNTs $D_2O$ dispersion was diluted with 1% w/v SDS dispersion in $D_2O$ to maintain the similar SDBS concentration throughout the experiment.

Example 1

This example was conducted to demonstrate the ability of SWNTs to be helically bound by flavin moieties. A representative procedure for dispersing SWNTs with flavin mononucleotide (FMN), FAD and riboflavin involves a 4 hours cup horn sonication of SWNTs in $H_2O$ or $D_2O$. This is followed by 2 hours of centrifugation at 15 kg, where the upper 70 to 80% of the supernatant was decanted for further investigation. As noted above, the FIG. 1 illustrates the chemical structure of riboflavin, FMN, and FAD used for such aqueous dispersion of SWNTs. While the basic flavin moiety is hydrophobic, these flavin derivatives have water-miscible tail groups. Such amphiphilic structures together with the aforementioned strong π-π interactions with both metallic and semiconducting SWNTs, can explain the effective nanotube dispersion in aqueous media.

Figure 6:
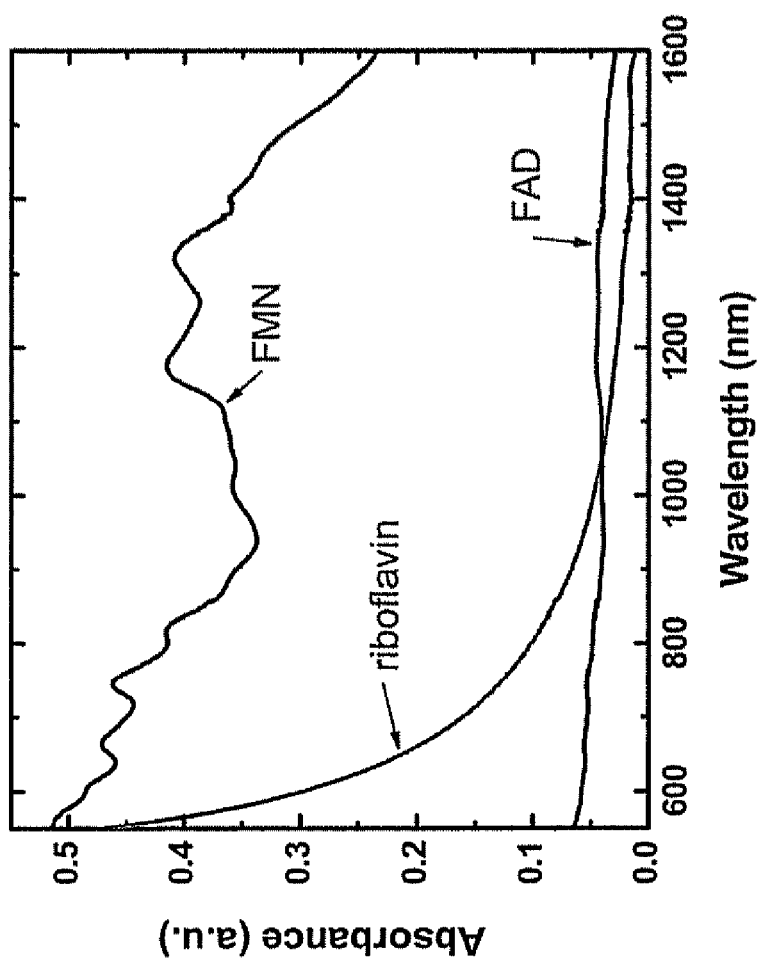
FIG. 6 shows the UV-Vis-NIR spectra for SWNT dispersed in $D_2O$ in the presence of FMN, FAD, and riboflavin. Peaks at 1400-1600 nm at the riboflavin and FAD spectra originate from water contamination in $D_2O$.

FIG. 6 illustrates the UV-Vis-NIR spectra of HiPco dispersions with FMN, FAD, and riboflavin. The first ($E_{11}^S$) and second ($E_{22}^S$) optical transitions of semiconducting SWNTs can be witnessed in 550 to 900 nm and 950 to 1600 nm range, respectively. Those $E_{11}^S$ and $E_{22}^S$ features are clearly apparent for the FMN and FAD spectra, which are in good accordance with that of SDBS-dispersed HiPco SWNTs. While riboflavin appears not to exhibit such solubilization ability, this is due to its insolubility in neutral aqueous media. Upon sonication of riboflavin-SWNT in basic media (pH 11), the resulting dispersions recover the aforementioned $E_{11}^S$ and $E_{22}^S$ features (data not shown), which indicates the successful dispersion of SWNTs. Overall, FMN appears to provide the highest nanotube solubilization/dispersibility power.

The recovery of SWNT (as a precipitate) from this dispersion can be readily accomplished by the introduction of reducing agents (e.g., sodium dithionite ($Na_2S_2O_4$) and sodium borohydride ($NaBH_3$), and the like). These agents reduce FMN to $FMNH_2$, which lower substantially the flavin/ nanotube π-π interactions, by breaking the conjugation of the isoalloxazine ring with the nanotubes.

Example 2

Photoluminescence Behavior and Charge-Transfer Complex Formation

Figure 7:
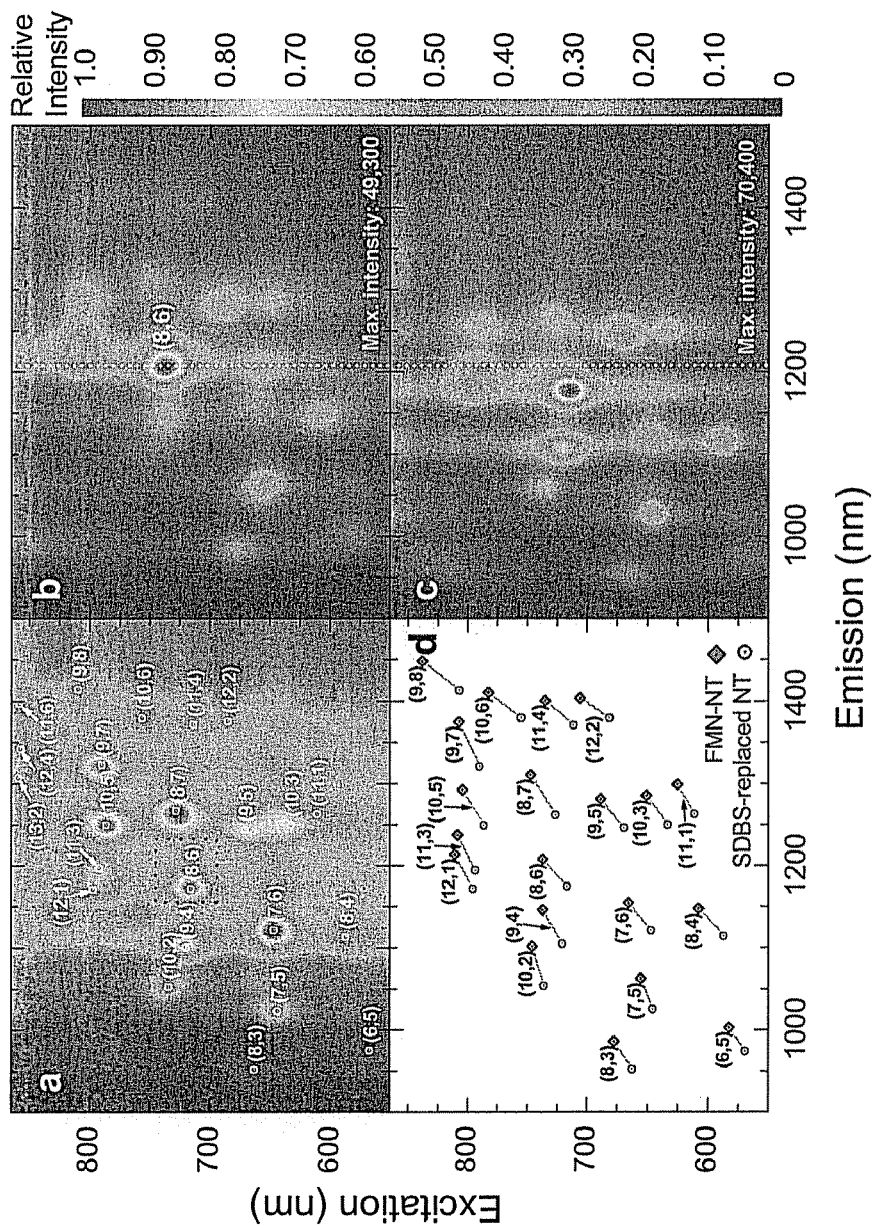
FIG. 7 shows the photoluminescence excitation (PLE) maps of (a) SDBS/HiPco-SWNTs (b) FMN/HiPco-SWNTs centrifuged at 50,000 g, (c) after addition of 7.4 mM of SDBS in sample (b), and (d) recorded peak shifts for using different surfactants (i.e., SDBS, FMN and mixture of FMN and SDBS)

The centrifuged FMN/HiPco-SWNT solution (i.e., the composite solution) was further investigated with photoluminescence excitation (PLE) mapping. The results are shown in the FIGS. 7(a) through 7(d). FIG. 7(a)-(c) illustrates the contour plots of PLE mapping of (a) SDBS/SWNTs, (b) FMN/SWNTs (centrifuged at 50 kg), and (c) following the addition of 7.4 mM of SDBS in sample (b). The spectroscopic local and relative intensity of FIG. 7(a) closely resembles that of SDBS-dispersed HiPco SWNT. Surprisingly, the FMN dispersed nanotubes, shown in FIG. 7(b), show a significantly narrower nanotube abundance and intensity distribution, as compared to that of FIG. 7(a). In addition as shown in FIG. 7(d) the presence of FMN results in an overall redshift for both $E_{11}^S$ and $E_{22}^S$ of semiconducting SWNTs. Based on the $E_{11}^S$ and $E_{22}^S$ blue-shift back to their original SDBS position, it is estimated that at 7.4 mM of SDBS, SBBS has replaced completely FMN without any apparent nanotube precipitation.

Once SDBS is introduced in the FMN/SWNT dispersion of that of FIG. 7(b) and the sample is gently shaken (FIG. 7(c)), the PL emission of certain (n,m)-SWNTs changed completely. For example, while the signal from (10,2) and (7,5) SWNTs are clearly absent in FIG. 7(b), they re-appear in FIG. 7c). Moreover, the (n,m)-SWNTs show markedly intensity ratios between FIGS. 7(b) and 7(c). Upon closer examination of the peaks from (9,4) and (8,6) in FMN-HiPco composite sample, the peak intensity of (8,6) appears to be significantly greater than that of (9,4). The introduction of SDBS in the solution makes such peak intensity difference less profound. Similarly, the intensity of (8,3) appears greater than that of (7,5) in FIG. 7(b), but introduction of SDBS reversed this trend in FIG. 7(c). This indicates that FMN interacts selectively with certain (n,m)-SWNTs resulting a complete or partial quenching of their luminescence. This however, is not the case for larger diameter SWNTs (i.e. (12,2), (11,4), (10, 6), and (9,8)-SWNTs with diameters ($d_t$) ranging from 1.05 to 1.15 nm, which appear to have been selectively removed from the FMN dispersion process.

Example 3

Diameter Selectivity of Flavins

Figure 8:
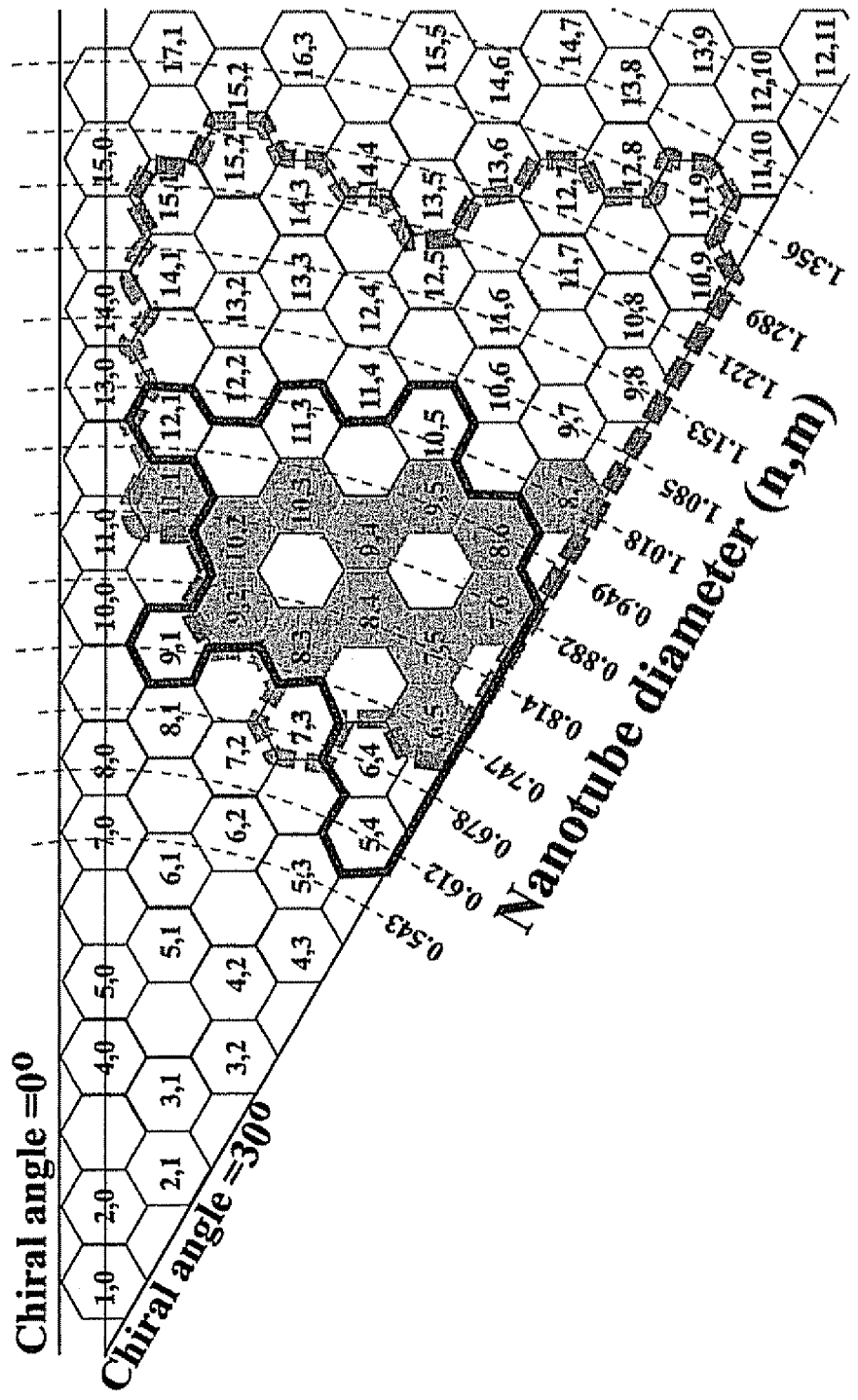
FIG. 8 illustrates the (n,m)-SWNT occurrence in typical HiPco (broken line), CoMoCAT (solid line) and Co MCM-41 (shaded polygons) SWNT samples.

As explained above (FIG. 7), the FMN-dispersed HiPco-SWNT sample possesses a much-narrowed distribution than that of the starting (as-supplied) HiPco sample. This narrower distribution is believed to be due to separation according to diameter (i.e., diameter enrichment). To verify such diameter enrichment, different nanotube samples were investigated. FIG. 8 illustrates the (n,m)-SWNT occurrence in typical HiPco, CoMoCAT and Co-MCM-41 SWNT samples. In the FIG. 8, the distribution of semiconducting SWNTs from three different samples; (a) HiPco SWNT (broken line), (b) CoMoCAT SWNT (solid line), and (c) Co-MCM-41 (shaded hexagons) SWNT distribution are shown. Two larger diameter SWNTs (i.e. H-SWNT, N-SWNT), as defined in the experimental section, with average diameter ($d_t$) distributions greater than 1 nm were also investigated.

Figure 9:
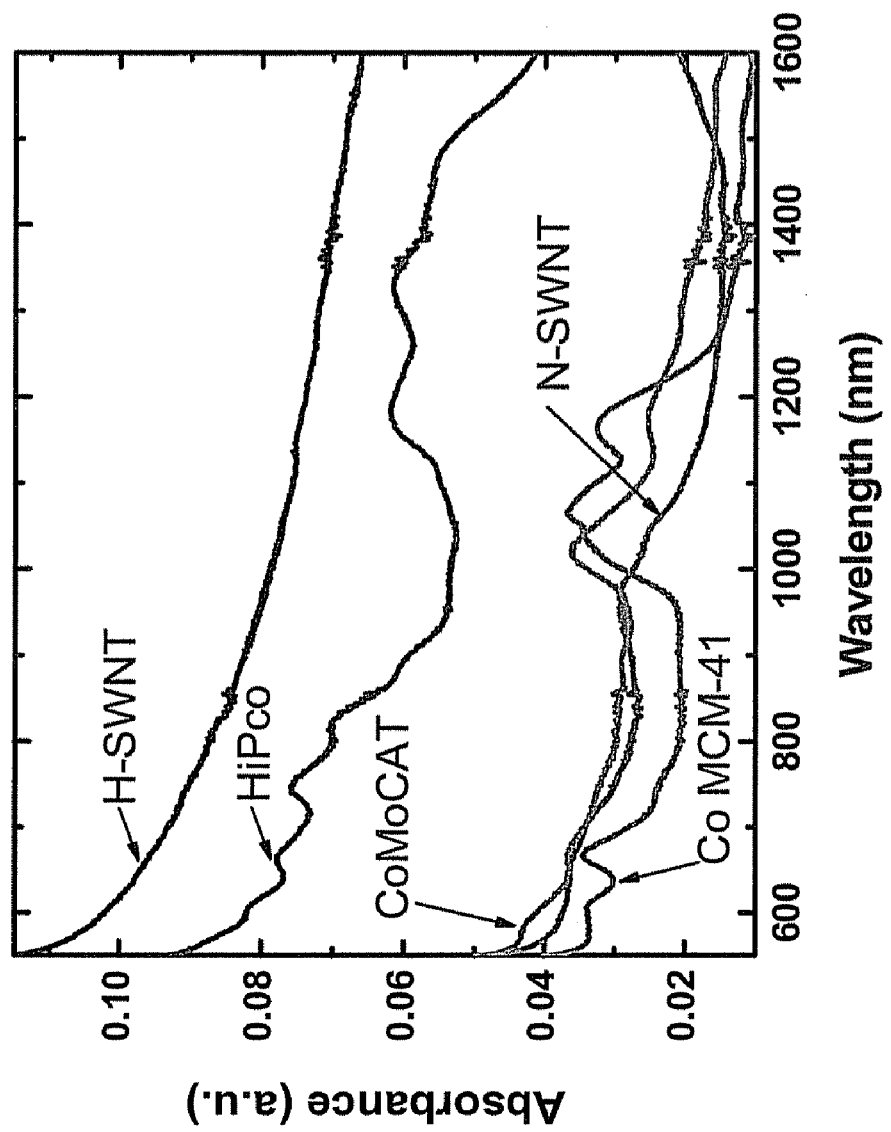
FIG. 9 illustrates the Vis-NIR spectra of FMN-dispersed SWNTs from various nanotube synthesis methods.

FIG. 9 illustrates the Vis-NIR spectra of FMN-dispersed SWNTs based on the aforementioned synthetic methods. The dispersion from FMN with various SWNT dispersions showed completely different optical density in Vis-NIR region according to SWNT $d_t$ distribution. Clearly, H-SWNT showed highest optical density in the spectrum, which illustrates an almost featureless monotonous decrease due to large diameter distribution (ca. 1-3 nm). HiPco showed relatively strong optical density, showing $E_{11}^S$ and $E_{22}^S$ of semiconducting SWNTs in the 600 to 900 nm and the 950-1350 nm wavelength region respectively. UV-Vis-NIR spectra from CoMoCAT resolved (6,5)-enriched $E_{11}^S$ and $E_{22}^S$ of semiconducting SWNT in the 600 and 1000 nm respectively. UV-Vis-NIR spectra of N-SWNT showed absorptions, originating from $E_{22}^S$ of semiconducting and $E_{11}^M$ of metallic SWNTs. Co-MCM-41 showed (7,5)-enriched $E_{11}^S$ and $E_{22}^S$ of SWNT, which is in good agreement with previous results.

FIGS. 10(a)-(d) illustrates the corresponding PLE maps of the four FMN-dispersed SWNTs samples, having different diameter distributions. Since PL originates from relatively individualized or lightly bundled SWNT samples, broad absorptions in FIG. 9 should not contribute to the PLE maps.

Figure 10:
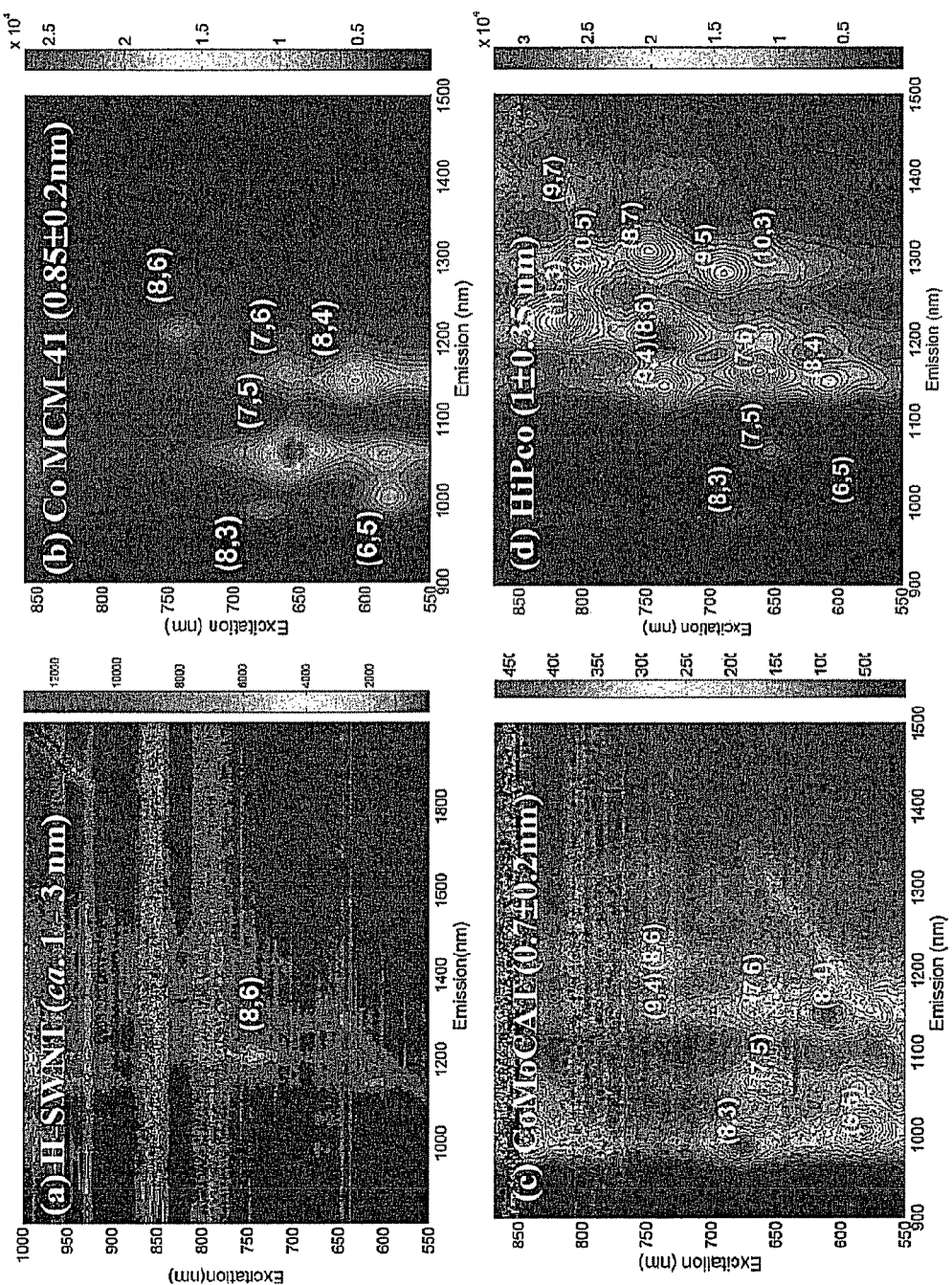
FIG. 10(a)-(d) illustrates the corresponding PLE maps of FMN-dispersed (a) H-SWNTs, (b) Co-MCM-41 SWNTs, (c) CoMo-CAT SWNTs, and (d) HiPco SWNTs having different diameter distributions (indicated in brackets)

In the case of N-SWNT ($d_t$=1.4±0.4 nm) no PLE was observed (data not shown). In the case of H-SWNT sample (broad $d_t$ distribution spanning from 1-3 nm), FIG. 10(a) shows only a faint PLE peak from the (8,6)-SWNT. This, together with the N-SWNT sample indicate that FMN has hard time suspending individually or in small bundles nanotubes within 1-2 nm in diameter (2-3 nm fall out of the detection range of the PLE fluorimeter used in this study). FIGS. 10(b)-(d) indicate that nanotubes with smaller than 1.02 nm in diameter get effectively individualized by the FMN treatment. In particular, the FMN/HiPco-SWNT composite, mapped in FIG. 10(b), shows a variety of (n,m)-SWNT in the maps, with $d_t$ distribution from 0.77-1.02 nm. The charge-transfer between FMN and SWNT create certain types of (n,m) quenching. The two narrowly distributed SWNT samples (i.e., Co-MCM-41 and CoMoCAT) get also effectively individualized by the FMN treatment. While the distribution of FMN/Co-MCM-41-SWNT is similar to the SDBS/Co-MCM-41, FMN/CoMoCAT-SWNT in FIG. 10(c) does not showed (6,5)-enriched PLE map. Without being limited by theory, this might originate from the aforementioned charge-transfer quenching.

Example 4

Chirality Selectivity

The PL results shown in FIGS. 10(b) and (d) demonstrate the selectivity of the flavin-based surfactant for small diameter nanotubes. Two different diameter ranges were tested (HiPco, 1±0.35 nm and Co-MCM-41, 0.85±0.15 nm).

Figure 11A:
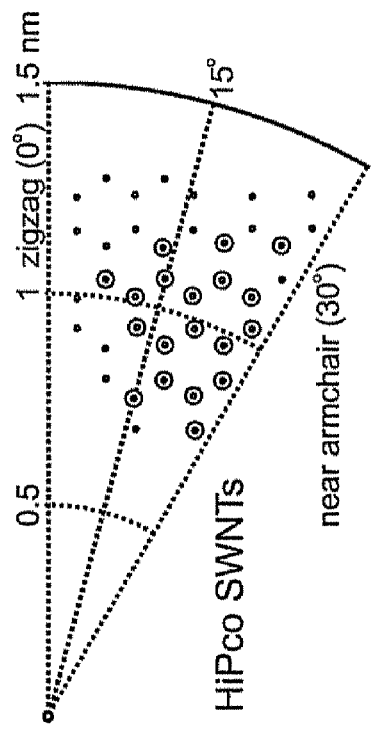
FIG. 11 illustrates chirality enrichment patterns of FMN with respect to HiPco and Co MCM-41. Chirality enrichment patterns SWNT for HiPco (left) and Co MCM-41 (right) samples. Dots represent various (n,m) chiralities of HiPco and Co MCM-41 SWNTs. Circled dots represent the chirality enriched (n,m)-SWNTs in both samples, using FMN-suspension subjected to 15 kg centrifugation. No intensity information is provided, only abundance.
Figure 11B:
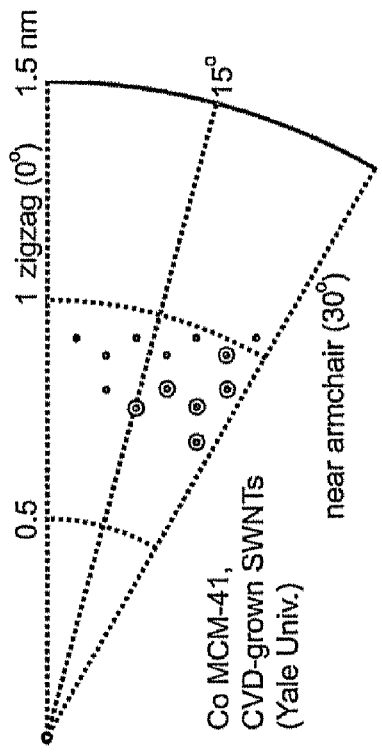

FIG. 11 illustrates selectivity of FMN with respect to HiPco and Co-MCM-41. Chirality enrichment patterns SWNT for HiPco (left) and Co-MCM-41 (right) samples are shown in the FIG. 11. The dots represent the various (n,m) SDBS- and DNA-dispersed HiPco and Co-MCM-41 SWNTs samples in the figures on the left and the right, respectively. The circled dots represent the chirality enriched (n,m)-SWNTs in both samples, using FMN-suspension at 15 kg centrifugation speed. No intensity information is provided in these figures, only abundance.

FMN appears to individualize 19 (n,m) chirality HiPco SWNT species out of 38 species, which are subsequently removed from their bundles by the centrifugation method described above. Most of 19 HiPco SWNTs appear to be located at higher chiral angles, although this might be an artifact of the aforementioned charge-transfer issue. Likewise, 6 out of 13 Co-MCM-41 SWNTs have been selected from the high chiral angle. This implies that the chirality separation is universal through out the diameter distribution and the diameter selectivity is ranging from 0.7 to 1.1 nm.

Figure 12:
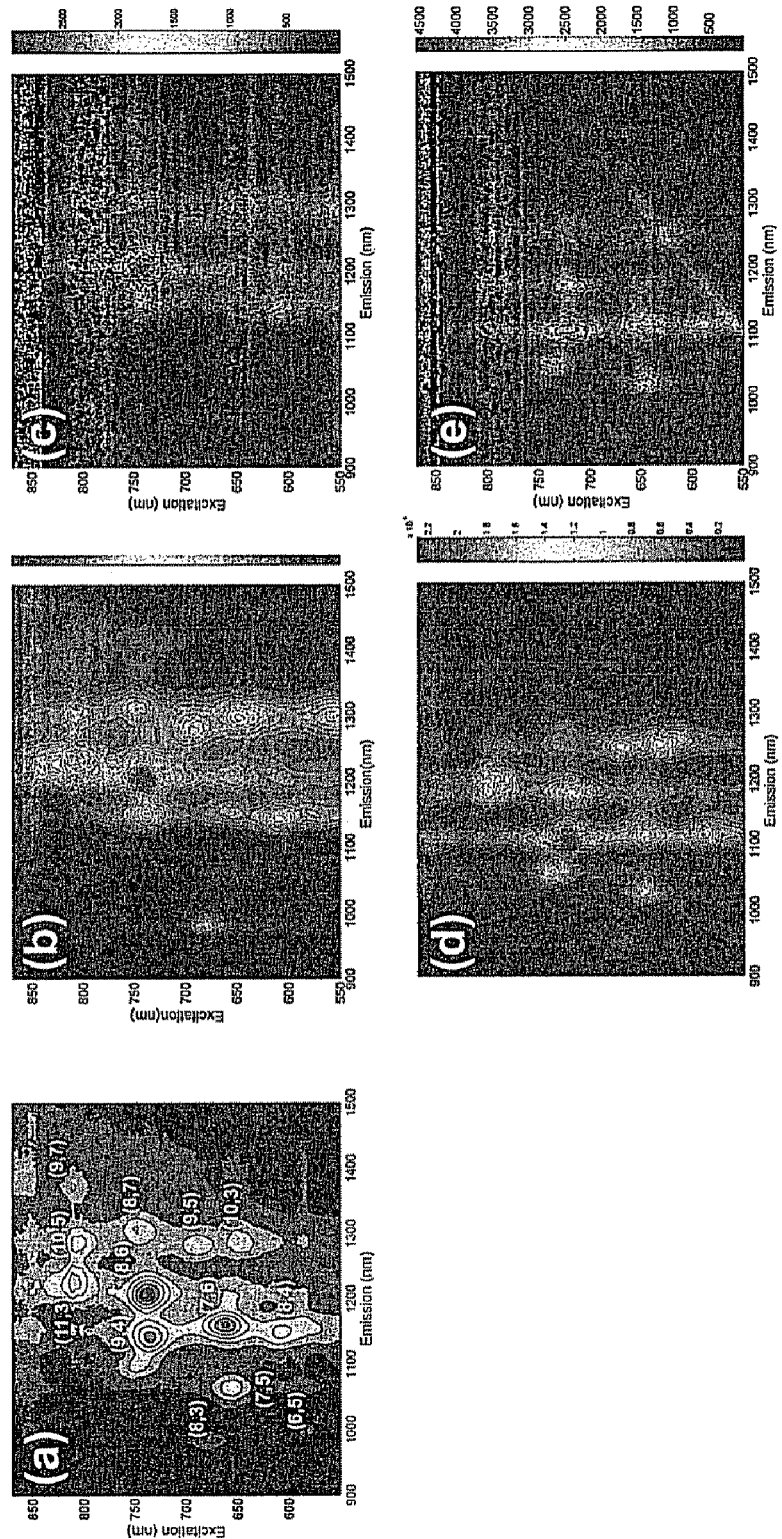
FIGS. 12(a)-(e) illustrate that diameter selectivity can be further improved by increasing the relative centrifugal force (e.g., by increasing acceleration due to gravity "g").

This diameter selectivity can be further improved by increasing the relative centrifugal force (RCF, i.e. g). The results are shown in the FIG. 12. FIGS. 12(a) through 12(c) illustrate PLE maps of FMN/HiPco-SWNT composite dispersion centrifuged at different values of the acceleration due to gravity "g". The sample centrifuged at 15 kg was showing 13 different SWNTs, which is in good agreement in with the PL data of the FIG. 7(b). As RCF values increase, diameter distribution becomes much narrowed and (8,6) appears to be dominant in the presence of only FMN. Sample centrifuged at 170 kg (170,000 times the acceleration due to gravity "g") shows (8,6) as a major peak, with (8,4) and (10, 3) as minor peaks.

When 1 wt % of SDBS was added to the 50 and 170 kg samples, 6 to 7 of the original 38 different (n,m) semiconducting SWNTs in HiPco are retained (FIGS. 12(d) and (e)) (i.e., (9,4) (10,2), (8,6), (7,6) (8,4) and (7,5) with diameters of 0.92, 0.88, 0.97, 0.89, 0.84 and 0.83 nm, respectively. The strong presence of the (9,4) sem-SWNT might also signify that the FMN organization appears to favor nanotubes with diameters around 0.9 nm.

Example 5

Metallic Vs. Semiconducting SWNT Separation

Since the FMN UV-Vis absorption blocks the $E_{11}^M$ absorption range (480-600 nm for HiPco SWNTs) from metallic SWNTs, the replacement of FMN with SDBS is necessary to decipher whether FMN-dispersion followed by centrifugation at various speeds affords separation by type (metallic vs. semiconducting).

Figure 13B:
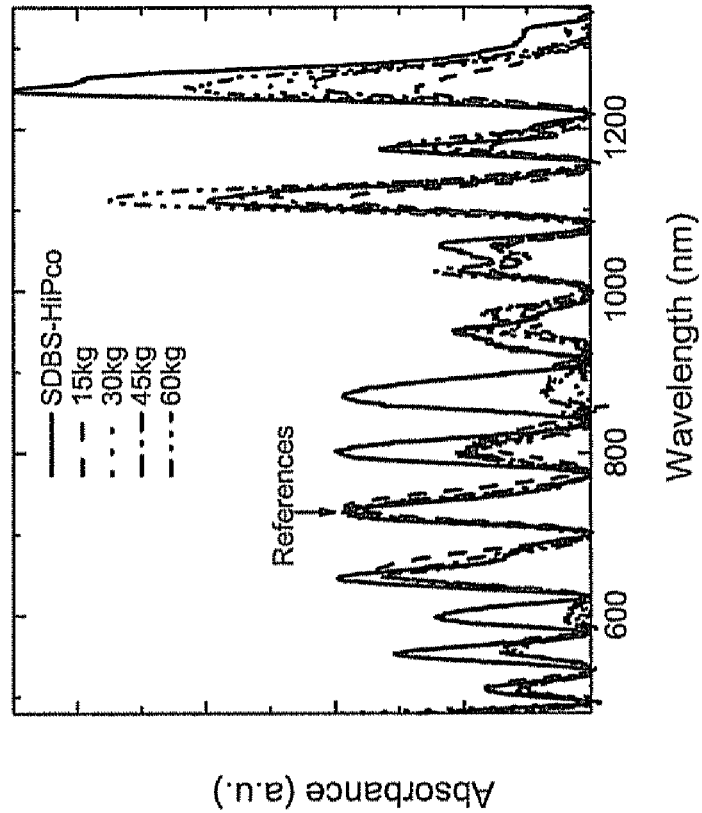
FIGS. 13(a) and 13(b) illustrate the UV-Vis-NIR of FMN-dispersed HiPco SWNTs as a function of centrifugation speed. The FMN-dispersed nanotubes have been replaced with SDBS to allow visualization of the 400-550 nm spectral region.
Figure 13A:
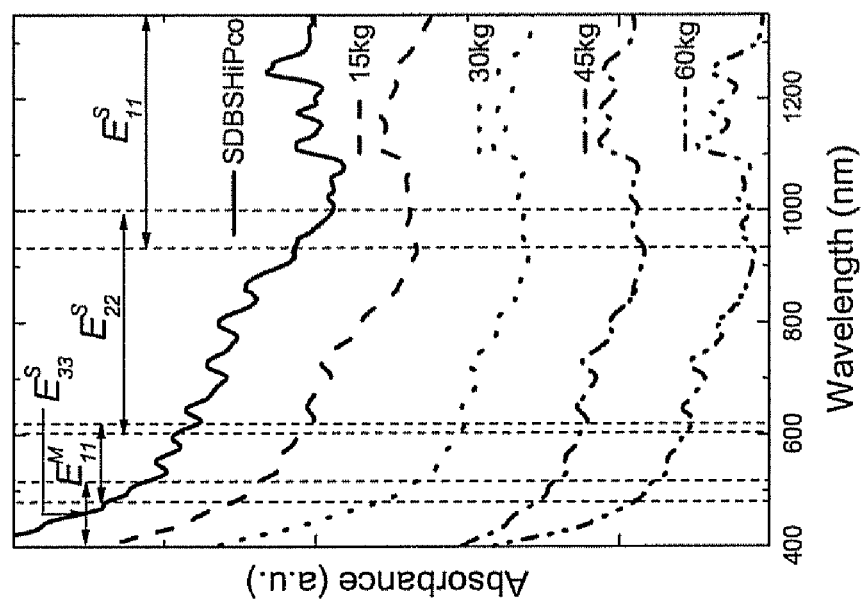

Such FMN replacement was performed using micro-dialysis, as described in the Experimental Section. FIGS. 13(a) and 13(b) illustrate the UV-Vis-NIR of FMN-dispersed HiPco SWNTs as a function of centrifugation speed. The FMN-dispersed nanotubes have been replaced with SDBS to allow visualization of the 400-550 nm spectral region. In FIG. 13(b), the background from scattering, amorphous carbon and π-plasmon contribution is removed. Both figures have been normalized with respect to the 723 nm peak, which corresponds to $E_{22}^S$ absorption of the HiPco SWNTs with average diameter of ca. 0.9 nm. From a first observation of the 480-600 nm region in FIG. 13(a), it can be concluded the initial FMN treatment results in significant removal of metallic SWNTs. Following background subtraction (FIG. 13(b)), one can conclude that increasing the centrifugal force, affords only minor enrichment by type, from observation of the 550 and 600 nm peaks, respectively. Moreover, it appears that larger diameter metallic SWNTs (600 nm peak) meet the similar fate of the larger $d_t$ semiconducting SWNTs (800 and 870 nm peaks), which are also removed by the FMN treatment (vide supra).

Example 6

Effect of pH-Induced Doping of FMN-Dispersed SWNTs

Figure 14B:
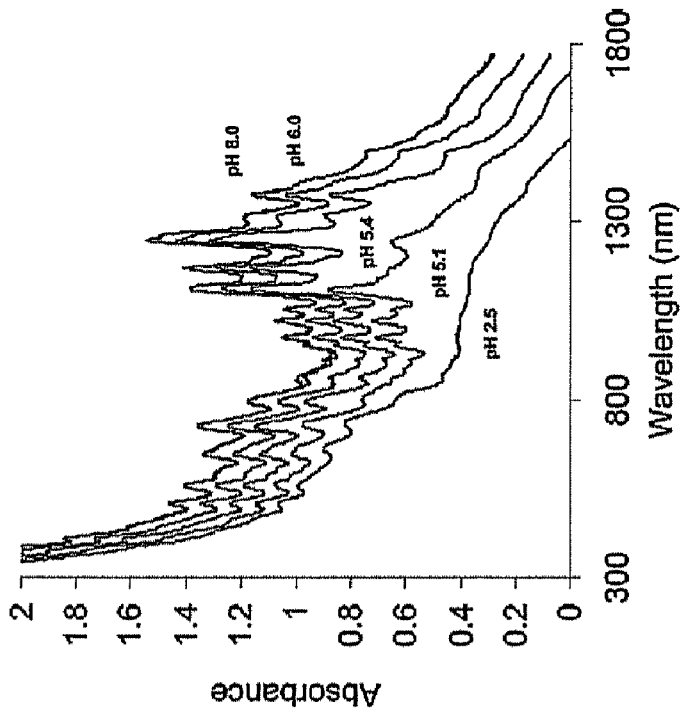
FIG. 14(b) illustrates the corresponding UV-Vis-NIR spectra of sodium dodecyl sulfate (SDS)-dispersed HiPco SWNTs as a function of pH, as reported by Strano et al. (*J. Phys. Chem. B*, (2003) 107 (29), 6979-6985)

Strano et al. (*J. Phys. Chem. B*, (2003) 107 (29), 6979-6985) have shown that pH selectively dopes SWNTs. By lowering the pH, larger diameter nanotubes dope faster than smaller diameter SWNTs (FIG. 14(b)). FIG. 13(a) illustrates the UV-Vis-NIR spectra of FMN-dispersed SWNTs at various pHs. While with increasing acidity, larger $d_t$ SWNTs get progressively depleted in sodium dodecyl sulfate (SDBS)-dispersed HiPco, the same is not true for FMN-dispersed nanotubes, whose $E_{11}^S$ absorptions remain relatively unchanged. Around pH=3.7, FMN-dispersed SWNTs starts to undergo mild precipitation, presumably due to reaching the isoelectric point of the phosphate group in the FMN moiety. This indicates that FMN-dispersed SWNTs are resistant to acid-induced doping. Kim et al. (*Nano Lett.*, 2005, 5(12), 2500-2504) suggested that acid-induced doping takes place through oxygen-assisted nanotube oxidation based on equation (2),

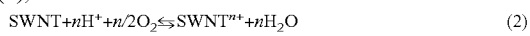

$$SWNT + nH^+ + n/2 O_2 \leftrightarrows SWNT^{n+} + nH_2O \qquad (2)$$

Figure 14A:
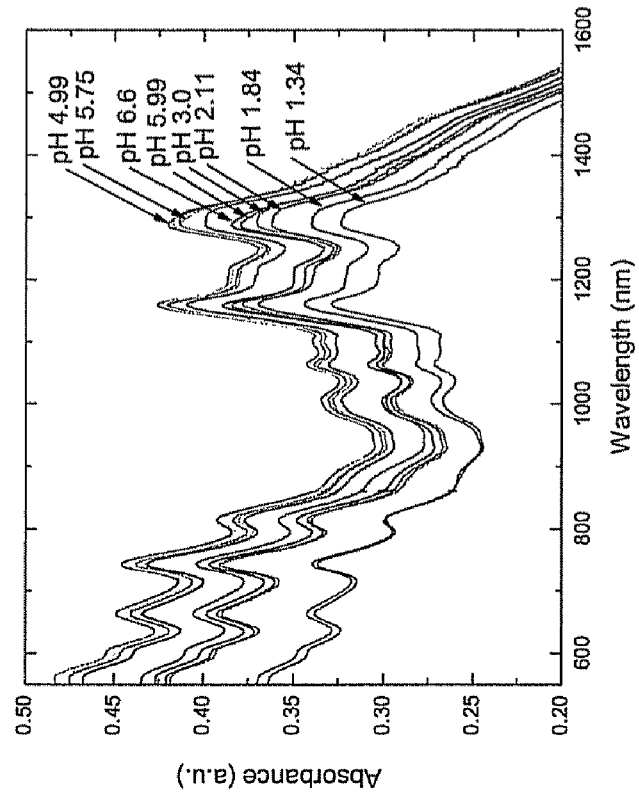
FIG. 14(a) illustrates the UV-Vis-NIR spectra of FMN-dispersed HiPco SWNTs at different pHs.

Moreover, exclusion of oxygen was shown to inhibit acid-induced nanotube doping. Since no special care was taken to exclude $O_2$ from the FMN-suspensions in FIG. 14(a), this provides the first indication that the helical wrapping of FMN around SWNTs might be able to exclude oxygen, thereby preventing nanotubes for getting doped at lower acidic environments. This is a very important attribute of the flavin-induced solubilization in the area of luminescent applications of various (n,m) nanotubes for biosensor applications. While other individualization techniques (i.e., the use of sodium dodecyl sulfate (SDS), sodium dodecyl benzene sulfonate (SDBS), sodium cholate, deoxyribonucleic acid (DNA), and the like.) provide susceptibility of luminescence to changing pH, FMN-wrapped nanotubes do not. This will be further discussed later.

Example 7

FMN Organization onto SWNTs

In order to understand the FMN organization onto SWNTs, these FMN/HiPco-SWNT composite dispersions were investigated with TEM. Following casting and drying dilute aqueous FMN/HiPco-SWNT composite mixtures onto holey carbon grids, these samples were stained with 1% uracil acetate to provide sufficient contrast to facilitate observation of the biological entities (i.e. FMN) physisorbed onto SWNTs. FIGS. 15(a)-(f) illustrates six representative HRTEM images of uracil acetate-stained FMN/HiPco SWNTs. The helical wrapping of FMN around these individualized SWNTs are profound in all figures but especially obvious at the lower part of FIGS. 15(e) and (f) and the middle part of FIG. 15(c). The pitch of these helical wrappings is of the order of 30 degrees (see FIG. 16), forming a ribbon like pattern of FMN around the SWNTs. The periodic undulations of these ribbons along the SWNT occur every 2.5 or 5 nm (see arrows in FIG. 16). These ribbons are expected to originate from the collapsed d-ribityl phosphate side chains of FMN. During the drying process, the d-ribityl phosphate side chains collapse either in groups of two (forming a repeat of 2.5 nm) or in groups of four (with the center two forming the highest peaks where the adjacent two, from each side, collapse on) forming a pitch of 5 nm (see FIG. 16). What is important is that both d-ribityl phosphate side chain configurations maintain their 35 degrees helical wrapping around these SWNTs, as shown from HRTEM results and are simulated structures in FIG. 16.

Example 8

SWNT-Induced Long Range Crystallization of Unbound FMN

Figure 15:
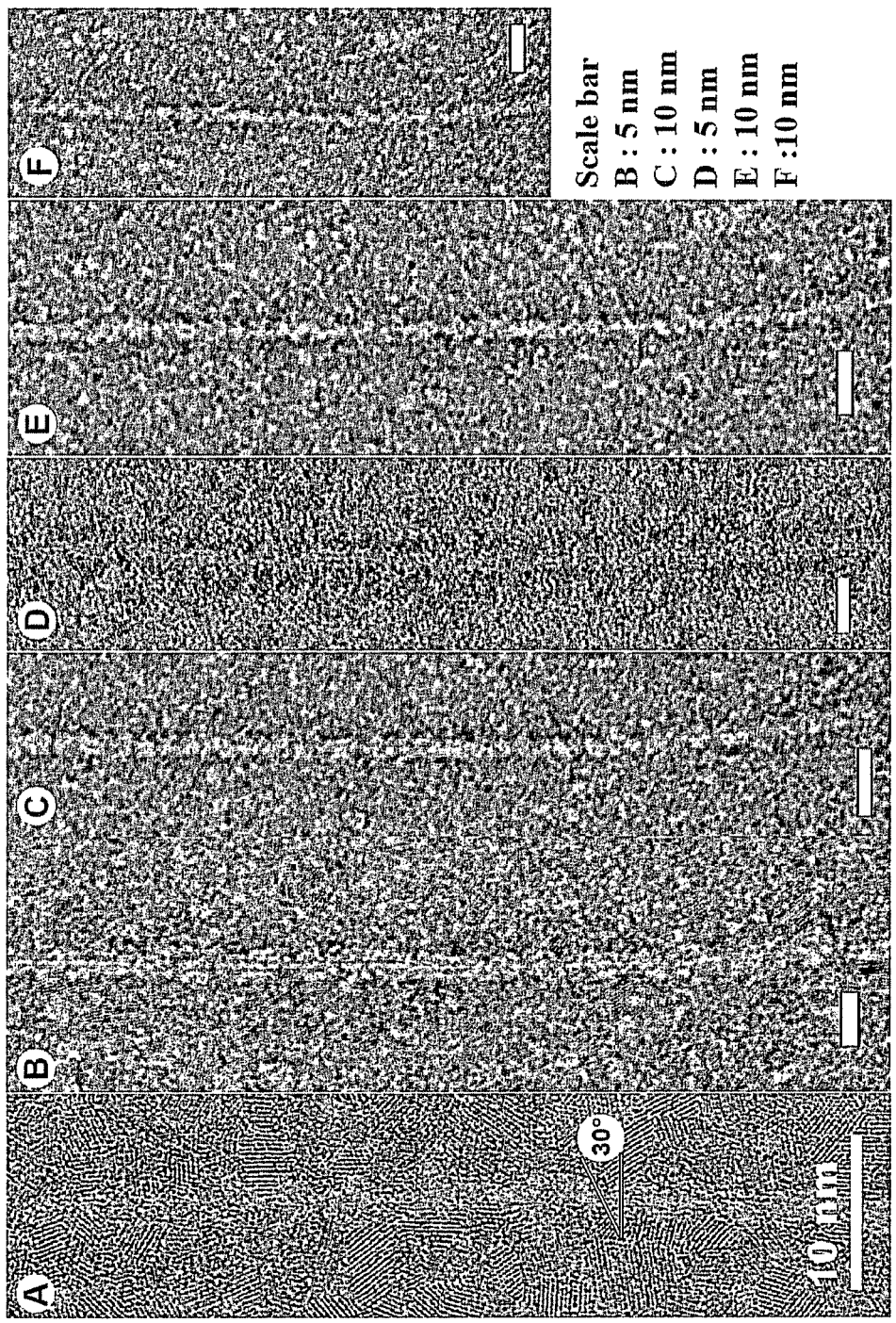
FIGS. 15(a)-(f) illustrates six representative HRTEM images of uracil acetate-stained FMN/HiPco SWNT composites.
Figure 16:
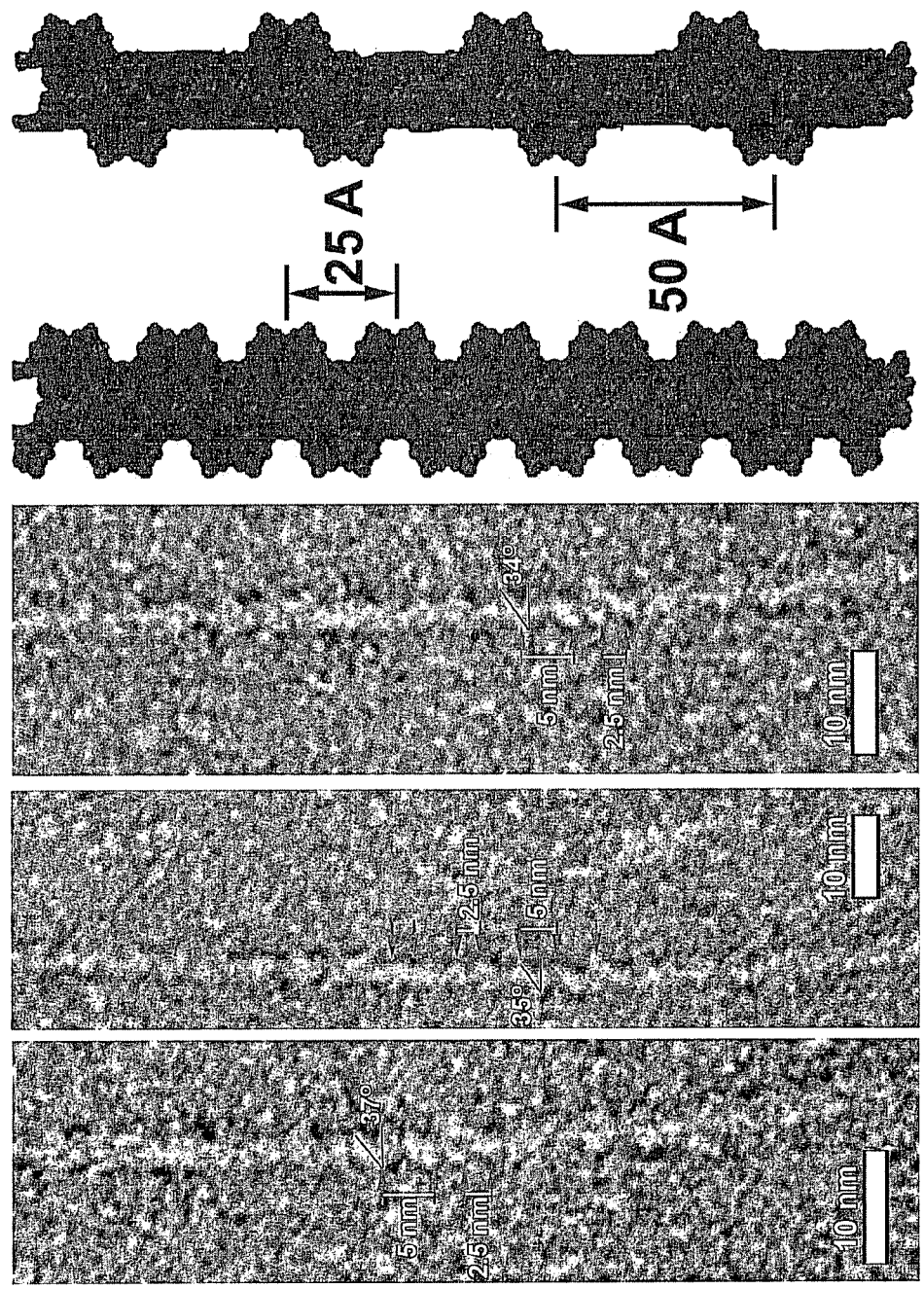
FIG. 16 provides enlarged TEM images of FMN-wrapped SWNTs along with a comparison with their simulated structures.

The data from the FIGS. 15 and 16 indicate that FMN organizes onto the side walls of the SWNTs. In order to determine whether long range organization (i.e. ordered crystalline structures) were present, the centrifuged FMN/HiPco-SWNT solution was lyophilized to result in a greenish-black silk-like fine aerogel (3 mg of FMN-HiPco aerogel-like composite in 2 mL volume). Surprisingly enough, the lyophilized sample self aligns into macroscopic fibers.

Figure 17:
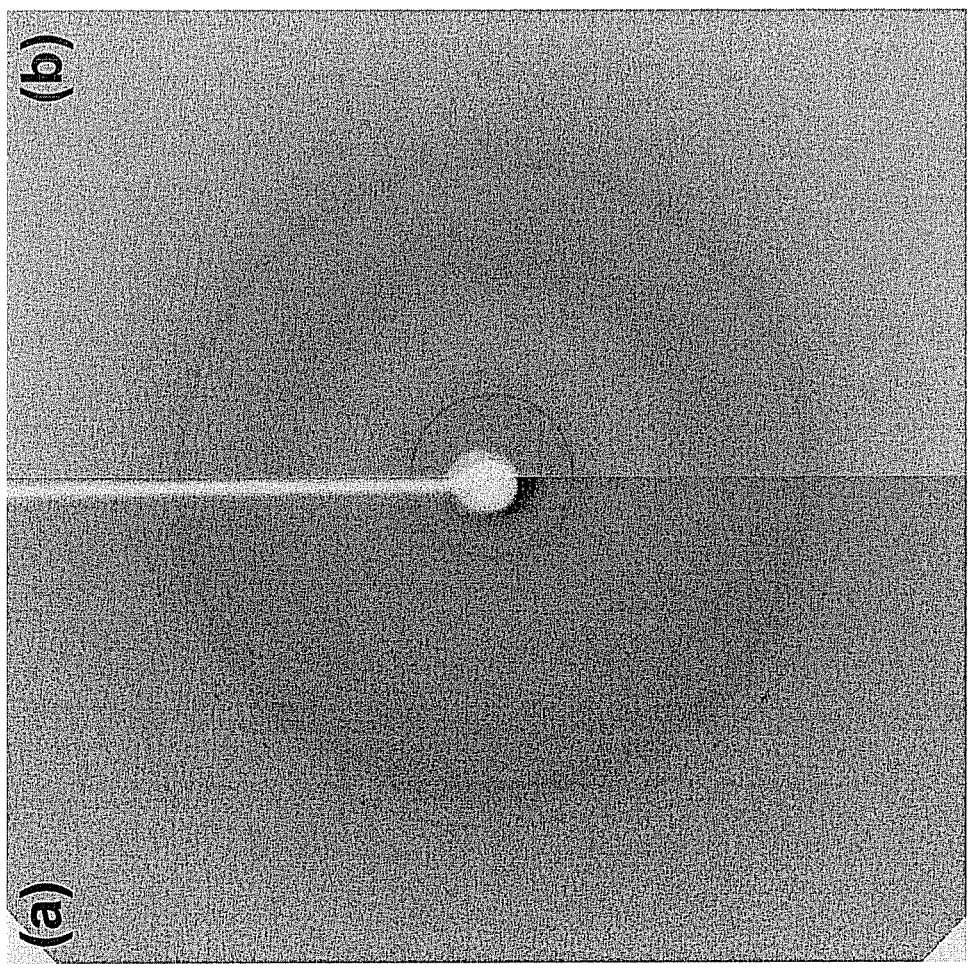
FIG. 17 is a 2D X-ray powder diffraction pattern of (a) lyophilized FMN-HiPco composite and (b) highly purified & lyophilized FMN.

FIGS. 17(a) and (b) illustrates the 2D X-ray powder diffraction patterns of the solid FMN/HiPco-SWNT composite (a) versus that of a highly purified FMN sample (b). Here it is to be noted that the FMN that was used in the SWNT dispersion/centrifugation process is ca. 85% pure, as opposed to the highly purified FMN sample, which was purified via liquid chromatography (using $C_{18}$-reverse column) to nearly 100%. Upon closer inspection of both FIGS. 14(a) and 14(b), the underlying similarities of both diffraction patterns can be seen. However, the FMN/HiPco-SWNT composite diffraction pattern exhibits considerably higher crystallinity than the pure FMN. Moreover, the FMN/HiPco-SWNT composite diffraction pattern exhibits a distinct spot-like diffraction pattern on top of the ring-like polycrystalline pattern. These diffraction spots are lined up with themselves indicating that they originate from the distinct crystalline grains.

Figure 18:
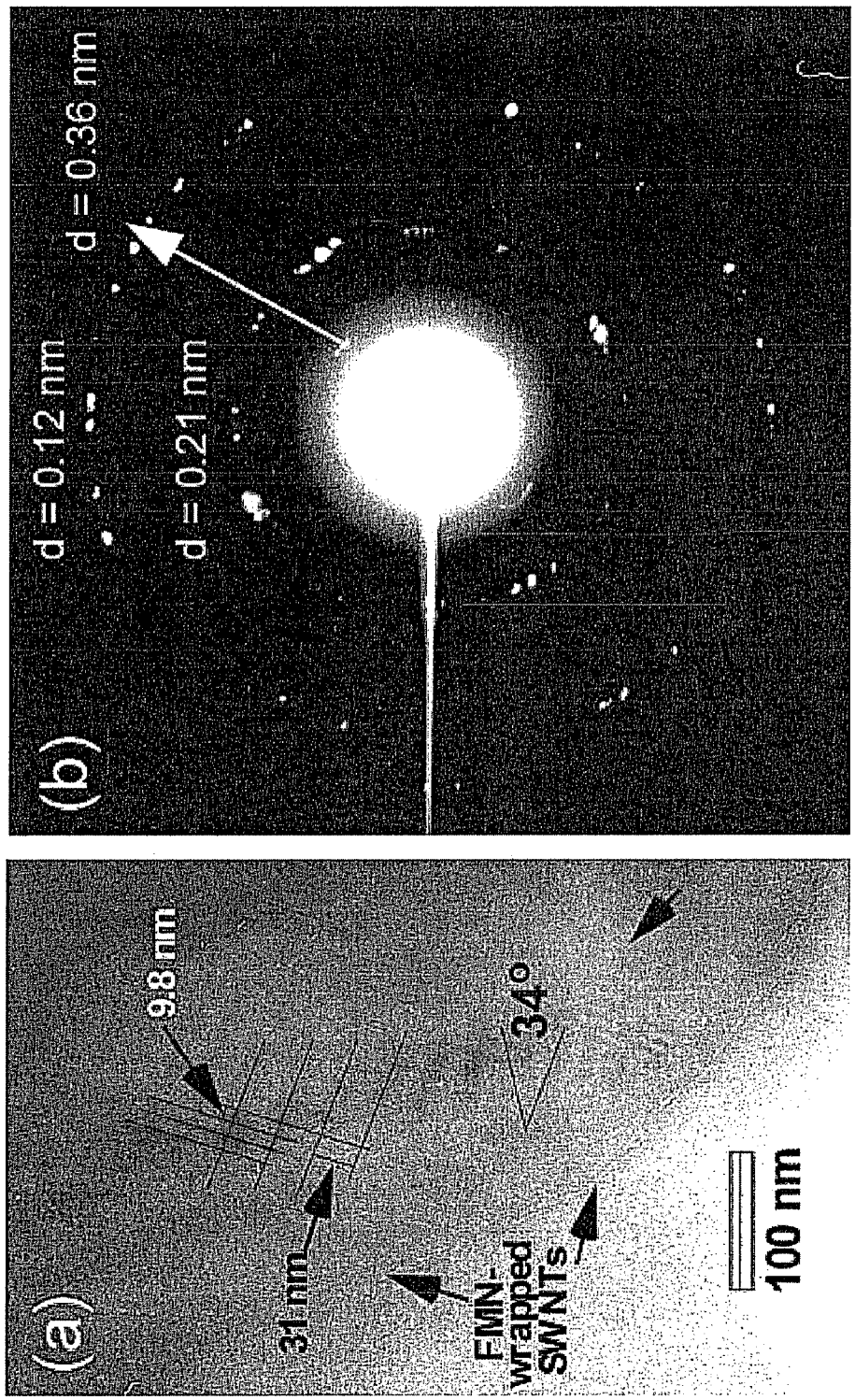
FIG. 18(a) depicts TEM image of lyophilized FMN/HiPco-SWNT mixture. The observed periodicity conforms to 9.8 and 31 nm with a skew angle at 34°.
FIG. 18(b) shows the selected area electron diffraction pattern of FIG. 18(a)

FIG. 18(a) depicts a TEM image of one of the lyophilized FMN/HiPco-SWNT composite domains. The arrows indicate the distinct presence of individualized SWNTs that are near a crystalline domain (FIG. 18(a)), which exhibits distinct periodic fringes. The excess of FMN into the FMN/HiPco-SWNT centrifuged mixture (ca. 30/1 w/w) suggests that such domains are mainly constituted by FMN. From FIGS. 17 and 18, it appears that the aforementioned wrapping of the FMN around the SWNTs (FIGS. 15 & 16) nucleates the crystallization of FMN, that otherwise do not occur even in highly purified FMN samples. Based on the helical wrapping pattern of the FMN around the SWNT, one can expect that such macroscopic crystallites would also exhibit a helical pitch. It is believed that such helical pitch provides periodic fluctuations of the refractive index within these crystalline domains, which can explain the periodic appearance of fringes in FIG. 18(a).

Figure 19:
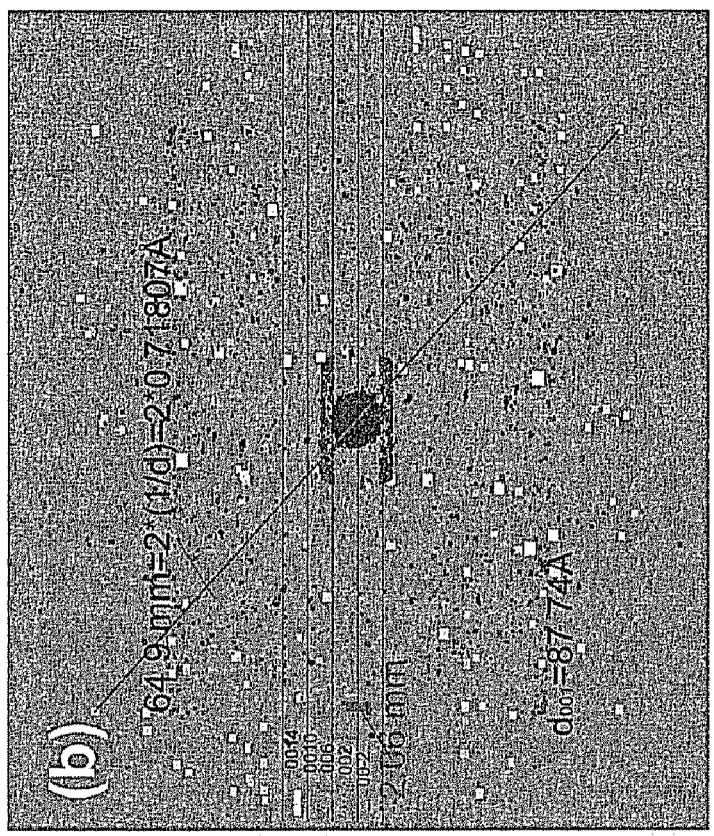
FIG. 19 is a reconstructed 3D X-ray diffraction pattern of an annealed FMN/HiPco-SWNT composite based on multiple 2D X-ray diffraction patterns.
Figure 19:
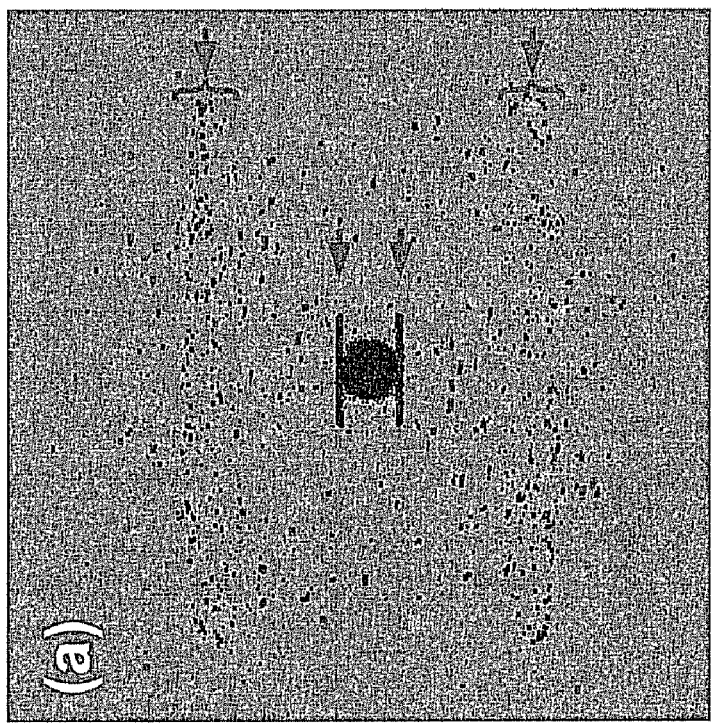

The order in the macroscopic fibers of these lyophilized samples can be increased by subjecting them to a humidity (ca. 85%) controlled chamber for a period of two days. FIGS. 19(a) and (b) illustrates a 2D projection of the 3D X-ray diffraction pattern. In excess of 1000 diffraction spots are evident from this pattern, indicative of high order of crystallinity. This pattern is a composite of multiple single-crystal domains with a preferred orientation. The presence of four well-defined circular collections of diffraction spots (whose line projections are indicated with arrows in FIG. 19(a) are oriented perpendicular to the fiber axis direction of the FMN/HiPco-SWNT lyophilized and annealed composite. A closer inspection of the equatorial region indicates the presence of a large number of diffraction spots (some of which have relatively large intensity). These equatorial reflections obey fiber-pattern 001 groupings. What is most surprisingly is some of the 001 spacings are in excess of 11 nm and some times extend as much as 25 nm. Such large repeat periods are reminiscent of the repeat distances observed in the FIG. 18. In addition, the crystallite propagation forms a 34 degree angle with the 31 nm spaced fringes, which is close resemblance with the 34-37 degree helical pitch of the FIG. 18. This implies that FMN crystallization is nucleated from the ordered FMN helix, wrapped around the SWNT. Such FMN/SWNT helix is expected to exhibit variations in pitch, as part of helicity variation between different SWNT species. This indicates the co-crystallization between SWNT and another moiety (i.e. FMN), which is believed to originate with the following three steps:

i.) Absorbance of crystallizable moiety (i.e. FMN) onto SWNTs ii.) Organization of such moiety into an ordered structure (i.e. helix in the case of FMN)

iii.) Nucleation and crystallization propagation of the crystallizable moiety on top of the ordered SWNT/moiety nuclei (i.e. FMN helices onto SWNTs)

Figure 3:
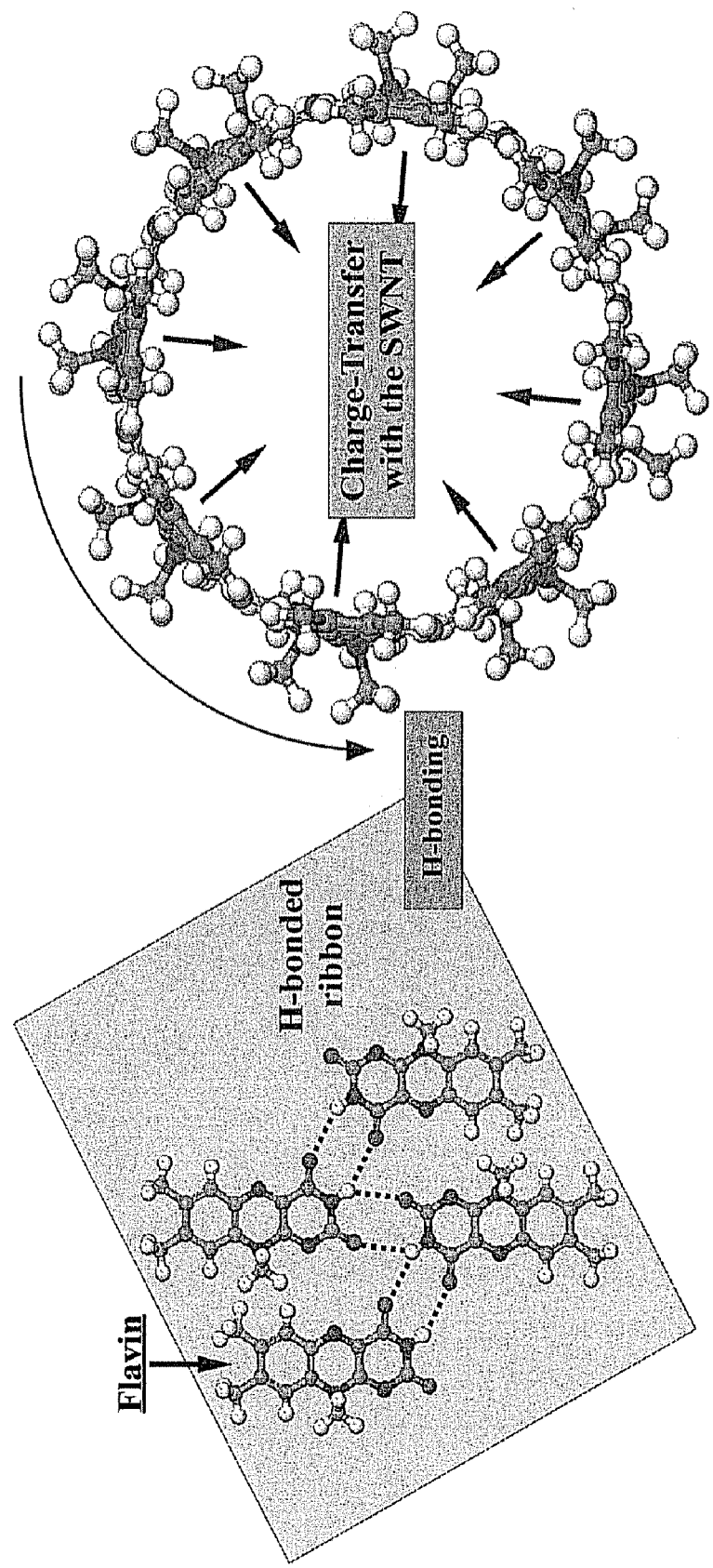
FIG. 3 is an exemplary depiction showing tight helical wrapping of the carbon nanotubes by a flavin mononucleotide using quadruple hydrogen bonding and concentric charge-transfer.

Based on the above results it appears that FMN forms a tight helical wrapping on the sidewall of SWNT, as shown in FIG. 3. Without being limited by theory, such wrapping is produced in two steps—i) the isoalloxazine ring physisorbs onto the side walls of SWNTs, and ii) the formation of four hydrogen-bonds between adjacent uracil moieties of the flavin moieties initiate the organization of the physisorbed isoalloxazine rings into a tight helical wrapping of an FMN based ribbon. This FMN ribbon (with a width of two flavin moieties) results in a helical arrangement of the d-ribityl phosphate FMN-side chains, which provides an ordered helical structure for subsequent crystallization of the free FMN. Since such FMN crystallites nucleate from FMN/SWNT composite helices, they also show comparable helical periodicity.

Example 9

Diameter Selectivity Model and Prediction of Diameter Enrichment

Figure 20:
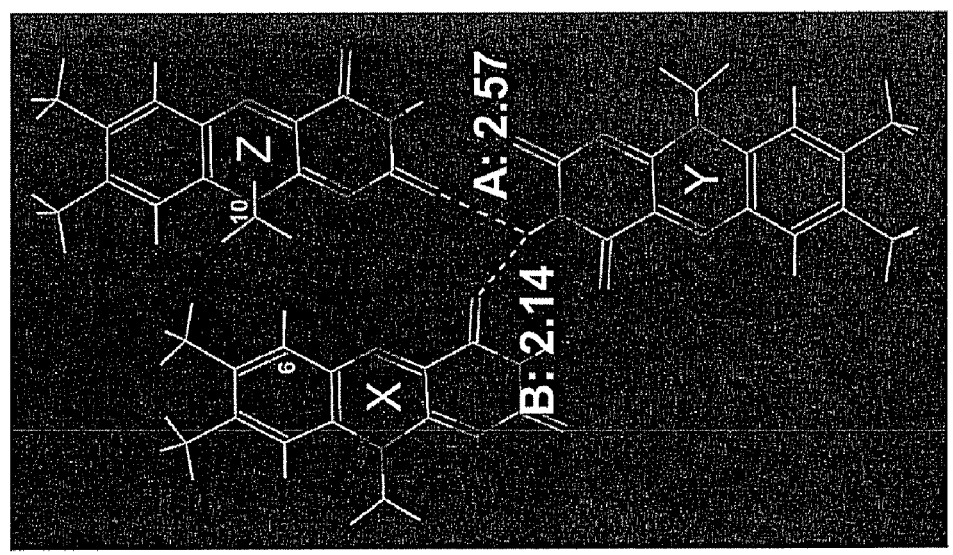
FIG. 20 indicates a mechanism of H-bonding-mediated diameter separation of the SWNT as afforded by FMN.
Figure 21:
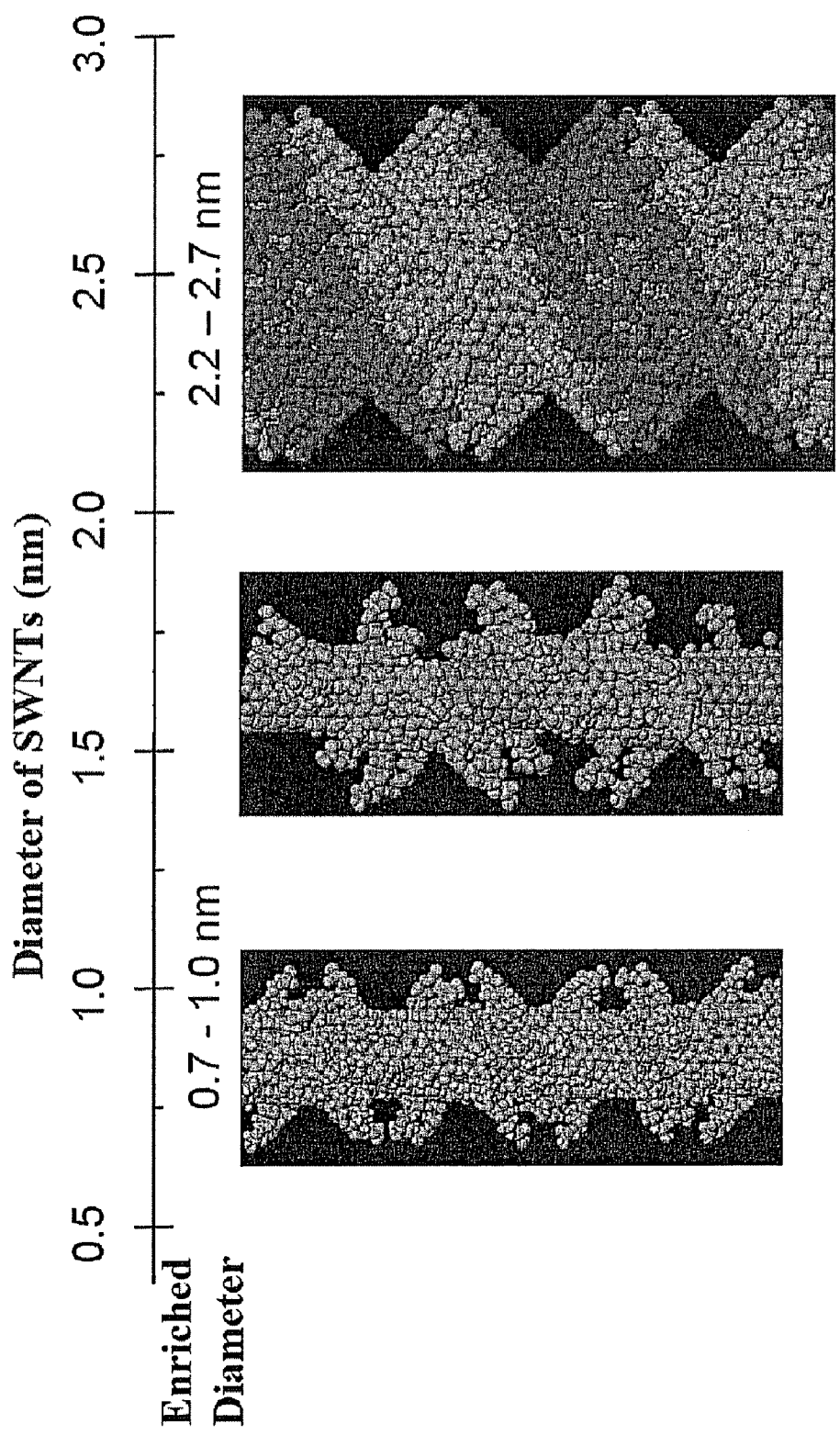
FIG. 21 shows diameter selective enrichment based on the formation of tight helical wrapping of FMN on the side-walls of SWNT. Light- and dark-shaded structures denote H-bonded FMN ribbons, wrapped around the side-walls of SWNTs. As the diameter ($d_t$) of the nanotubes increases, the single FMN ribbon is unable to efficiently cover nanotubes with a diameter between 1.1 and 2.1 nm. For nanotubes with $d_t$ between 2.2 to 2.7 nm, a two ribbon wrapping pattern occurs.

FIG. 20 illustrates a representative flavin trimer organized on the side-walls of a 0.92 nm diameter SWNT. The hydrogen (H)-bonding distances A and B are important for the formation of the tight FMN helix around the nanotube. Curvature is directly related to the close contact between the 10-H and the 6 methyl of the X and Z isoalloxazine rings, respectively. The higher the curvature between the X and Z isoalloxazine rings, the closer they can come. To a first approximation, the Z and Y isoalloxazine rings are almost planar forming a dimmer that is oriented along the long axis of SWNT. The strength of the A H-bond in the YZ pair is on average stronger than that of the B hydrogen-bond (sometimes referred to as a H-bond) in the XY pair. As the diameter of the nanotube increases, the more planar the X and Z rings get, which pushes them further apart, thereby increasing the length of the B hydrogen-bond. This explains how SWNTs with diameter ranging from 0.7-1.02 nm can be accommodated within these helical ribbons. Such $d_t$ enrichment is based on one helical ribbon wrapping along the side walls of SWNTs. For larger diameters (i.e., $d_t$ varying from 1.1 to 2.1 nm) such wrapping exposes certain percentage of SWNT side-walls as shown in FIG. 21. For nanotubes with $d_t$ between 2.2 to 2.7 nm, a two ribbon wrapping pattern is allowed. Preliminary results indicate that certain fraction of the H-SWNT sample is wrapped with double FMN ribbon according to the aforementioned prediction. Such double ribbon wrapping is expected to play a crucial role for diameter enrichment of double walled nanotubes (DWNTs). The similar chirality, metallicity and handedness (vide infra) enrichment patterns are expected to be obeyed with these double ribbon wrapped DWNTs as with those of SWNTs.

Example 10

Determining of Binding Strength of the FMN Helix to Different (n,m) Chirality Nanotubes This experiment demonstrates a PLE titration of FMN-wrapped SWNTs as a function of increasing SDBS (sodium dodecyl benzyl sulfate) surfactant concentration. SDBS is capable of disrupting the FMN helix and wrapping itself around nanotubes at above the SDBS CMC critical micelle concentration, which is about $10^{-4}$ M. The FMN helix disruption and replacement with an SDBS elongated micelle uses a larger quantity of SDBS (about 10 times more). When this happens, a PLE blueshift takes place. This PLE transition is very distinct and can be followed for nearly every nanotube.

FIG. 22(A)-(D) illustrates the PLE transition explicitly for the (8,6)-SWNT. By plotting this redshift vs. concentration of SDBS, one can see a well-defined step transition (FIG. 22(E)-(G)) than can be used to express the FMN-binding strength in terms of SDBS concentration. A closer look of FIGS. 22(E)-(G) indicates that the FMN helix on the (8,6) nanotube is twice as strong as in the (9,4) and the (8,3) nanotubes. More interestingly, the (8,6) FMN-wrapped nanotube appears to have the least PLE quenching. FIG. 22(G) illustrates the percent quenching of nearly all-visible SWNTs. A profound zigzag pattern in the percent quenching is witnessed as one progresses from small to high chiral angle nanotubes.

PL quench variation with a zig-zag pattern is much more affected by nanotubes with higher chiral angles within the same family. In addition, if the sum of n and m form an (n,m) index that is odd, PL quenching of the SWNTs is much stronger than that of the SWNTs that have an even index. Nanotubes having the highest chiral angle also have modality dependence. Generally speaking, a nanotube having a modality (Mod) equal to 1 tends to fortify the PL quench of the nanotube for near armchair types of nanotubes. SWNT with Mod=2 shows the smallest PL quenching among the same family members.

This provides a first indication that the helical wrapping of FMN around SWNTs might exhibit epitaxial ordering. Without being limited by theory, this wrapping is quite sensitive to the underlying nanotube helix and corrugation could take place at each other's surface. This is believed to affect PL quenching of the nanotube by family and by modality. The earlier mentioned family-dependent PL redshift can be thought of as a continuum of this organization-derived corrugation matching.

Figure 22:
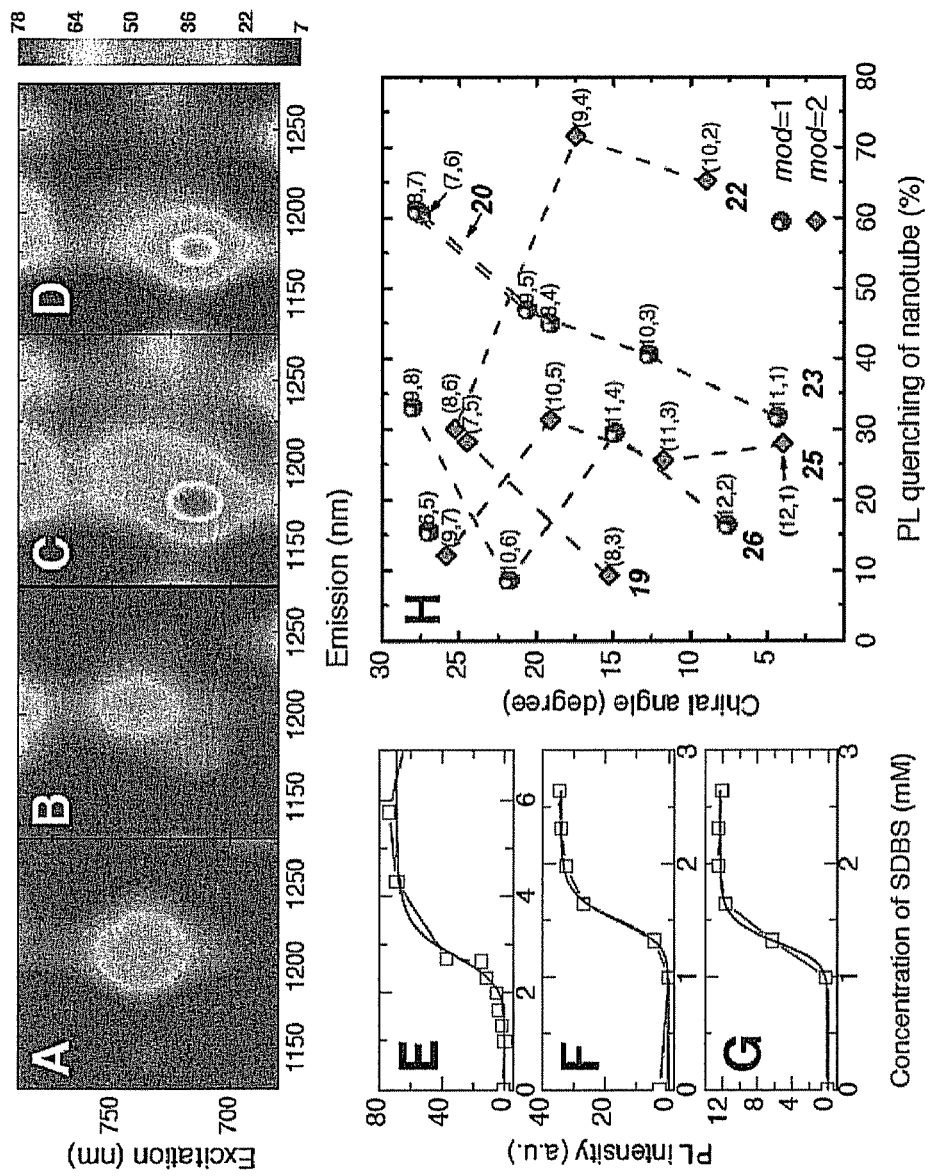
FIG. 22 shows SDBS titration in FMN-wrapped HiPco dispersion. (A-D) Photoluminescence emission (PLE) maps of (8,6) nanotube in various SDBS concentration of 0 mM (A), 2.3 mM (B), 4.3 mM (C), and 7.4 mM (D). (E-G) PLE intensity profile of FMN-wrapped nanotube dispersion against SDBS concentration titration, obtained from (8,6) (E), (9,4) (F) and (8,3) (G), respectively. Please note that for graph (E) the concentration of SDBS at the inflection point is double that of (F) and (G). (H) Plot of chiral angle against percent PL quenching of given (n,m) nanotubes. Blue circle and red diamond denote the modality (mod(n−m,3)=1 or 2), respectively. Bold italics indicate nanotube family (2n+m=ct) and grey broken lines were drawn to guide the eye on the nanotubes in the same family. Please note that while progressing from small to high chiral angle nanotubes within the same family, a characteristic zigzag pattern in the percent quenching is witnessed, indicative of communication of the SWNT with the FMN helix.

The sharp sigmoidal onset shown in FIG. 22 (E)-(G) varies from nanotube to nanotube. Without being limited by theory, the relative FMN-wrapping affinity ($K_a$) against SDBS replacement has been derived using the Hill equation (fitted curve in FIG. 22 (E)-(G) and expressed in terms of the SDBS concentration (expressed in mM) in Table 1. Table 1 shows tabulated PLE intensities from the SDBS PL position of various (n,m) nanotubes, as a function of the SDBS addition in FMN-wrapped nanotubes. The relative affinity ($K_a$) of FMN-SWNT wrapping against SDBS concentration and fitted Hill coefficient ($\tilde{a}$) are also presented.

TABLE 1

| Assignment | Diameter | Chiral Angle | Measured point | | SDBS concentration (mM) | | | | | | | | | |
|---|---|---|---|---|---|---|---|---|---|---|---|---|---|---|
| (n, m) | nm | degrees | $E^s_{11}$ | $E^s_{22}$ | 0 | 0.66 | 0.99 | 1.32 | 1.65 | 1.98 | 2.31 | 2.65 | $K_a$ | γ |
| (6, 5) | 0.76 | 27 | 974 | 568 | 2290 | 2480 | 2180 | 4120 | 5590 | 6070 | 6290 | 6270 | 1.35 | 9.0 ± 1.7 |
| (8, 3) | 0.78 | 15.3 | 954 | 664 | 1230 | 1120 | 961 | 7210 | 12600 | 13300 | 13700 | 13700 | 1.33 | 12.1 ± 1.5 |
| (7, 5) | 0.83 | 24.5 | 1029 | 646 | 4300 | 2710 | 2600 | 9540 | 9360 | 10300 | 9550 | 10100 | 1.2 | 11.8 ± 7.3 |
| (8, 4) | 0.84 | 19.1 | 1116 | 589 | 3690 | 3060 | 2440 | 5800 | 16300 | 21500 | 22700 | 23800 | 1.56 | 9.7 ± 1.2 |
| (7, 6) | 0.89 | 8.9 | 1119 | 646 | 4820 | 3270 | 3140 | 4750 | 9540 | 11400 | 12500 | 12700 | 1.67 | 5.7 ± 2.4 |
| (11, 1) | 0.92 | 27.5 | 1263 | 610 | 5530 | 5250 | 4970 | 6410 | 7560 | 7920 | 8180 | 8900 | 1.51 | 4.8 ± 1.9 |
| (9, 4) | 0.92 | 17.5 | 1107 | 721 | 4680 | 2880 | 2110 | 6340 | 29100 | 34700 | 36400 | 37100 | 1.51 | 13.8 ± 1.9 |
| (10, 3) | 0.94 | 25.3 | 1251 | 631 | 6330 | 5810 | 5620 | 13400 | 16700 | 17700 | 18600 | 18800 | 1.28 | 9.6 ± 2.4 |
| (8, 6) | 0.97 | 20.6 | 1179 | 715 | 8170 | 7380 | 7410 | 8980 | 11400 | 12600 | 19500 | 22500 | 2.81 | 8.6 ± 3.4 |
| (9, 5) | 0.98 | 4 | 1248 | 670 | 7170 | 6740 | 6440 | 12100 | 27200 | 29600 | 30000 | 30600 | 1.44 | 13.6 ± 0.9 |
| (12, 1) | 0.99 | 12.7 | 1173 | 796 | 5110 | 4570 | 4600 | 12000 | 18600 | 21100 | 23500 | 22800 | 1.4 | 7.5 ± 1.2 |
| (11, 3) | 1.01 | 11.7 | 1194 | 793 | 12100 | 11500 | 10800 | 22300 | 32200 | 32200 | 31200 | 32300 | 1.3 | 16.4 ± 8.2 |
| (8, 7) | 1.03 | 27.8 | 1269 | 727 | 9250 | 8300 | 7480 | 8370 | 10600 | 10800 | 11000 | 11100 | 2.08 | 3.0 ± 5.2 |
| (12, 2) | 1.04 | 7.6 | 1374 | 682 | 3860 | 3670 | 3510 | 4250 | 4670 | 5390 | 5690 | 5880 | 1.69 | 4.6 ± 1.6 |
| (11, 4) | 1.07 | 14.9 | 1371 | 715 | 3830 | 3350 | 3300 | 4810 | 5430 | 6060 | 6370 | 6570 | 1.49 | 5.6 ± 2.1 |

Example 11

Enriching a Single (n,m) Chirality Carbon Nanotube

The aforementioned apparent strength of the FMN helix on the (8,6) SWNT can also be used to selectively enrich this nanotube against all others. Such enrichment can proceed by first titrating with SDBS to cause all other nanotubes to be coated with SDBS, while the (8,6) SWNT remains FMN-wrapped (see FIGS. 22(E)-(G) and Table 1). Since the addition of 2.68 mM SDBS appears to replace FMN in all but (8,6) nanotube, the selective precipitation of SDBS-replaced nanotubes against the still remaining FMN-wrapped (8,6) nanotubes was performed. Addition of 0.5 M NaCl can salt out the SDBS-replaced nanotube and leave the FMN-wrapped (8,6) nanotube in solution.

Figure 23:
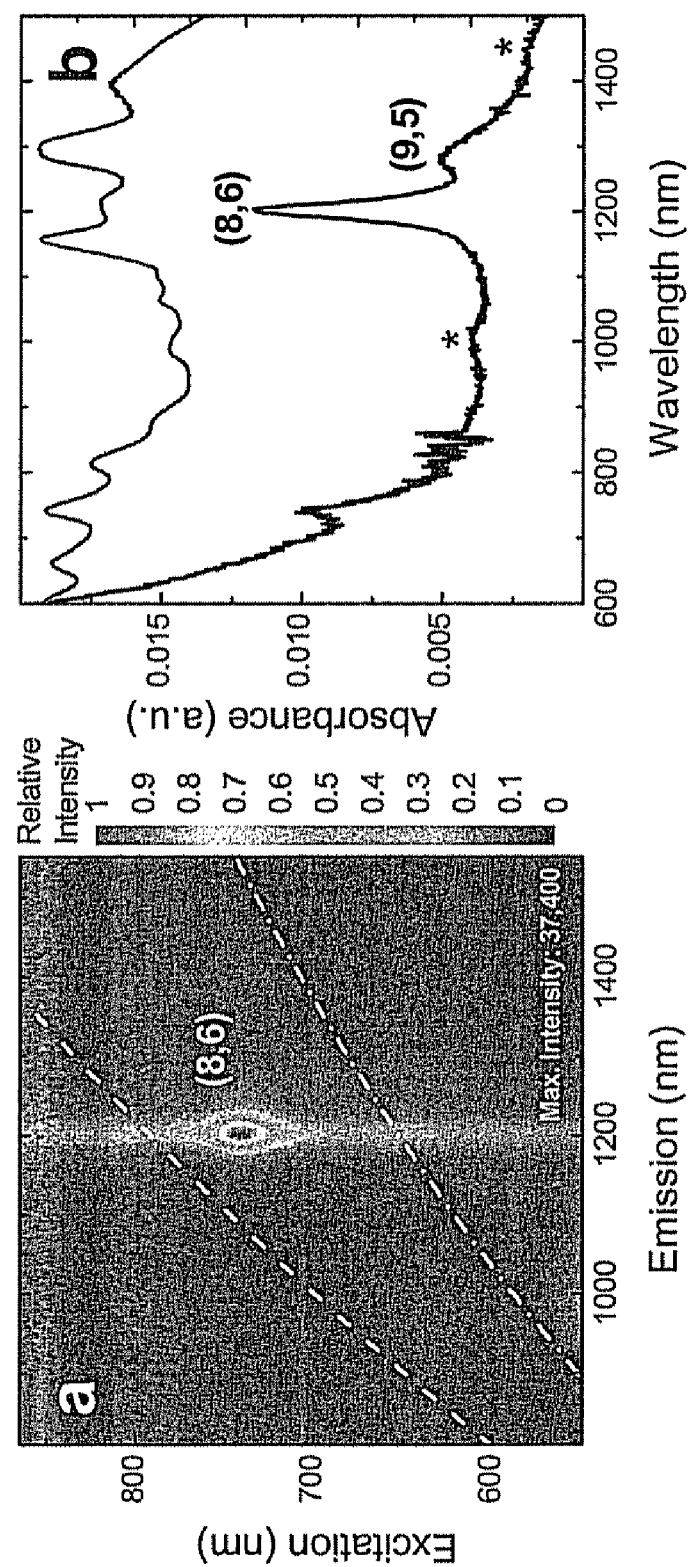
FIG. 23(a) shows enrichment of (8,6) nanotube using selective "salt-out" technique of SDBS-replaced nanotube by NaCl. (A) PLE map of FMN-dispersed (8,6) nanotube. Two white broken lines originate from phonon mode of carbon nanotube. Phonon modes are indicated by broken lines. (b) UV-Vis-NIR spectra of the corresponding salt-out supernatant (bottom spectra), as opposed to initial FMN-dispersed HiPco sample (top spectra). The upper spectra in (b) was multiplied by 0.05 and offset upwards by 0.01 absorbance units, to facilitate visual comparison. The asterisks denote phonon mode absorption of the (8,6)-SWNT.

FIG. 23 shows a PLE map of FMN dispersion of a four times diluted (8,6) enriched carbon nanotube. The residual NaCl in (8,6) enriched nanotube solution cause a redshift of a few meV for the $E_{11}$ of the nanotube. The possibility of a diameter-dependent "saltout" effect on SDS-dispersed nanotube is excluded since it does not show any smaller nanotube. FIG. 23(a) clearly supports that there is no additional (n,m) nanotube. Its purity is calculated to be in the order of 85%, based on photoluminescence and NIR absorption studies.

While the visualization of nanotubes other than (8,6) and its phonon modes is difficult from FIG. 23(a), a baseline close-up indicates that the (9,5) nanotube is also present. The optical absorption of FIG. 23(b) concurs with the profound enrichment of (8,6) at 1203 nm, along with the small presence of (9,5) at 1278 nm. The steep absorption upswing at wavelengths below 800 nm is mostly attributed to the tail-end absorption of FMN (0.1 wt. %), and to a lesser extent from residual scattering of SDBS micelles and the presence of amorphous carbon. While the $K_a$ of (9,5) is significantly less than that of (8,6), the fact that both nanotube species have similar diameters (0.97 and 0.98 nm for (8,6) and (9,5), respectively) suggests that during SDBS/salt flocculation, (9,5) is re-wrapped by FMN, and remains in solution.

Example 12

Separation of the Carbon Nanotubes by Handedness

Figure 24:
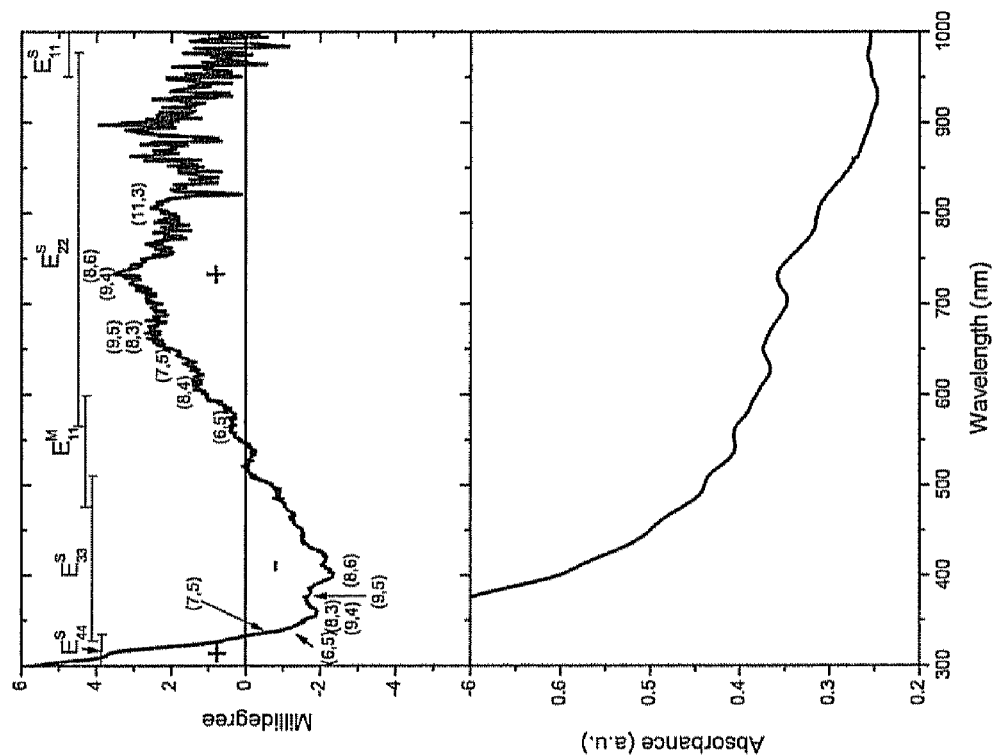
FIG. 24 shows circular dichroism (top) and UV-Vis-NIR (bottom) spectra of an FMN-enriched HiPco SWNT composite sample centrifuged at 15 kg, where the FMN was completely exchanged with SDBS.

The chiral nature of FMN is expected to also impart handedness separation of SWNTs. FIG. 24 illustrates the circular dichroism (top) and UV-Vis-NIR (bottom) spectra of an FMN-enriched HiPco SWNT composite sample centrifuged at 15 kg, where the FMN was completely exchanged with SDBS. Such FMN substitution with the achiral SDBS permits a direct observation of the handedness enrichment patterns on FMN-enriched nanotubes. In addition, the low absorption of SDBS in the 400-600 nm region, allows the direct observation of the $E_{33}^S$ optical absorptions in the UV-Vis spectra. In addition, SDBS can disperse larger diameter ($d_t$) SWNTs than FMN, which has preferential small diameter selectivity. The absence of an absorption peak at the $\lambda_{max}$ of 370 nm and 445 nm in the bottom graph of the FIG. 24 indicates the complete removal of FMN. The corresponding CD spectrum (top) illustrates that FMN can enrich the separation based on one-handedness of SWNTs at 15 kg centrifuge speed. For example, the (9,4) SWNT, which is the major peak in the FIG. 13, exhibit peaks at 360 and 722 nm, which corresponds to $E_{33}^S$ and $E_{22}^S$ of semiconducting SWNTs, respectively, with respective alternative signs of negative and positive in the CD measurements. Other indices show similar alternative signs in $E_{33}$ (negative sign) and $E_{22}$ (positive sign) for the semiconducting SWNT. Based on this observation, the 15 kg centrifuge speed appears to enrich separation based on one of the types of chirality (i.e., the handedness (either D-(right handed) or L-(left handed)) available in SWNTs. Metallic SWNTs on the other hand, whose absorption for HiPco SWNT ranges from 480 to 600 nm appear to cross the zero line (from (−) to (+) sign), albeit that their signal is rather weak as indicated from the FMN-imparted type separation (vide supra).

Figure 25:
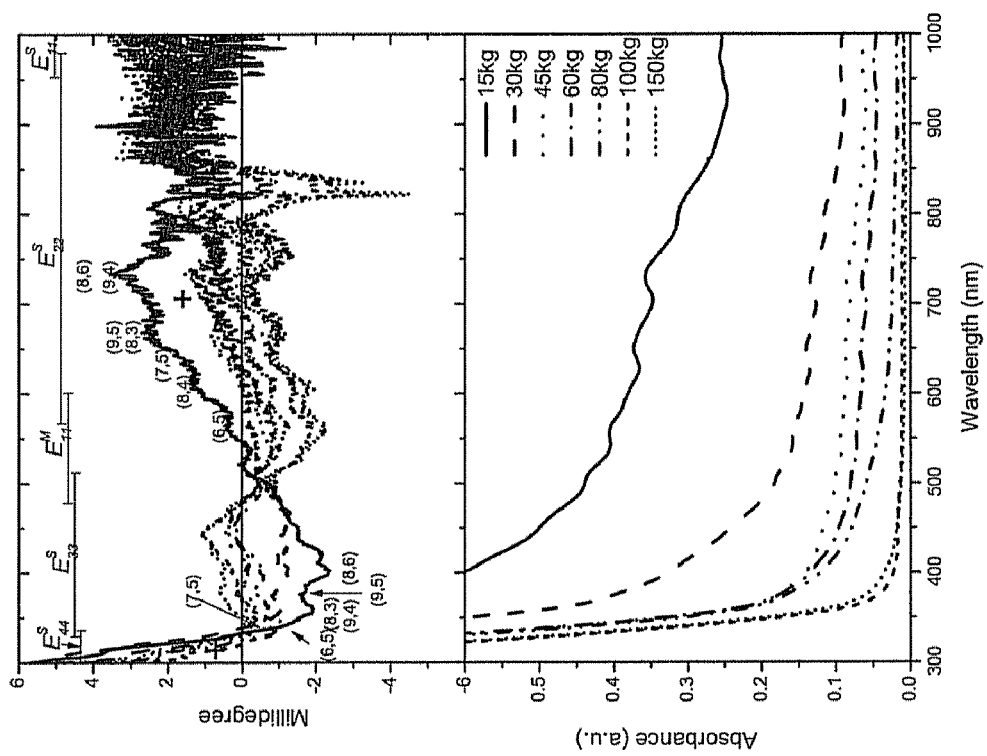
FIG. 25 shows the effect of centrifugation speed on the circular dichroism (top) and UV-Vis-NIR (bottom) spectra of FMN-enriched HiPco SWNT composite sample, where after centrifugation at a given speed, the FMN was completely exchanged with SDBS.

FIG. 25 illustrates the effect of centrifugation speed on the handedness enrichment of FMN/HiPco-SWNTs. As explained in FIG. 24, centrifugation at 15 kg results in a handedness enrichment with negative sign at the $E_{33}^S$ transitions and positive sign at the $E_{22}^S$ transitions. This handedness enrichment appears to reverse at high centrifugal speeds, where a positive and negative signs are observed for the $E_{33}^S$ and $E_{22}^S$ transitions, respectively.

Example 13

Photoreduction of FMN-HiPco Composite in an Aqueous Solution

Flavin moieties can undergo anaerobic photo-reduction in the presence of electron donors such as nicotinamide adenine dinucleotide (NADH), ethylenediamine tetraacetic acid (EDTA), methionine and the ribityl side chain of riboflavin. Light having a wavelength of less than 500 nm can cause rapid photo-reduction. No photo-reduction takes place for wavelengths greater than 550 nm, since the flavin moiety does not absorb in this region. Such photoreduction can facilitate determining conformational changes from the planar FMN moiety to the bended $FMNH_2$ moiety.

Figure 26:
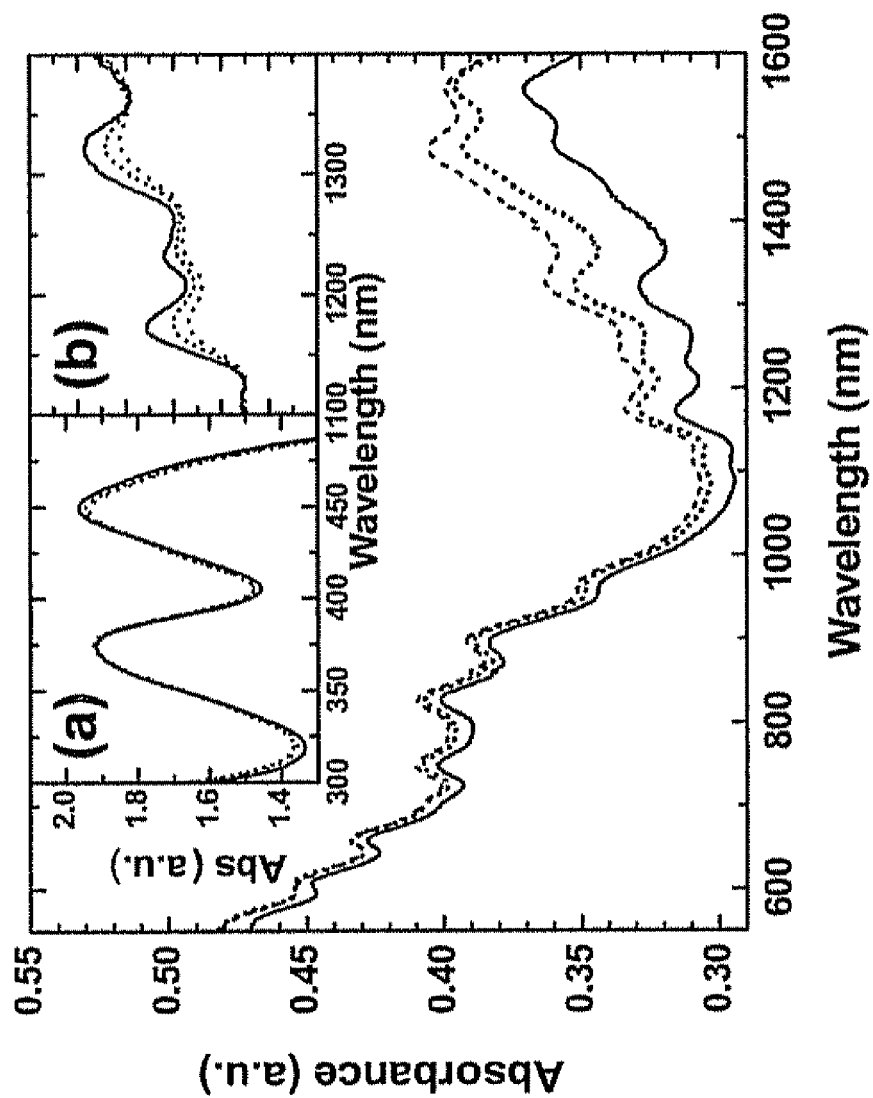
FIG. 26 shows the UV-VIS-NIR spectra of FMN-wrapped HiPco SWNT $D_2O$ suspension before (solid curve) and after irradiation at 365 nm for 10 minutes (dotted curve) in the absence of O2. The dashed curve is the corresponding UV-VIS-NIR spectrum after O2 bubbling. Insets (a) and (b) illustrate a blow up of the background normalized UV-Vis and NIR regions.

Since carbon nanotubes behave as efficient redox mediators, the photoreduction effects of FMN on SWNTs was also investigated. For this, 15 kg centrifuged FMN/HiPco-SWNT composite in an aqueous solution was purged with argon for 1 hr to remove any dissolved $O_2$. FIG. 26 illustrates the UV-VIS-NIR spectra of the initial FMN/HiPco-SWNT sample (solid curve) after 10 minutes of irradiation with light having a wavelength of 365 nm to produce the first curve (dotted curve). Following spectroscopic investigation, air was introduced to produce the second curve (dotted-dashed curve). The insets in FIG. 26 illustrate the enlarged portions of FMN absorption (top-left, a) and normalized $E_{11}^S$ region (top-right, b).

Prior to irradiation, the first absorption peak of FMN is located at 449 nm, which is ca. 4 nm redshifted from the pure $10^{-5}$ M aqueous FMN solution (data not shown). The first ($E_{11}^S$, 600-950 nm) and second ($E_{22}^S$, 950-1600 nm) optical transition energies of semiconducting SWNT can be witnessed at the initial spectra, prior to irradiation. As detailed above, the $E_{22}^M$ of metallic SWNT (ranging from 480 to 600 nm) overlaps with the absorption of FMN and cannot be seen in this spectra. Upon 10 minutes of irradiation with a 365 nm hand-held UV lamp, a slight decrease in FMN absorption (at 449 nm) can be observed from FIG. 26(a). A more pronounced change takes place though with the optical absorption of SWNTs. First, a background increase is witnessed to the overall absorption range of SWNTs (from 650 to 1600 nm). Such a background increase is believed to originate from the formation of a new charge-transfer species, whose absorption is expected to be significantly broader than individual (n,m) $E_{11}^S$ and $E_{22}^S$ transitions.

Similar observations were made when DNA-wrapped SWNTs in $AgNO_3$ solution were illuminated. The formation of Ag nanoparticles formed charge transfer species with the SWNTs. The broader background absorption was also accompanied with the decrease in peak height of the $E_{11}^S$ transition of an enriched (6,5)-SWNT. A similar decrease in the $E_{11}^S$ and $E_{22}^S$ absorptions of FMN/HiPco-SWNT composite peaks can be witnessed in the normalized spectra of FIG. 26(b). The decrease in the $E_{11}^S$ and $E_{22}^S$ absorptions indicates that the SWNT donates electrons to the excited FMN, thereby p-doping itself, which bleaches its optical transitions. The electrons donated to the excited FMN in turn reduce the FMN to either a FMNH radical (FMNH.) or to $FMNH_2$.

Upon the addition of $O_2$, the aforementioned absorptions and overall background recovers partially, as indicated in FIG. 26. This is attributed to re-oxidation of FMNH. or $FMNH_2$ species. This leads to a reversible or quasi-reversible electron transfer (in anaerobic conditions) that is reversed upon exposure to air. The initial decrease of absorption peaks at 370 and 499 nm can be assigned to the depletion of FMN moiety that reacts with protons and electrons to yield the non-luminescent $FMNH_2$ compound. These $FMNH_2$ can quickly equilibrate with excess amounts of FMN to produce FMNH. radicals. At the same time, electrons extracted from SWNT result in the bleaching of peaks displayed by the SWNT. The introduction of $O_2$ re-oxidizes $FMNH_2$ to FMN, which produces $H_2O_2$. This $H_2O_2$ reacts with oxidized SWNT ($SWNT^{n+}$) to produce reduced SWNT, as well as proton and oxygen. Riboflavin, which is devoid of phosphate group of FMN, is known to generate as high as 700 mV, when a cell is illuminated. This indicates that FMN-wrapped SWNT composite can be employed in solar energy conversion schemes, where the SWNTs act as nanoscopic electrical conduits. In addition, FMN-wrapped SWNTs can find application in optical limiting materials and a variety of other electro-optic applications.

Figure 27:
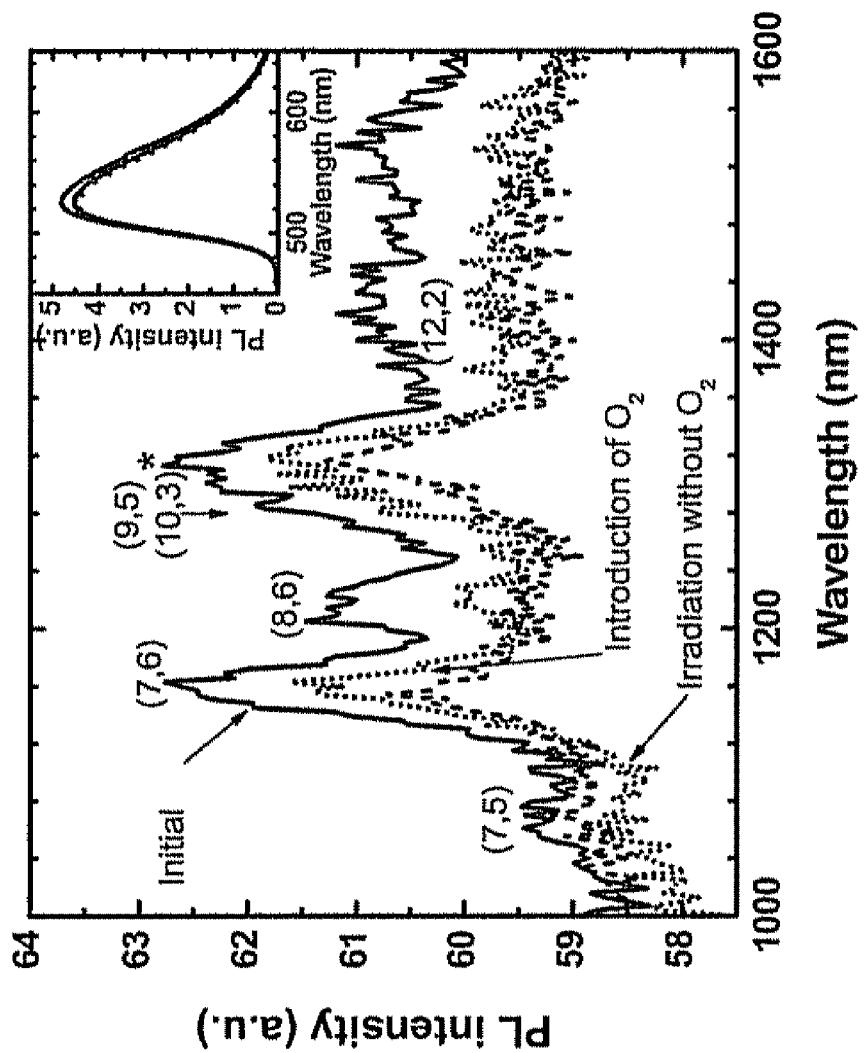
FIG. 27 shows a photoluminescence (PL) spectrum of E11S transitions of FMN/HiPco SWNTs prior irradiation (solid curve) after 365 nm irradiation for 10 min. in the absence of O2 (dotted curve) and after reintroduction of $O_2$ (dashed curve) (the excitation wavelength was 660 nm). The marked asterisk indicates the second fundamental peak of the 660 nm excitation wavelength, which explains the strong, yet symmetric, 1320 nm peak. Inset depicts the corresponding PL spectra of the FMN moiety, excited at 350 nm.

FIG. 27 illustrates the change of photoluminescence (PL) intensity of the $E_{11}^S$ transitions of FMN/HiPco-SWNT composites and FMN moiety (inset) upon 10 minutes of irradiation at 365 nm in the absence of $O_2$. In agreement with the UV-Vis-NIR study, the photoreduction of FMN is accompanied with the oxidation of SWNTs, which lowers their $E_{11}{}^S$PL intensity. The (n,m) peak assignment was based according to FIG. 7(d). The decrease in (7,6) and (7,5) SWNT PL intensity (upon irradiation) appears to be less pronounced than that of (8,6), (9,5), (10,3) and (12,2) nanotubes.

The marked asterisk indicates the second fundamental peak of the 660 nm excitation wavelength, which explains the strong, yet symmetric, 1320 nm peak. The partial recovery of PL intensity by the introduction of oxygen appears to also show (n,m) dependence. Such partial recovery appears more pronounced for the (7,5) and (7,6) nanotubes and less for the (8,6), (9,5), (10,3) and (12,2) nanotubes peak from noise level. This supports a diameter-dependent chirality bleaching of SWNT, produced by photoreduction of FMN.

Figure 28:
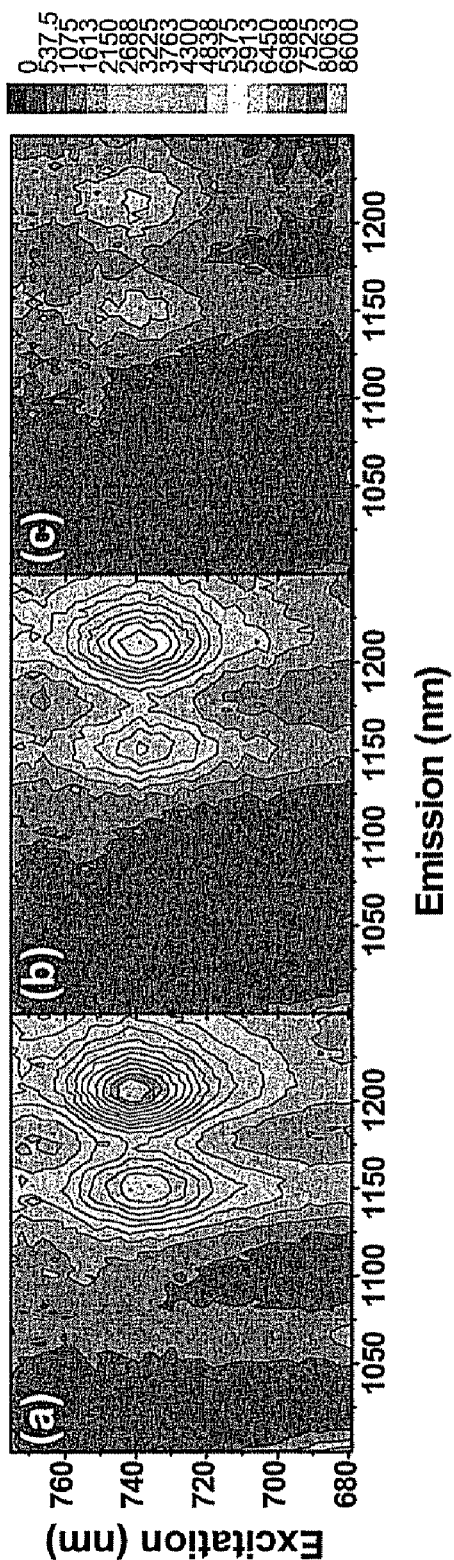
FIG. 28 shows PLE maps of (9,4) and (8,4) SWNTs with different UV irradiation times of (a) initial sample, (b) and (c) after 20 and 80 second irradiations with 365 nm UV, respectively.

Attempts were made to obtain photoluminescence excitation (PLE) maps for such photobleaching by varying the length of the experiments compared with the re-introduction of oxygen within the present experimental set up, which was on in the order of 10 hrs. In order to minimize such $O_2$ re-introduction, a partial PLE map was obtained that required collection time of only 2 hours. FIG. 28 illustrates the PLE maps of (9,4) and (8,6) SWNTs as a function of irradiation time.

Longer irradiation resulted in quenching of (9,4) and (8,6) nanotubes. Both these nanotubes are of the same 2n+m family (24) and modality (mod(n−m,3)=2), yet their diameter differs (i.e., (8,6) $d_t$=0.97 and (9,4) $d_t$=0.92) by 0.05 nm. From the PLE map of FIG. 28, after 80 seconds of irradiation, the PL intensity of (8,6) and (9,4) SWNTs decreased by 75% and 62%, respectively. This is in agreement with the aforementioned results and indicates that the larger the diameter the faster is the electron transfer. Such methodology can also be used for diameter separation.

Example 14

Aerobic Irradiation of FMN/SWNT Aqueous Suspensions

Oxygen was first bubbled to the deuterated aqueous FMN-HiPco composite suspension (clear dark yellow solution) prior to the 10 minutes of UV irradiation at 365 nm. Such UV irradiation caused the suspension to flocculate and precipitate. Shaking did not re-suspend the flocculated nanotubes. Following centrifugation, the supernatant was found to contain significantly fewer nanotubes. By subjecting the supernatant to GC-MS spectroscopy, it was found that a significant number of FMN molecules were severed to lumichrome and deuterated-ribityl phosphate acid.

In the presence of nanotubes, however, such photo-cleavage is slightly decelerated due to the aforementioned nanotube assisted FMN photo-reduction. The application of high power long UV or NIR radiation, resonant to specific $E_{22}{}^S$ and $E_{11}{}^S$, respectively, can cause multi-photon nanotube absorption of specific (n,m) nanotube, which would excite specifically its adsorbed FMN and cause selective precipitation of that (n,m) nanotube.

Example 15

Organic Media-Dispersible "Surfactant-Like" Flavin

Organic solvent-soluble individualized single-walled carbon nanotubes (SWNT) dispersion can be used for employing SWNT in electronic devices such as photovoltaics, microelectronics, and the like. However, current dispersion methodologies mainly depend on water-based process using surfactants such as SDBS, DNA, and polymers, which will be an issue for controlling the performance of devices. Even though organic solvents have certain dispersing power with SWNTs, their dispersion capacity is quite limited.

Utilizing the aforementioned strong concentric π-π interaction and H-bonding capability of FMN, an oil-dispersant analogue containing a dodecyl aliphatic side-group (FC12) was synthesized, as shown in FIG. 5. The synthesis involves two steps with an overall yield of ca. 35%. FC12 dispersions of CoMoCAT SWNTs were obtained by sonicating 1 mg of FC12, 1 mg of nanotubes and 4 mL of various solvents for 4 hour at 300 W. The mixture was subsequently centrifuged for 20 minutes at 10,000 g centrifugation speed, which readily eliminates visible nanotube bundles at various solvents (i.e., benzene, toluene, o-xylene, ethylacetate, tetrahydrofuran (THF), pyridine, acetone, and N,N-dimethyl formamide (DMF)). Table 2 summarizes the physical properties of these solvents as a function of dielectric constant ($\in$). SWNT photoluminescence was observed for only few solvents (i.e., benzene, toluene, o-xylene, ethylacetate, THF and acetone). Table 2 also shows the quantum yield values for (6,5)-SWNTs as a function of solvent dielectric constant ($\in$), H-bonding nature, and solubility values for FC12 and lumiflavin.

TABLE 2

| solvent | PL activity | QY of (6,5)-SWNTs (%) | | $\in$ | H-bonding capability* | Lumiflavin solubility (μg/mL) | FC12 solubility (mg/mL) | Max. $E^s{}_{11}$ Abs. |
|---|---|---|---|---|---|---|---|---|
| | | "Sample" | "Individual" | | | | | |
| benzene | Yes | 5 | 10 | 2.3 | P | 4.4 | 0.31 | 0.01 |
| toluene | Yes | 11 | 20 | 2.4 | P | 4.3 | 0.23 | 0.03 |
| o-xylene | Yes | 8.7 | 16.9 | 2.5 | P | 5.9 | 0.25 | 0.02 |
| ethylacetate | Yes | 0.024 | 0.4 | 6 | M | 14.1 | 0.51 | 0.075 |
| THF | Yes | 0.07 | 0.1 | 7 | M | 46.2 | 11.03 | 0.21 |
| pyridine | No | — | — | 12.5 | M-S | 528.7 | 70.38 | 0.3 |
| acetone | Yes | 0.08 | 0.2 | 21 | M | 53.9 | 1.81 | 0.14 |
| DMF | No | — | — | 39 | M-S | 316.7 | 22.87 | 0.7 |
| $D_2O$† | Yes | 0.08 | 0.8 | 79 | S | — | — | 0.19 |

*P: Poor, M: moderate, and M-S: moderate-strong

FIG. 29(a)-(d) illustrates the PLE maps for benzene, toluene, ethylacetate and acetone. Interestingly, the PL intensity (315,000 counts) of FC12/(6,5)-nanotube in toluene dispersion shows a 15 to 20 times higher intensity than those in other solvents. (see maximum intensity in the bottom of FIG. 29(a)-(d)). In all PLE maps, the observed $E^S{}_{11}$ and $E^S{}_{22}$ transitions are similarly redshifted as in the case of flavin mononucleotide (FMN). The similar $E^S{}_{11}$ and $E^S{}_{22}$ red-shifts trend in organic solvents, as in the case of FMN in $H_2O$ (i.e., 15 to 51 nm for $E^S_{11}$ and 23 to 71 nm for $E^S_{22}$) provide a direct evidence of a helical flavin assembly around SWNTs.

The average photoluminescence full width at half maximum (FWHM) values of all nanotube species in the low dielectric constant solvents (i.e., 26 and 27 meV for benzene and toluene, respectively) are significantly smaller than those in the high dielectric solvents (i.e., 39 and 45 meV for ethylacetate and acetone, respectively). The larger FWHM and lower PL intensities indicate either large a inhomogeneity in FC12 functionalization and/or greater degree of bundling than that in the benzene and toluene dispersions. Recently, Tan et al. (*Phys. Rev. Lett.* 2007, 99, 137402) reported that nanotube aggregation enhances exciton energy transfer (EET) between SWNTs within bundles, where excitation of large gap tubes induces emission to smaller gap ones. Such spectral features are easily discernable for species with high concentration, as in the case of (6,5) and (7,5) for CoMoCAT SWNTs. The arrows in FIG. 29(*a*)-(*d*) indicate such a EET feature between (6,5) and (7,5) SWNTs. When normalized to the PLE intensity of (7,5)-SWNT, the (6,5)→(7,5) EET feature from the benzene and toluene is 2 or 3 times lower than those seen in ethylacetate and acetone. This provides an initial indication that nanotube individualization in toluene is one of the reasons for the higher PL intensity and narrow FWHM.

Figure 29:
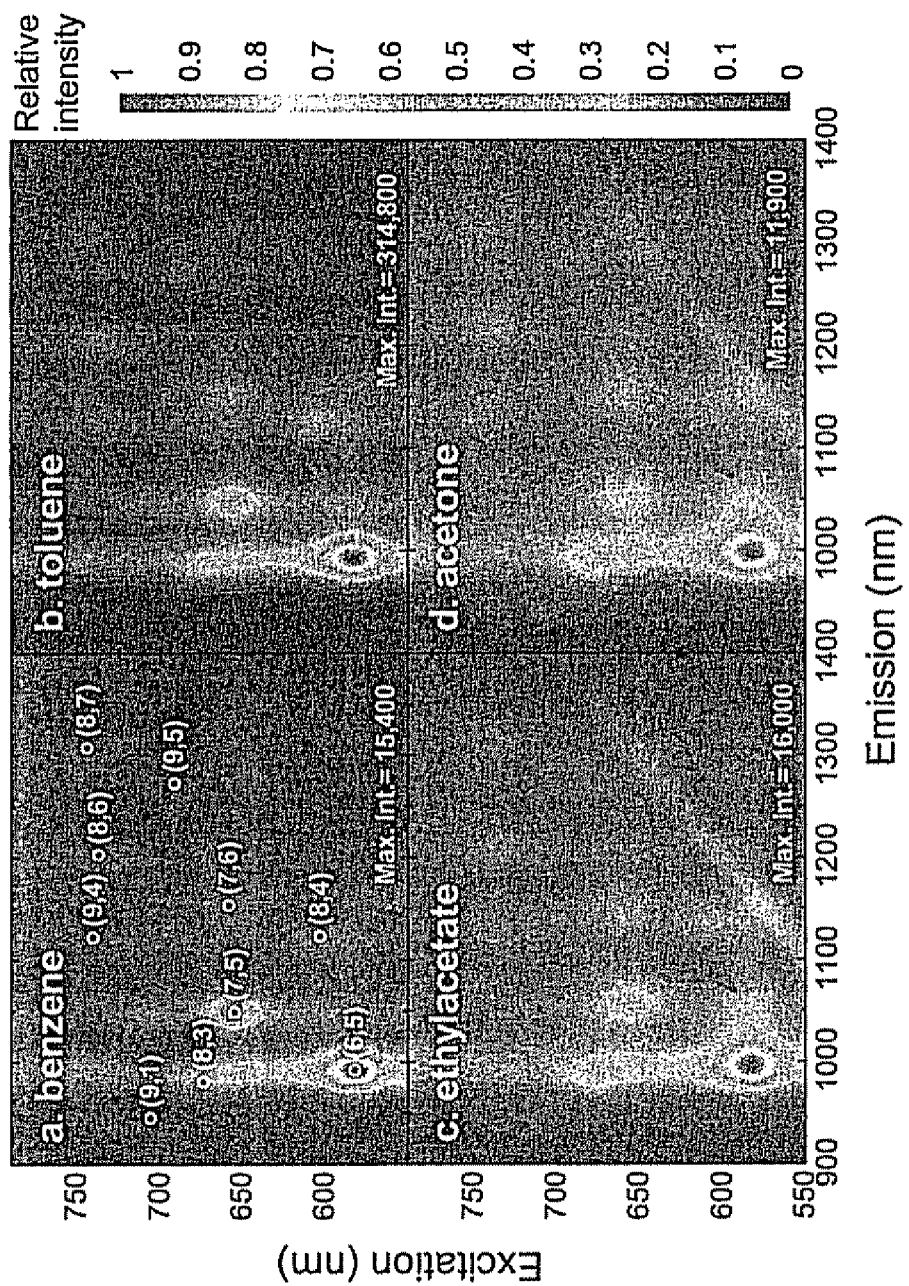
FIG. 29 illustrates solvent-induced differences in the photoluminescence (PL) characteristics and brightness (max. intensity counts) of FC12-dispersed CoMoCAT SWNTs. Numbers in brackets and white circles indicate the (n,m) chiral indices and peak position, respectively, of various SWNT species in (a) benzene, (b) toluene, (c) ethylacetate, and (d) acetone. The toluene FC12/SWNT dispersion shows a maximum PL intensity (314,800 counts). Red arrows depict exciton energy transfer (EET) features from large to small band gap nanotubes.
Figure 30:
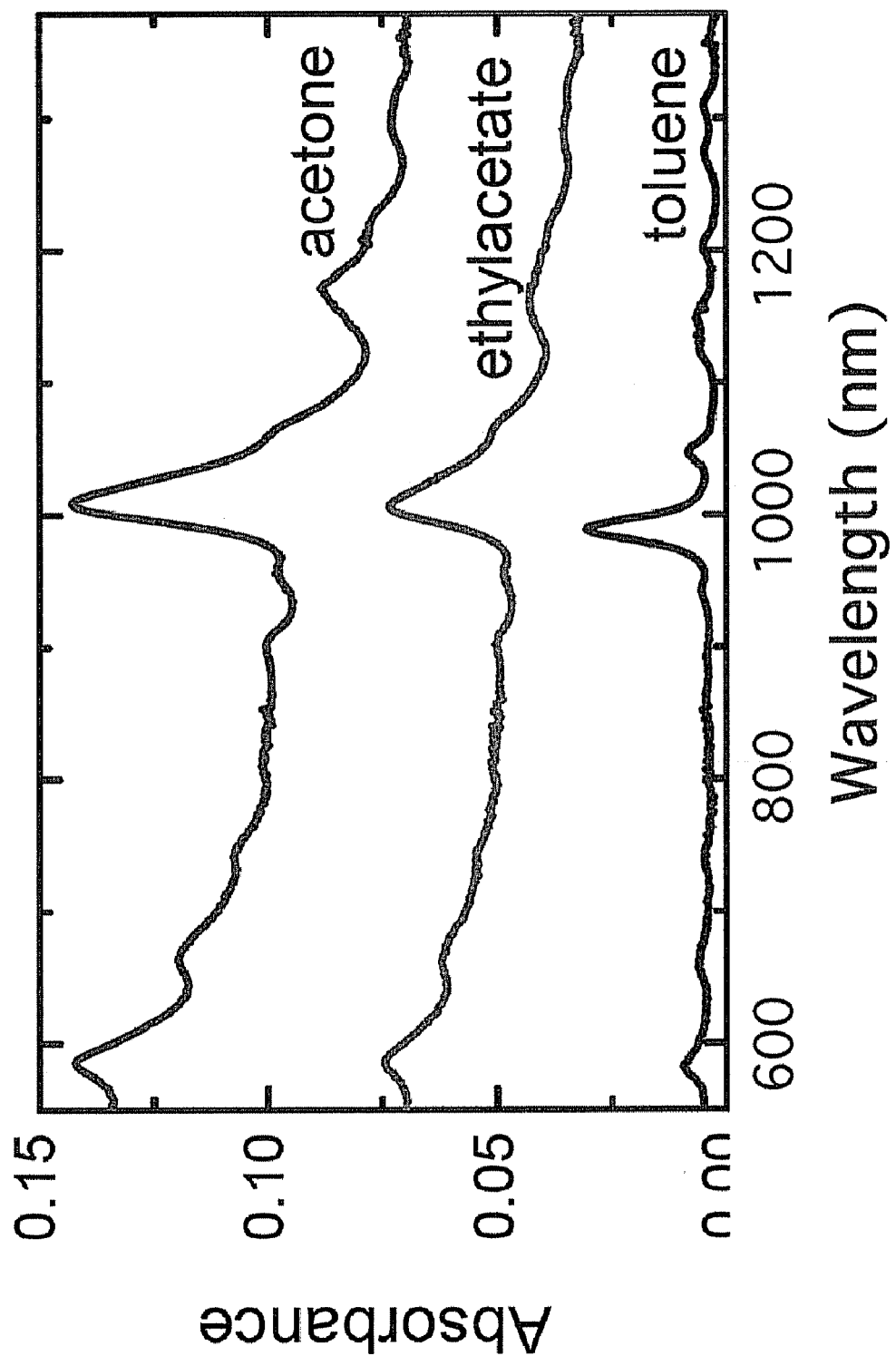
FIG. 30 depicts the Vis-NIR absorption spectra of FC12-dispersed SWNTs in acetone, ethylacetate and toluene. Spectra were not off-set with respect of each other.

FIG. 30 illustrates the corresponding UV-Vis-NIR spectra of FC12-dispersed SWNTs from the samples of FIG. 29(*b*)-(*d*). From a quick comparison, the toluene absorption spectrum exhibits the following striking features: (i) profound peak sharpness, (ii) a nearly flat baseline, and (iii) significant blue shifted absorptions with respect to those of ethylacetate and acetone. Here, it is noteworthy to stress that the three absorption curves in FIG. 30 were not offset with respect to each other, but they rather reside on a power-law background ($a\lambda^{-b}$, where $\lambda$ is the wavelength and a, b are fitted parameters). This power-law background is nearly absent for toluene, and is substantially larger for ethylacetate and acetone. In addition, the $E^S_{11}/E^S_{22}$ ratio (ca. 6) of (6,5) nanotube is the highest reported thus far. Moreover, the (6,5) $E^S_{11}/E^S_{22}$ ratio is ca. 6 only for toluene, and drops to ca. 3.5 and 4 for ethylacetate and acetone FC12-dispersions, respectively.

Figure 31:
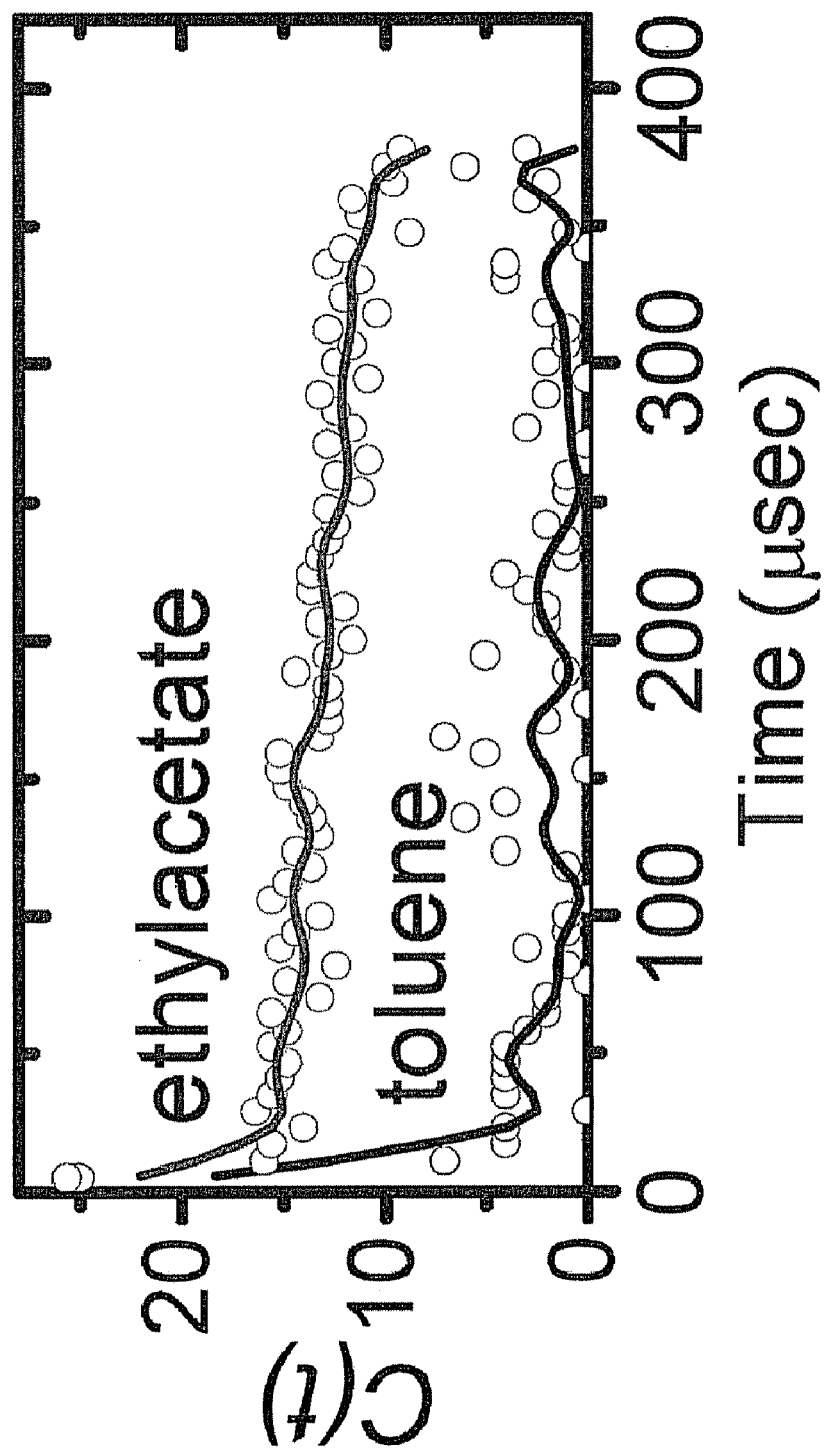
FIG. 31 illustrates the auto-correlation function (C(t)) of dynamic light scattering (DLS) of FC12/SWNTs dispersed in toluene and ethylacetate.

With an intention to address the nature of the significantly larger background absorption in the Vis-NIR spectra of ethylacetate and acetone of FIG. 30, dynamic light scattering (DLS) was used to qualitatively assess the presence or absence of nanotube bundling in various solvents. In order to minimize laser absorption by both nanotube and the tail-end of FC12, that inadvertently interferes with size-depended Brownian motion through thermal convection, a 633 nm laser line at 5 mW intensity power was employed. It has been reported that for laser powers below 150 mW, SWNT-related thermal convection effects become insignificant. FIG. 31 depicts the time-dependent auto-correlation function (ACF, (C(t)), for the toluene and ethylacetate dispersed FC12/SWNT samples of FIG. 30. Following the rapid initial C(t) decay, the toluene dispersion exhibits only a minor fluctuation between 20-75 μsec. On the other hand, the ethylacetate dispersion exhibits a broad fluctuation spanning in excess of 400 μsec, indicative of large bundling. This clearly suggests that the large absorbance background in ethylacetate and acetone FC12 dispersions originates from bundle-induced scattering.

Example 16

Flavin-Induced Luminescence Increase for SWNTs

Figure 32:
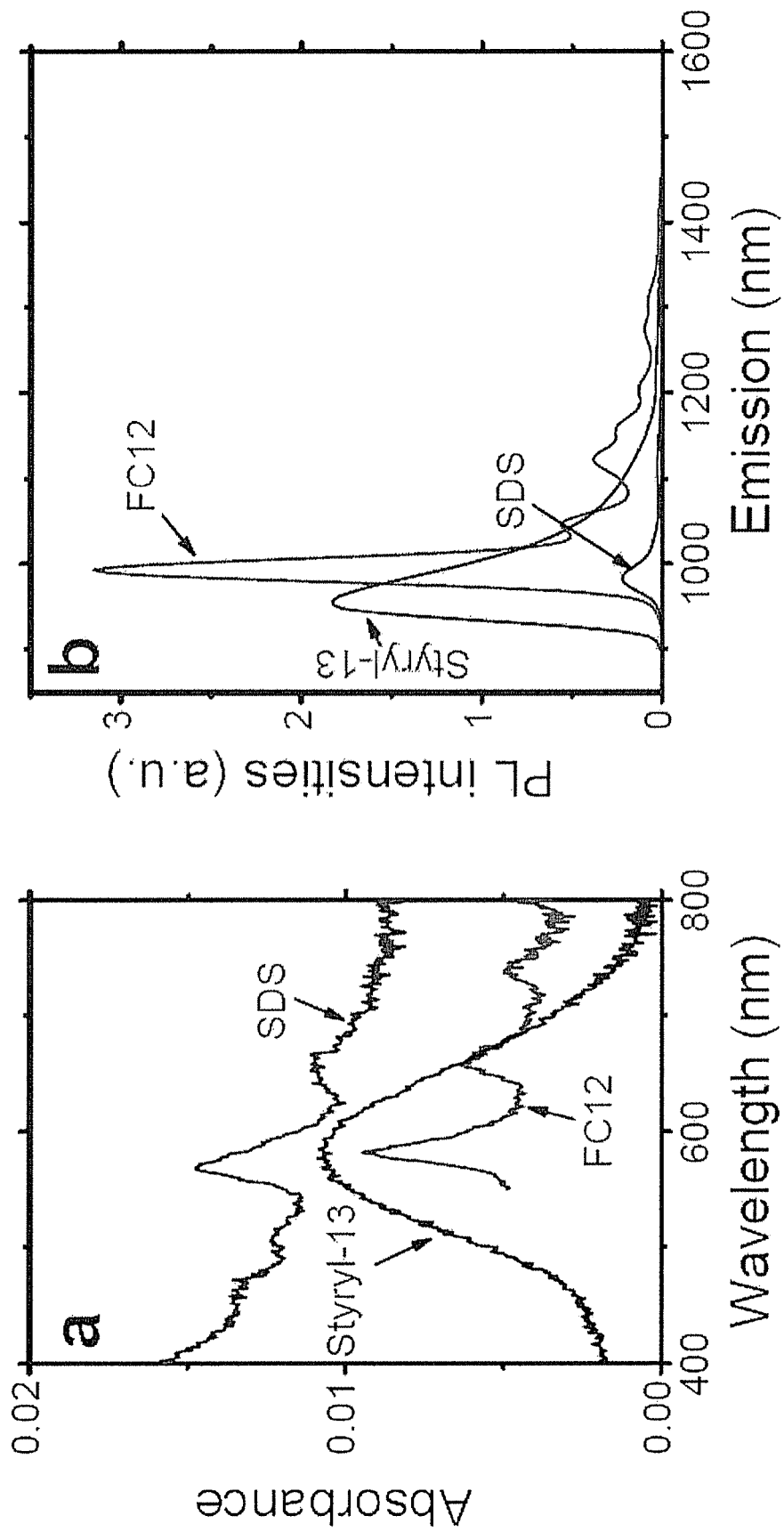
FIG. 32 illustrates the quantum yield (QY) determination for (6,5)-SWNTs when dispersed in SDS and FC12. QY values were determined by comparing their electronic absorption (a) and PL emission (b), in comparison with Styryl-13 reference standard (J. Crochet, M. Clemens, T. Hertel, *J. Am. Chem. Soc.* 2007, 129, 8058)

The intense PLE signal of toluene-dispersed FC12 dispersion in FIG. 29(*b*), prompted us to determine the PL quantum yield (QY), along the lines of the method described by J. Crochet et al. *J. Am. Chem. Soc.* 2007, 129, 8058. FIGS. 32(*a*) and (*b*) illustrate the absorbance and emission spectra of 2-[p-dimethylaminophenyl)-2,4-neopentylene-1,3,5,7-octatetraenyl]-3-ethyl-(6,7-benzo)-benzothiazolium perchlorate (also known as Styryl-13), in comparison with the $E^S_{22}$ absorption and $E^S_{11}$ emission profiles of SDS- and FC12-dispersed CoMoCAT SWNTs. The 11% QY of Styryl-13 at $3.3 \times 10^{-7}$ M in methanol was utilized as a primary reference standard, due to close excitation and emission spectral overlap with (6,5)-SWNTs. Prior to determining the QY of toluene-dispersed FC12-SWNTs, we utilized the aqueous-dispersed SDS-SWNTs as a secondary standard. Since the power-law background signal in both SDS and FC12 can influence significantly the nanotube QY figures, we define as "sample" and "individual" QYs the values obtained when (6,5) absorption is taken from either zero absorbance units or the power-law fitted line, respectively (see Table 2). A value of 0.5% for "sample" QY was obtained at ultimate dilution, while keeping the SDS concentration above the critical micelle concentration of ca. 1 wt. %. Progressively higher concentrations lower the QY down to 0.05% and below, in accordance with previously published reports. The substantially higher PL intensity of FC12- vs. SDS-dispersed SWNTs in FIG. 32(*b*), yields a "sample" QY of ca. 11% for (6,5)-SWNTs. When the scattering background is removed, the "individual" (6,5) QY increases to ca. 20%. Table 2 (above) lists the corresponding (6,5) QYs for all solvents in this study. o-Xylene and benzene, demonstrated 17 and 10% "individual" QY for (6,5)-SWNTs, respectively, with the remaining solvents showing progressively lower QY values (vide infra).

Figure 33B:
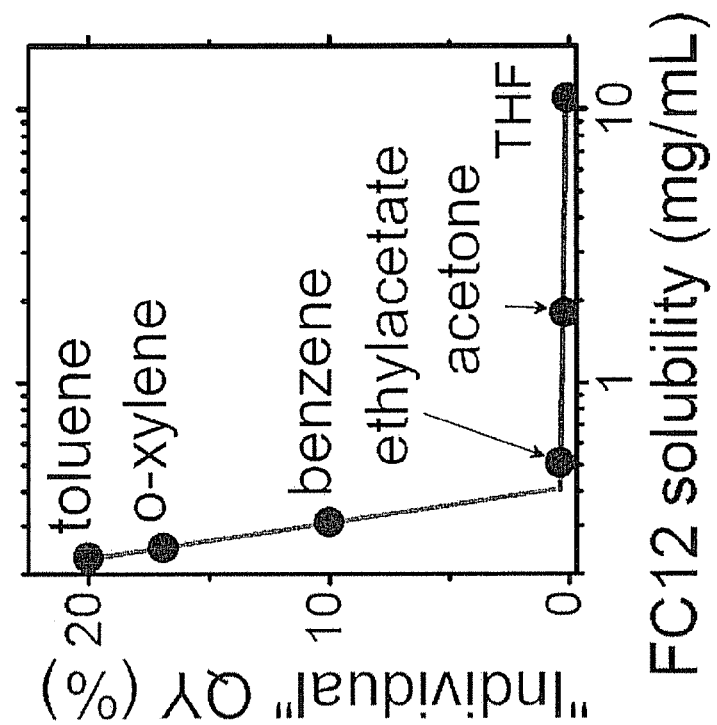
FIG. 33(*a*) illustrates the photo-oxidation stability of SDS- and FC12-dispersed SWNTs. SDS-dispersed SWNTs are susceptible to photo-oxidation, while FC12-dispersed nanotubes are not. This is attributed to the tightness of the FC12 helix in toluene that excludes and prevents contact of oxygen-related species with SWNTs.
Figure 33A:
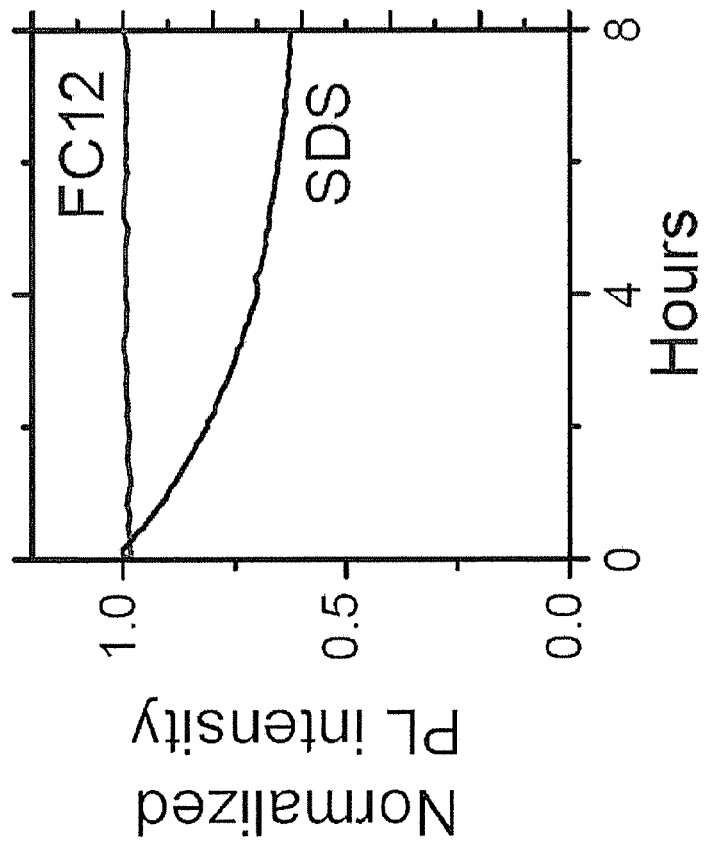
Figure 34:
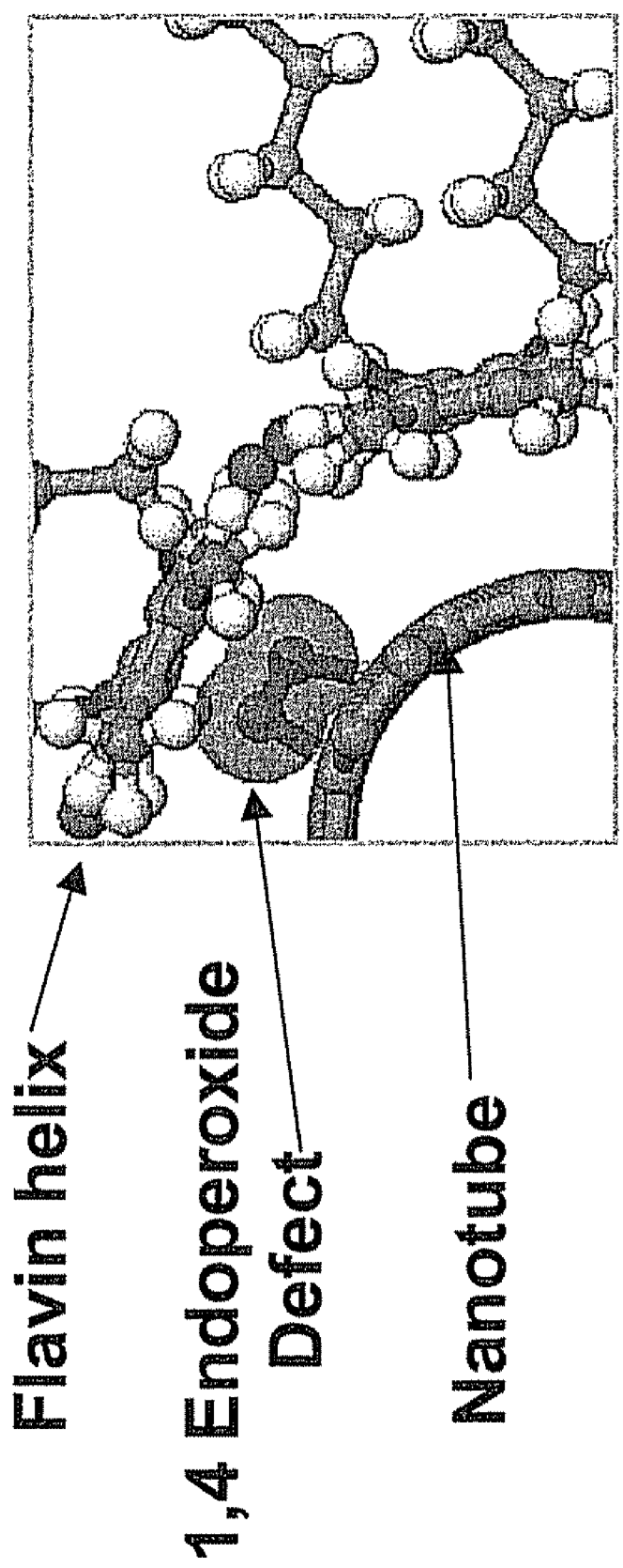
FIG. 34 illustrates a close-up of the helical flavin wrapping around a (6,5)-SWNTs. The flavin wrapping greatly interferes with the presence of a chemisorbed oxygen species (i.e., 1,4-endoperoxide and its shaded van der Waals radii)

In order to pinpoint the nature of such high QY, we closely investigated the tight helical wrapping of FC12 onto nanotube by time-dependent PL intensity traces as a function of $O_2$. FIG. 33(*a*) illustrates the normalized PL intensity of SDS- and FC12-dispersed (6,5) SWNTs, as a function of irradiation time. Unlike SDS dispersion, which exhibits progressively lower PL as a function of irradiation, the PL intensity of toluene FC12 dispersion showed no such susceptibility. While the reversible acid-induced p-doping of SWNTs in the presence of oxygen is been well-documented, significant less attention has been exerted on nanotube interactions with oxygen alone. Density functional theory calculations by Dukovic et al. (*J. Am. Chem. Soc.*, 2004, 126, 15269) indicate that singlet $O_2$ ($^1\Delta$) chemisorbs on a (5,0)-SWNT and adopts an 1,4-endoperoxide structure (FIG. 34). Since the calculated activation energy for 1,4-endoperoxide desorption (ca. 1 eV) is about half of the binding energy of a single isoalloxazine moiety (ca. 2.2 eV) (C. S. Lin, R. Q. Zhang, T. A. Niehaus, T. Frauenheim, *J. Phys. Chem. C*, 2007, 111, 4069), the displacement of chemisorbed $O_2$ in favor of a flavin helix can be readily accomplished. As illustrated in FIG. 34, the seamless isoalloxazine wrapping is severely prohibited in the presence of a chemisorbed 1,4-endoperoxide due to van der Waals repulsions. In contrast to FC12, the loose organization of other surfactants (SDS, SDBS, etc.) around SWNTs permits the inclusion of these 1,4-endoperoxide defects. In the absence of protons, the neutral endoperoxide structure imparts minor p-doping to the SWNT, while in the presence of acid this increases significantly. While the minor doping of the neutral endoperoxide does not appear to quench nanotube luminescence, it might provide a channel for non-radiative decay. Such channel can explain the significantly lower PL quantum efficiency of SWNTs in the presence of various surfactants that can co-exist with neutral endoperoxide. In addition, the removal of such endoperoxide leads to greater amount of SWNT dedoping, as witnessed by the increase in $E^S_{11}/E^S_{22}$ absorption ratio (vide supra). This is in accordance with the results of Strano et al, (*J. Phys. Chem. B*, 2003, 107, 6979) shown in FIG. 14(*b*), where oxygen-induced doping of SWNTs at various pHs suppress the $E^S_{11}$ transitions to a greater extent than the corresponding $E^S_{22}$ transitions. Furthermore, and based on the results of FIG. 14 and equation (2), it appears that exclusion of oxygen-induced defects on the side-walls of SWNTs are also afforded by the water soluble FMN, since the $E^S_{11}$ nanotube spectrum is insensitive to acid-doping.

The facile nanotube individualization and high QYs afforded by FC12 in certain solvents, begs the question why these solvents behave so differently. The answer to this question is believed to originate from the relative solubility differences of the two FC12 sub-moieties (i.e., isoalloxazine ring and dodecyl side chain). For this, we procured 10-methyl isoalloxazine (lumiflavin), the closest analogue to the isoalloxazine ring, and investigated its solubility characteristics versus that of FC12. Table 1 tabulates the solubilities of lumiflavin and FC12 as a function of dielectric constant ($\in$) of various solvents. Both lumiflavin and FC12 exhibit significantly reduced solubilities in non-polar solvents (i.e., benzene, toluene and o-xylene), with toluene the lowest. As solvent polarity increases (i.e., ethylacetate, THF and acetone), their solubilities increase accordingly. Pyridine and DMF exhibit the highest solubility values for both lumiflavin and FC12, albeit an absence of nanotube PL activity. Such behavior is believed to originate from the moderate-strong H-bonding ability of pyridine and DMF, capable of dissociating the H-bonded FC12 ribbon responsible for nanotube-dispersion. FIG. 33(*b*) shows the "individual" QY of (6,5)-SWNTs as a function of FC12 solubility in the respective solvent (Table 2). Two distinct regimes can be discerned, with high and low QYs for low and medium polarity solvents, respectively. For both regimes, the increase in FC12 solubility was followed by a decrease in QY. Since H-bonding is responsible for both helix stability and FC12/lumiflavine dissolution, increasing solvent polarity is expected to increase the helix dissociation constant and render FC12-wrapped nanotubes more prone to bundling and less capable to desorb 1,4-endoperoxide defects. On the basis of the observed aggregation tendencies, the low QYs in regime B appear to be dominated by nanotube bundling. In low-polarity solvents, the tight helical wrapping prevents nanotube bundling, which results in higher QY. Moreover, the proportionality of the helix dissociation constant to the FC12 solubility, explains the linear dependence of 1,4-endoperoxide defect removal along the one dimensional SWNT structure.

Example 17

Preferential Removal of Carbonaceous Fragments from SWNT Dispersion

The purification of SWNTs from carbonaceous impurities is crucial for further separation by type (metallic vs. semiconducting), diameter, length, chirality and handedness. The purification step of as grown nanotubes encompassed by various acid or base treatments (to remove metallic catalyst and supports) as well as intensive sonication. These treatments damage the nanotubes and create carbonaceous fragments (CFs). It is currently believed that the featureless background absorption of individualized SWNTs originate from both scattering and CF absorption effects. As shown in FIG. 31, if all nanotubes are truly individualized, the scattering contribution is minimized and the CF absorption dominates the contribution to their featureless background absorption. For example, the prolonged sonication of nanotubes for over 2 hours increases both peak and background intensities as a result of individualizing them along with damaging them at the same time. This is determined by the fact that the peak to background ratio of remains same after 2 hours of sonication.

Similarly, ion-exchange chromatography of DNA-wrapped SWNTs has demonstrated to effectively elimination of CFs, at the prohibitive cost of DNA. Such DNA-wrapped nanotubes exhibit little background absorptions and sharp $E_{11}^S$ and $E_{22}^S$ transitions due to the presence of individual carbon nanotubes. However, this chromatography-assisted purification showed very limited recovery of the sample, presumably due to clogging of bundled SWNTs and CFs in the column. Therefore, the removal of these CFs will be highly desirable for further separation of the SWNT.

The CF removal can be conducted utilizing a simple extraction of aqueous media containing the FMN/HiPco-SWNT composite against an organic solvent. After 4 cycles, the amorphous background has been considerably reduced by about 300 to 400%, while peak intensity at 745 nm has reduced only by 42%. This sequential extraction against organic solvent shows preferential elimination of carbonaceous fragments from the sonication-assisted dispersion of FMN/HiPco-SWNT composite in an aqueous solution.

Figure 35:
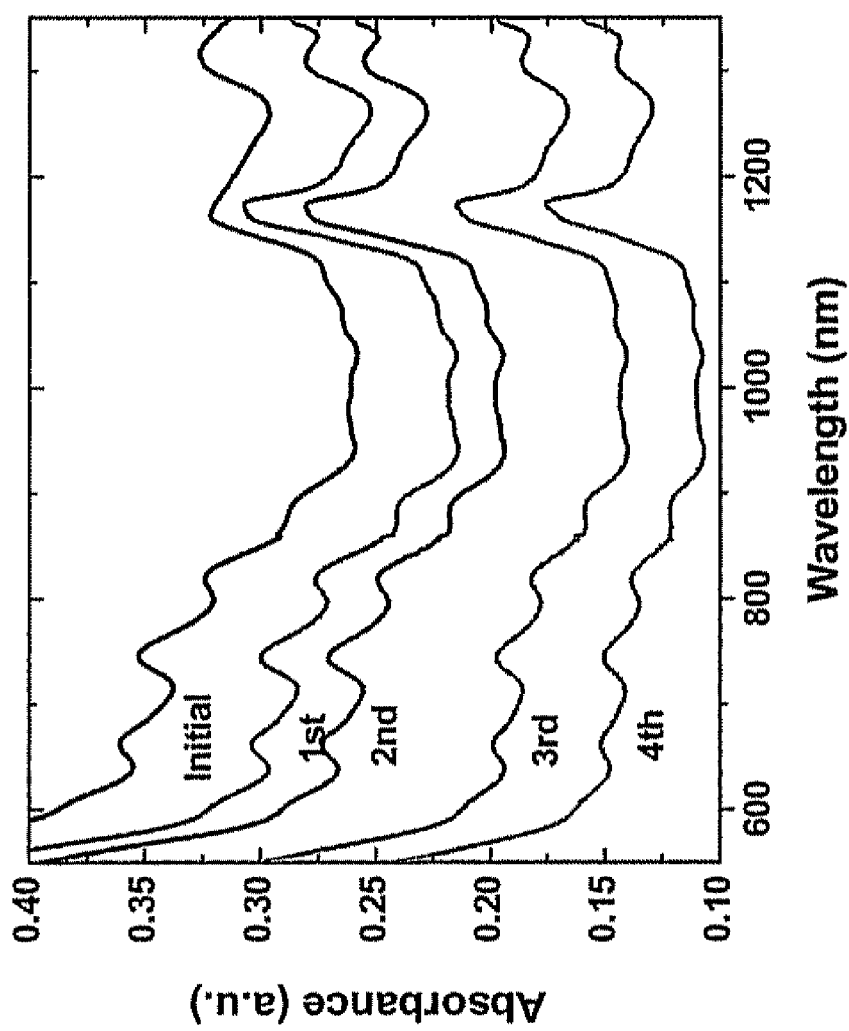
FIG. 35 shows UV-Vis-NIR spectra of FMN/HiPco-SWNT composite in aqueous solutions that have been exposed to various extraction steps against ethyl acetate.

FIG. 35 shows the UV-Vis-NIR spectra of initial solution and its subsequent extraction against ethyl acetate solution. The initial dispersion shows well-resolved $E_{22}^S$ transitions of SWNTs, amidst a substantial featureless background of carbonaceous materials. Upon extraction of the aqueous solution against organic solvent (i.e. ethyl acetate), carbonaceous fragments partition selectively between the water and ethyl acetate interface, while FMN-solubilized SWNTs are selectively partitioned at the aqueous phase. The UV-Vis spectroscopy confirms that the ethyl acetate layer does not contain any carbonaceous materials or nanotubes transferred from the aqueous layer. The subsequent extraction further eliminated the carbonaceous material as well as small amounts of carbon nanotubes. To evaluate the CF purification efficiency, the height ratio was utilized to see the enrichment of the peak.

$$\text{Ratio (\%)} = \frac{\left[1 - \left(\frac{\text{absorbance from carbonaceous material at 745 nm}}\right)\right] \times 100}{(\text{absorbance at 745 nm})} \quad \text{(eq. 3)}$$

Figure 36:
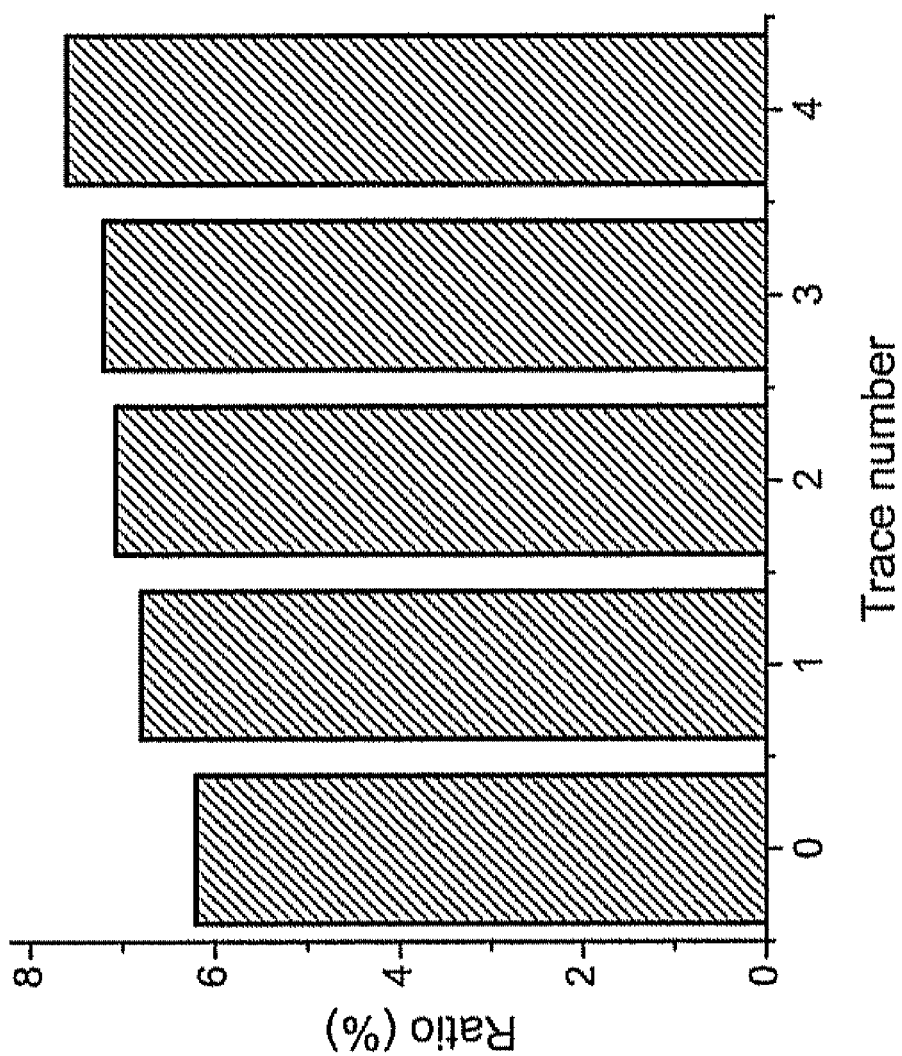
FIG. 36 depicts the ratio of SWNTs vs. carbonaceous fragments (CFs) height at 745 nm with successive extraction steps (hereby termed trace number) of FMN-dispersed nanotubes against ethyl acetate.

Equation (3) facilitates quantification of the enrichment of pure SWNT from a mixture of SWNT and CFs. FIG. 36 shows a trace-wise change of the enrichment ratio of the peak, compared to the background absorbance. Upon subsequent extraction, the enrichment ratio is witnessed to increase monotonically, while leaving CFs in the interface layer.

Figure 37:
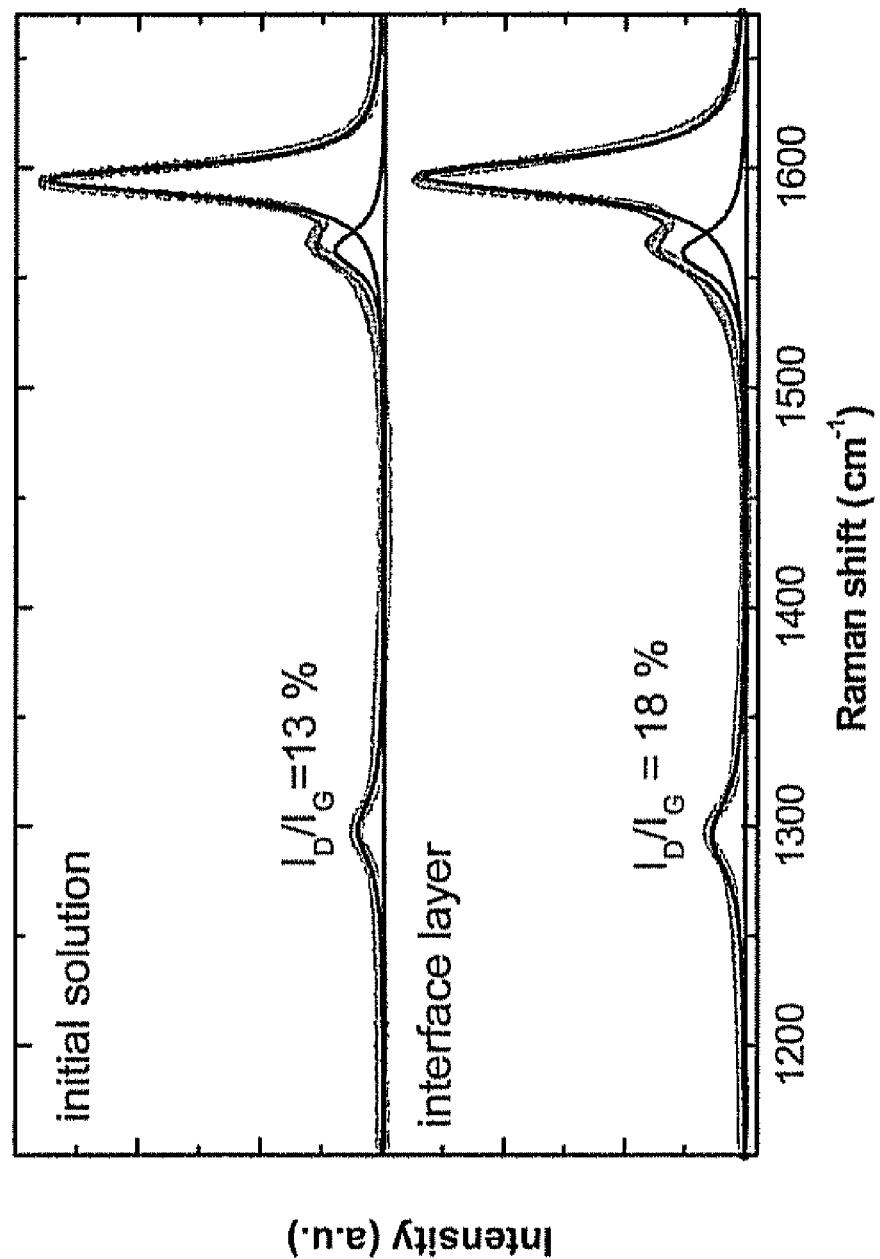
FIG. 37 depicts the SWNT Raman spectra from the interfacial layer sample (bottom) and initial FMN starting solution (top), deposited on a Si wafer.

FIG. 37 shows the Raman spectra of the interfacial sample (bottom) after the fourth extraction step and the initial FMN-SWNT starting solution (top), deposited on a silicon wafer. The D and G bands located at ca. 1293 and 1593 nm, respectively, as well their intensity ratio, are related to the disorder within a given nanotube sample. The initial D/G ratio ($I_D/I_G$) increases from 13% to ca. 18% for the material concentrated to the ethyl acetate/water interface.

Replacing the ethyl acetate phase with a stationary $C_{18}$-coated silica gel is expected to improve the purification efficiency and streamline this separation process step. The addition of small amount of ethyl acetate with the stationary $C_{18}$-column is also expected to improve this separation considerably.

Example 18

Possible Tight Helical Wrapping Molecules

Figure 38A:
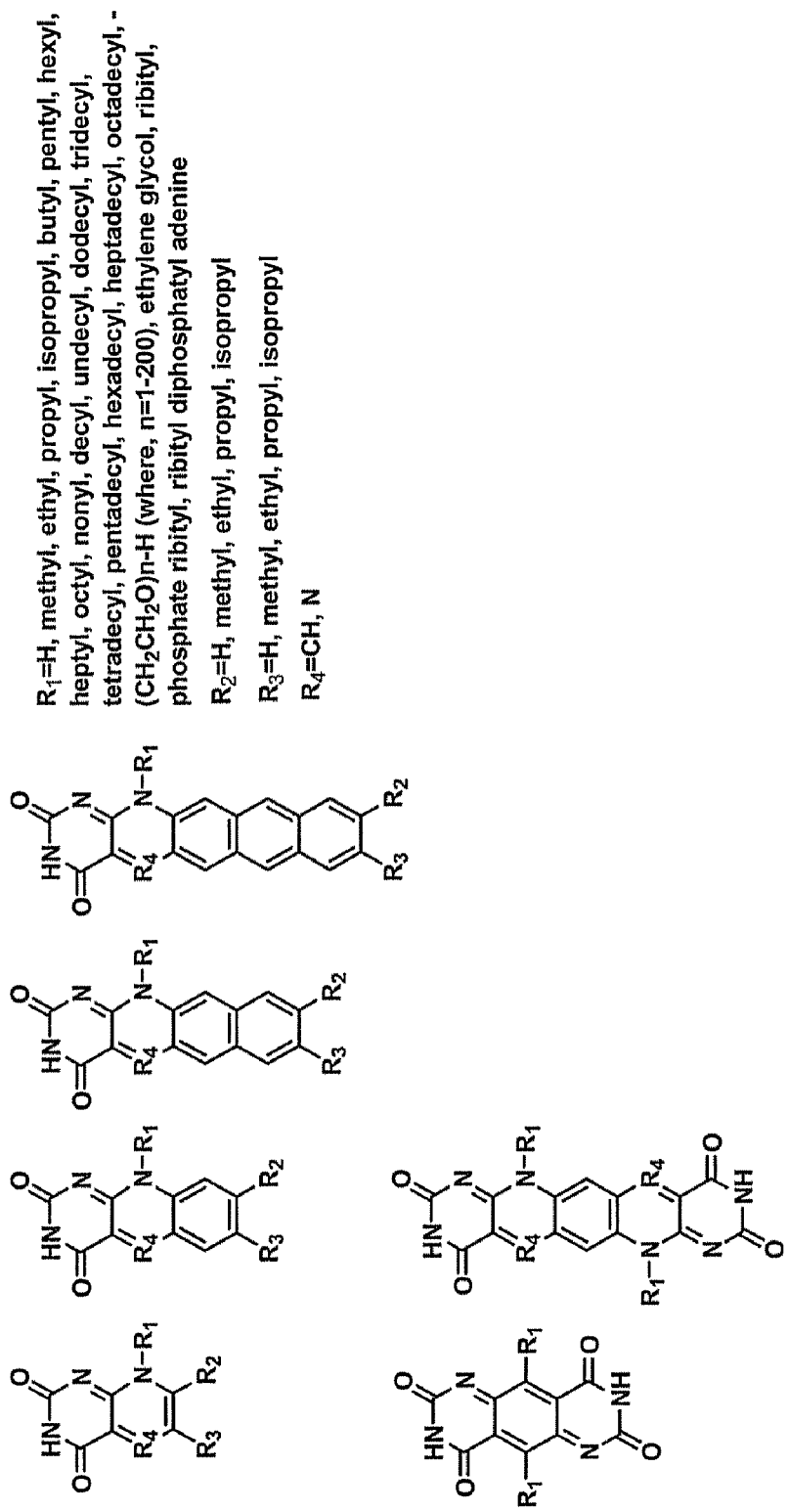
FIG. 38(*a*) shows flavin derivatives.

A variety of flavin derivatives, which can form charge-transfer complexes with SWNTs as well intermolecular H-bonded structures can afford similar separation by kind, diameter, chirality and handedness. FIG. 38a illustrates the structure of a variety of isoalloxazine moieties expected to afford such separation. By changing the number of aromatic rings, one can fine tune the charge transfer interaction between the flavin and SWNTs of various kinds.

Figure 38B:
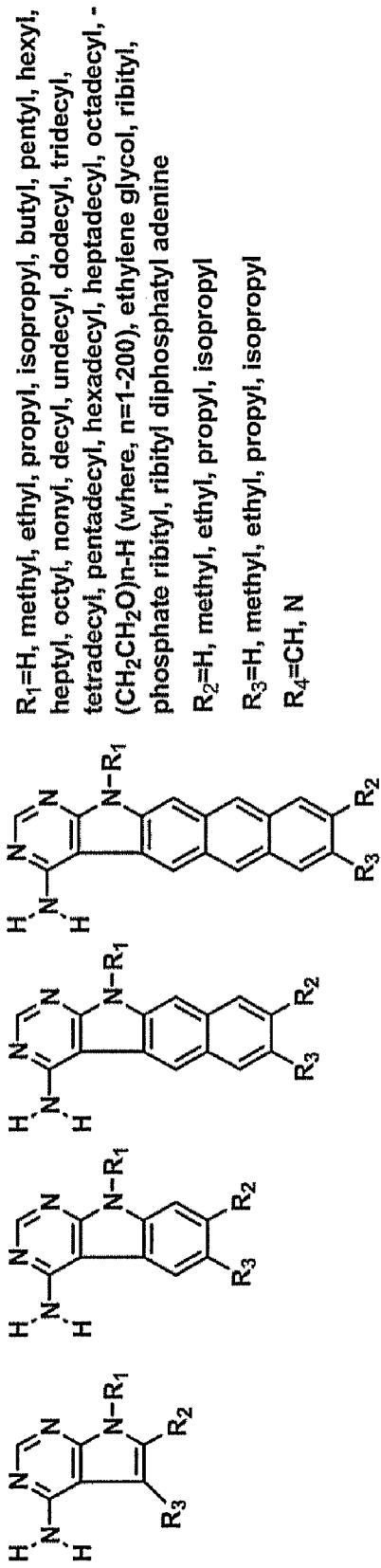
Figure 39:
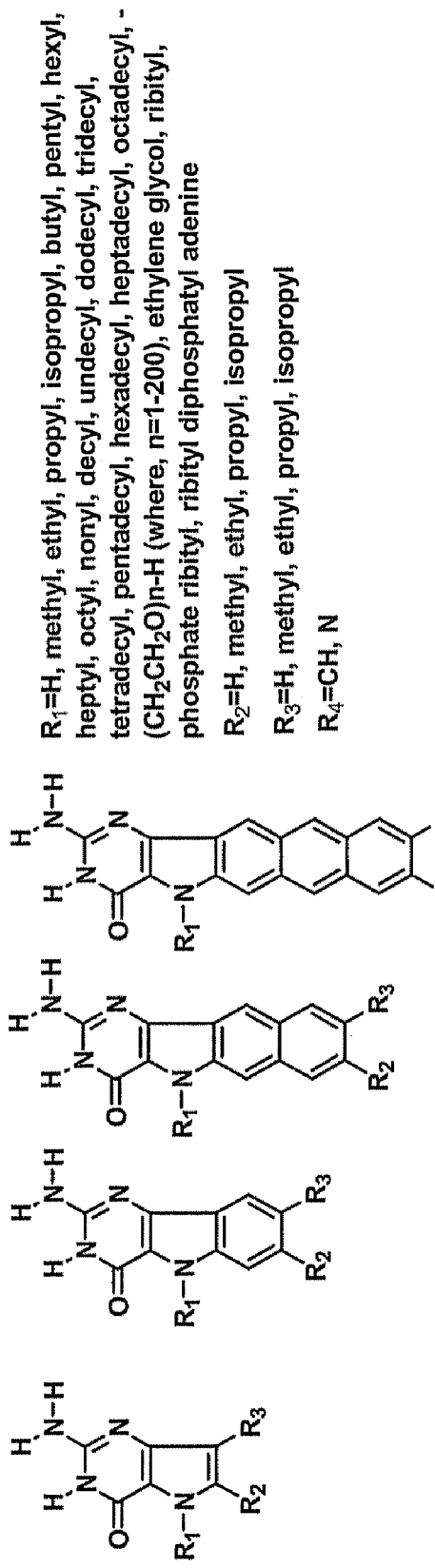
FIG. 39 shows guanine derivatives.
Figure 40:
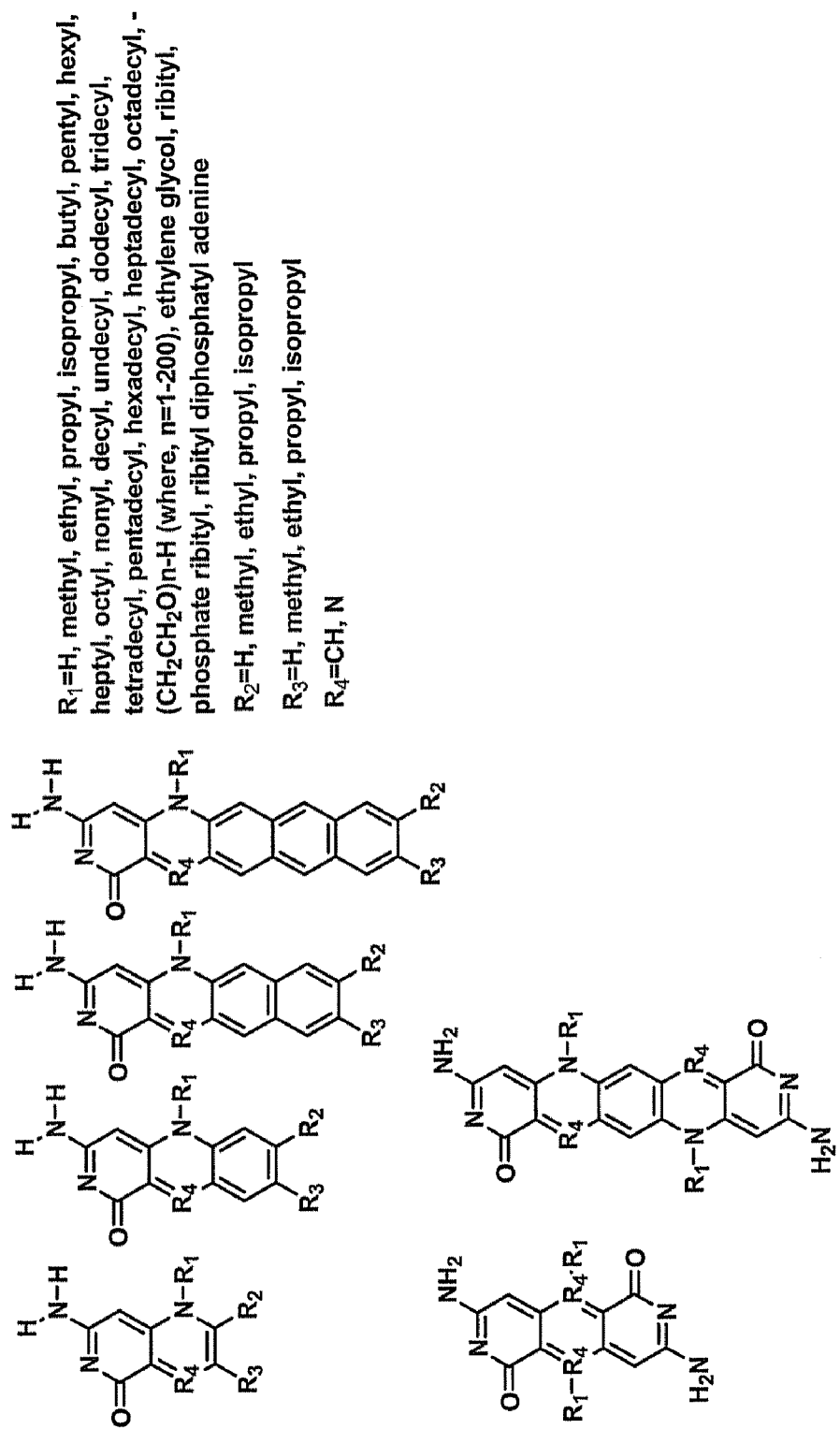
FIG. 40 shows cytosine derivatives.
Figure 41:
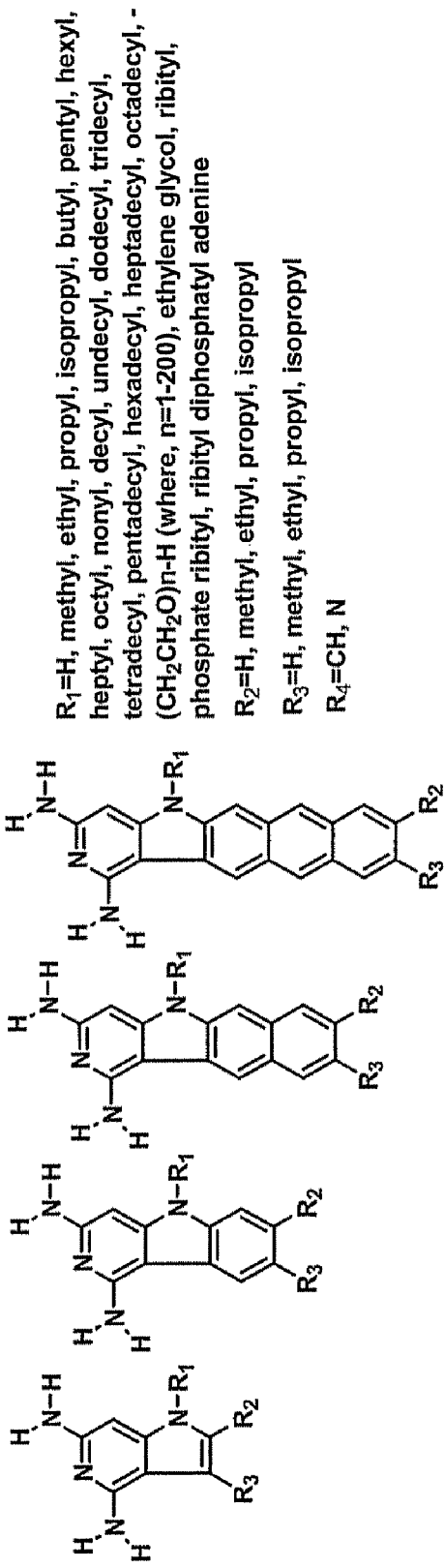
FIG. 41 shows melamine derivatives.

Another possible tight helical wrapping can be induces by adenine (FIG. 38(b)), guanine (FIG. 39), cytosine (FIG. 40) and melamine (FIG. 41) analogues.

Figure 42:
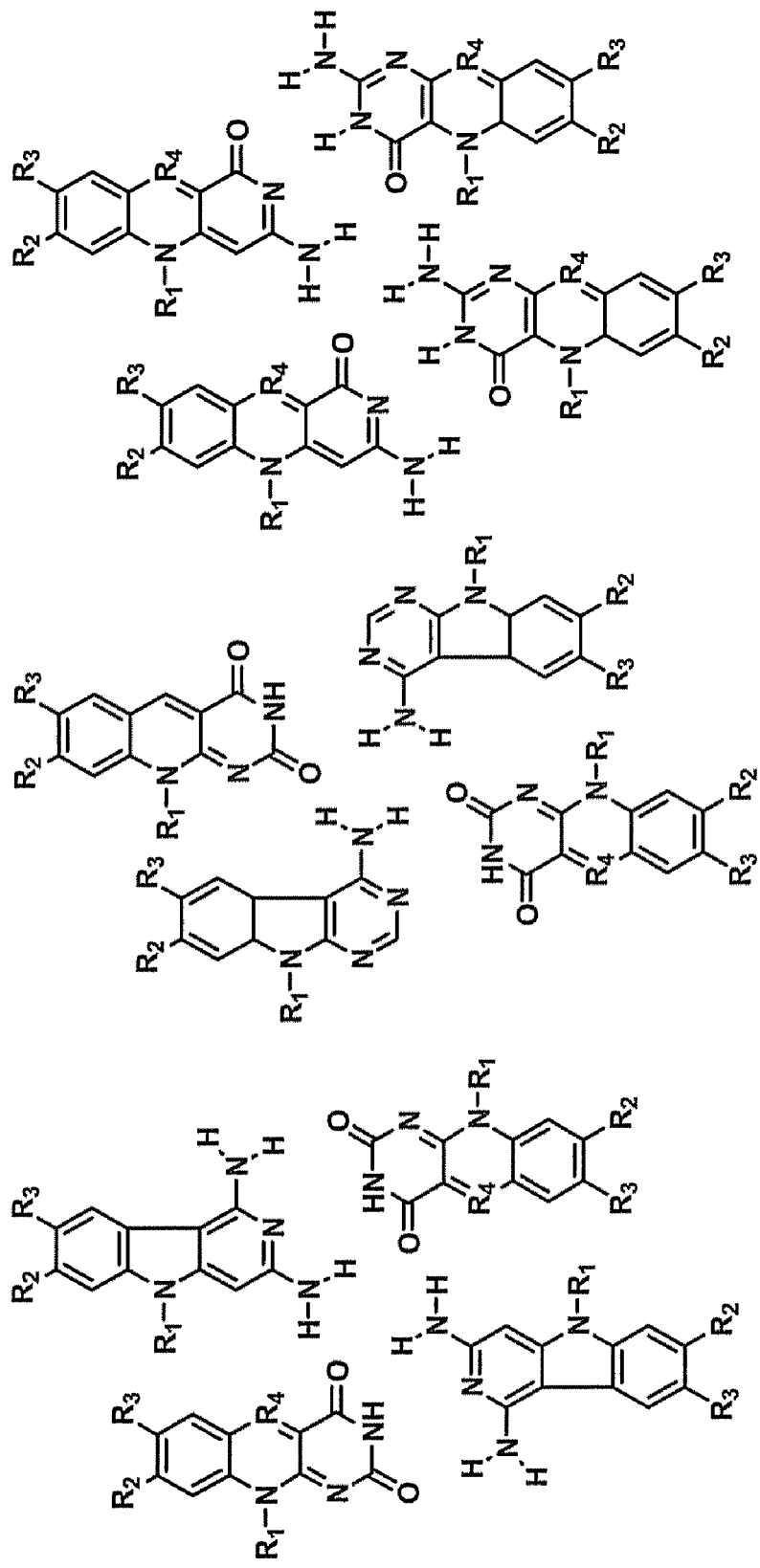
FIG. 42 shows configurations for tight helical wrapping of suggested molecules.

Alternative H-bonding arrangements between two of the aforementioned isoalloxazine, adenine, guanine, cytosine, and melamine structures can also lead to tight helical wrapping structures as shown in FIG. 42.

Figure 43:
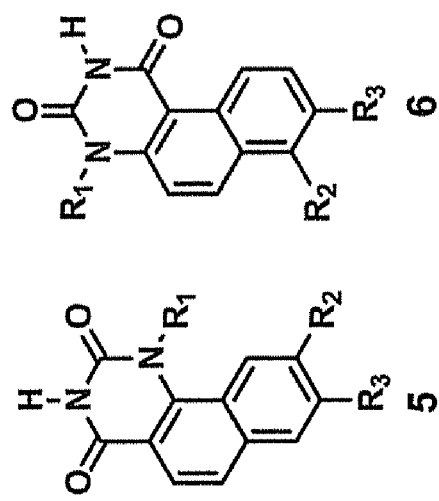
FIG. 43 shows molecules for chirality enrichment of zigzag, or near zigzag type of nanotubes.

FIG. 43 illustrates an alternative H-bonding motif that aligns parallel to low chiral angle nanotubes as opposed to the aforementioned structures that line up parallel to high chiral angle nanotubes.

From the examples above it may be seen that flavin moieties and/or non-flavin containing molecular species can self-assemble to around a nanotube. The flavin moieties and/or non-flavin containing molecular species undergo a charge transfer with the nanotube. The flavin moieties and/or non-flavin containing molecular species undergo a two-dimensional hydrogen bonding with each other, the hydrogen bonding facilitating the formation of the helix around the nanotube. The flavin moieties and/or a non-flavin containing molecular aromatic species can have substituents that render the composite soluble in an aqueous solvent, an organic solvent, or a combination comprising at least an aqueous solvent and an organic solvent.

It can also be seen that the epitaxial organization of the composite results in a) increased luminescence efficiency over a nanotube that is not in composite form; b) an exclusion of undesired physisorbed moieties when compared with a nanotube that is not in composite form; c) reduced pH-assisted doping when compared with a nanotube that is not in composite form; d) renders a more pure semi-conductor material when compared with a nanotube that is not in composite form; e) assists in further self-assembly and device organization when compared with a nanotube that is not in composite form; f) assists in nucleating crystals off of the nanotubes of the composite that promote further crystallization of the surrounding matrices that host these nanotubes; or g) assists in obtaining composites that have a higher percentage of nanotubes that are chirally similar to each other or similar to each other based on handedness when compared with a mass of nanotubes that are not in composite form. In addition, the ability to obtain both chirally and handedness similar nanotubes is important for uses in seeding off larger quantities of structurally and electronically similar nanotubes.

From the examples it can be seen that nanotubes that are derived from the composites have a higher percentage of nanotubes that are chirally similar to each other or similar to each other based on handedness. These chirally and handedness pure nanotubes can interlock with themselves to form a harder nanotube aggregate when compared with nanotubes that are not derived from the formation of the composite.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A method comprising:
dispersing a plurality of (n,m)-nanotubes in media that comprises flavin moieties and/or non-flavin containing molecular species to form a mixture; the flavin moieties being substituted with solubilizing side chains;
self-assembling the flavin moieties and other non-flavin containing molecular species in a pattern that is orderly wrapped around the nanotubes to form a composite;
introducing an effective amount of a surfactant into the mixture to disturb the wrapping of the flavin moieties and other non-flavin containing molecular species around all other nanotubes but the strongest flavin-bound nanotube; the disturbing resulting in a complete or partial surfactant-replacement of the flavin moieties from the nanotube;
introducing a salt to induce aggregation of all flavin-replaced or partially replaced nanotubes; and
centrifuging out all nanotube aggregates from the mixture to extract the strongest flavin-bound nanotubes from the plurality of (n,m) nanotubes.

2. The method of claim 1, where the flavin moiety is flavin mononucleotide.

3. The method of claim 1, where the extracted nanotube has (8,6) has chirality.

4. The method of claim 1, where the surfactant is sodium dodecyl sulfate, sodium dodecyl benzene sulfonate or sodium cholate.

5. The method of claim 1, wherein the flavin moieties are riboflavin, flavin mononucleotide, flavin adenine dinucleotide, FC12 (10-dodecyl-7,8-dimethyl-10H-benzo[g]pteridine-2,4-dione) or a combination comprising at least one of the foregoing flavin moieties.

6. The method of claim 1, where the media is an aprotic polar solvent, a polar protic solvent, a non-polar solvent or a combination comprising at least one of the foregoing solvents.

7. The method of claim 1, where the media is water, propylene carbonate, ethylene carbonate, butyrolactone, acetonitrile, benzonitrile, nitromethane, nitrobenzene, sulfolane, dimethylformamide, N-methylpyrrolidone, methanol, ethanol, propanol, isopropanol, butanol, benzene, toluene, ortho-xylene, meta-xylene, para-xylene, chlorobenzene, carbon tetrachloride, hexane, diethyl ether, tetrahydrofuran, propylene carbonate, ethylene carbonate, ethylene glycol, diglyme, triglyme, tetraglyme, nitromethane, methylene chloride, chloroform, acetone, ethyl acetate, or a combination comprising at least one of the foregoing solvents.

8. The method of claim 1, where the non-flavin containing molecular species are hydrogen-bonding prone agents; the hydrogen-bonding prone agents being sugars, monosaccharides, D-glucose, L-glucose, D-galactose, L-galactose, D-mannose, L-mannose, disaccharides, sucrose, lactose, maltose, trehalose, cellobiose, oligosaccharides, and a combination comprising at least one of the foregoing non-flavin containing molecular species.

9. The method of claim 1, further comprising precipitating the surfactant-replaced nanotubes from the mixture by changing the pH of the mixture, subjecting the mixture to light treatment, by subjecting the mixture to a hydrogen peroxide treatment, or by a combination thereof.

10. The method of claim 1, further comprising sequentially removing other (n,m)-nanotubes from the mixture based on an affinity constant (Ka) of the flavin moiety and/or the non-flavin containing molecular species-wrapping for each (n,m) chirality species.

11. A method comprising:
dispersing nanotubes in media that comprises small-molecular weight aromatic moieties and/or other non-aromatic containing molecular species that possess multiple H-bonding and are substituted with solubilizing side chains;
self-assembling the small-molecular weight aromatic moieties and/or other non-aromatic containing molecular species in a pattern that is orderly wrapped around the nanotubes to form a composite; the wrapping occurring because of the hydrogen bonding between the small-molecular weight aromatic moieties and/or other non-aromatic containing molecular species;
introducing desired amounts of an optional reagent that competes with self-assembly in to disturb the wrapping around nanotubes with moderate order and creates disturbed nanotube composites; and
separating out the said composite from the mixtures of said disturbed nanotube composites, wherein the small-molecular weight aromatic moieties are riboflavin, flavin mononucleotide, flavin adenine dinucleotide, FC12 (10-dodecyl-7,8-dimethyl-10H-benzo[g]pteridine-2,4-dione) or a combination comprising at least one of the foregoing flavin moieties.

12. The method of claim 11, where the composite is separated from the disturbed nanotube composite using centrifugation.

13. The method of claim 11, wherein the media comprises aqueous media or deuterated aqueous media.

14. The method of claim 11, wherein the media is water.

15. The method of claim 11, wherein the dispersing is accomplished by a process that comprises sonication.

16. The method of claim 15, wherein the dispersing is further accomplished by devices that use shear force, extensional force, compressive force, ultrasonic energy, electromagnetic energy, thermal energy or combinations comprising at least one of the foregoing forces or forms of energy.

17. The method of claim 11, further comprising separating bundled nanotubes, carbonaceous impurities, and metallic impurities from the composite.

18. The method of claim 11, where the flavin moieties are substituted with a substituent.

19. The method of claim 11, where the flavin moieties are substituted at the 7, 8 and 10 positions with a substitutent.

20. The method of claim 19, where the substituent comprises a complex chiral center; the complex chiral center being a R- or L-ribityl, R- or L-ribityl phosphate, R- and L-ribityl diphosphatic adenine; R- or L-arabityl, R- or L-arabityl phosphate, R- and L-arabityl diphosphatic adenine; R- or L-xylityl, R- or L-xylityl phosphate, R- and L-xylityl diphosphatic adenine; R- or L-xylityl, R- or L-xylityl phosphate, R- and L-xylityl diphosphatic adenine; R- or L-lyxytyl, R- or L-lyxytyl phosphate, or R- and L-lyxytyl diphosphatic adenine.

21. The method of claim 18, wherein the substituent is an oligomer, a homopolymer, a copolymer, a block copolymer, an alternating block copolymer, a random polymer, a random copolymer, a random block copolymer, a graft copolymer, a star block copolymer, a dendrimer, a liquid crystalline polymer, a lyotropic crystalline polymer, a dye, a pigment, a drug, a crystallizable drug, a therapeutic biologically active agent, a pharmaceutic biologically active agent, a protein, a nucleic acid, a fullerene, nanocrystals, nanorods, deoxyribonucleic acid oilogmers, nanoplatelets or a protein nucleic acid oligomer.

22. The method of claim 18, wherein the substituent is a DNA oligomer, a RNA oligomer, a fullerene, a substituted fullerene, a nanocrystal, a substituted nanocrystal, a nanorod, a substituted nanorod, a nanoplatelet, or a substituted nanoplatelet.

23. The method of claim 11, where the other non-aromatic containing molecular species further comprise hydrogen-bonding prone agents that stabilize the self-assembly of the small-molecular weight aromatic moieties on the nanotubes; the hydrogen-bonding prone agents being sugars, monosaccharides, D-glucose, L-glucose, D-galactose, L-galactose, D-mannose, L-mannose, disaccharides, sucrose, lactose, maltose, trehalose, cellobiose, oligosaccharides, and a combination comprising at least one of the foregoing reagents.

24. The method of claim 11, where the optional reagent is a reducing agents the reducing agent being sodium dithionite, potassium dithionite, lithium aluminum hydride, sodium borohydride, hydrazine, zinc-mercury amalgam, diisobutylaluminum hydride, a Lindler catalyst, oxalic acid, sodium amalgam, ferrous ions, hydrogen, or a combination comprising at least one of the foregoing reducing agents.

25. The method of claim 11, where the media comprises solvents that facilitate the self assembly of the small-molecular weight aromatic moieties and/or the non-aromatic containing molecular species on the carbon nanotubes; the solvent being a liquid aprotic polar solvent, a polar protic solvent, a non-polar solvents or a combination comprising at least one of the foregoing solvents.

26. The method of claim 25, where the solvent is water, propylene carbonate, ethylene carbonate, butyrolactone, acetonitrile, benzonitrile, nitromethane, nitrobenzene, sulfolane, dimethylformamide, N-methylpyrrolidone, methanol, ethanol, propanol, isopropanol, butanol, benzene, toluene, ortho-xylene, meta-xylene, para-xylene, chlorobenzene, carbon tetrachloride, hexane, diethyl ether, tetrahydrofuran, propylene carbonate, ethylene carbonate, ethylene glycol, diglyme, triglyme, tetraglyme, nitromethane, methylene chloride, chloroform, acetone, ethyl acetate, or a combination comprising at least one of the foregoing solvents.

27. The method of claim 11, where the nanotubes comprise carbon, boron, nitrogen, phosphorus, silicon, germanium, palladium, sulfur, cadmium, tellurium, molybdenum, tellurium, tungsten, selenium or a combination thereof.

28. The method of claim 11, where the nanotubes are tungsten disulfide nanotubes, molybdenum disulfide nanotubes, cadmium selenide nanotubes, cadmium sulfide nanotubes, cadmium telluride nanotubes, zinc sulfide nanotubes, palladium sulfide nanotubes, palladium selenide nanotubes, single wall carbon nanotubes, double wall carbon nanotubes, multiwall carbon nanotubes, boron-carbon nanotubes, boron-carbon-nitrogen nanotubes, carbon-nitrogen nanotubes or a combination comprising at least one of the foregoing nanotubes.

29. The method of claim 11, where the extracting of the composite from other nanotubes is further accomplished via process including filtration, fractional filtration, size-exclusion based chromatography, density gradient centrifuging, chromatography, anionic chromatography, silica gel columns, electrophoresis, dielectrophoresis or a combination comprising at least one of the foregoing processes.

30. The method of claim 11, where the centrifuging is conducted at a centrifugal force of about 2 g to about 500,000 g.

31. The method of claim 11, where the centrifuging is conducted at a centrifugal force of about 1,000 to 15,000 g.

32. The method of claim 11, where the centrifuging is conducted at a centrifugal force of about 150,000 g to about 500,000 g.

33. The method of claim 11, where the nanotubes are further extracted from the composite with a reducing agent, where the reducing agent is sodium dithionite, potassium dithionite, lithium aluminum hydride, sodium borohydride, hydrazine, zinc-mercury amalgam, diisobutylaluminum hydride, a Lindler catalyst, oxalic acid, sodium amalgam, ferrous ions, hydrogen, or a combination comprising at least one of the foregoing reducing agents.

34. The method of claim 11, where a centrifuged mass is extracted against a reagent.

35. The method of claim 11, where the reagent is ethyl acetate.

36. The method of claim 11, where the dispersing and centrifuging steps are repeated.

37. The method of claim 11, where the method is used to separate carbon nanotubes according to chirality, handedness, length, diameter and/or electrical conductivity characteristics.

38. A composite comprising:
a nanotube; and
small-molecular weight aromatic moieties that possess the means of multiple H-bonding that self-assembles to around the nanotube;
the aromatic moieties undergoing a charge transfer with the nanotube;
the aromatic moieties undergoing hydrogen bonding with each other; the hydrogen bonding facilitating the formation of an ordered two-dimensional lattice around the nanotubes;
the aromatic moieties having substituents that protrude outwards from the ordered two-dimensional lattice around nanotubes and render this assembly soluble in a solvent; and
the ordered two dimensional lattice around nanotubes excludes and prevents other molecular species to be adsorbed onto the nanotube side walls, wherein the small-molecular weight aromatic moieties are flavin moieties and non-flavin containing molecular aromatic species.

39. The composite of claim 38, where the self-assembly results in a composite that exhibits epitaxial organization of the two-dimensional lattice onto the nanotube lattice.

40. The composite of claim 39, where the epitaxial organization of the composite results in:
a) increased luminescence efficiency over a nanotube that is not in composite form;
b) an exclusion of undesired physisorbed moieties when compared with a nanotube that is not in composite form;
c) reduced pH-assisted doping when compared with a nanotube that is not in composite form;
d) renders a more pure semi-conductor material when compared with a nanotube that is not in composite form;
e) assists in further self-assembly and device organization when compared with a nanotube that is not in composite form;
f) assists in nucleating crystals off of the nanotubes of the composite that promote further crystallization of the surrounding matrices that host these nanotubes; or
g) assists in obtaining composites that have a higher percentage of nanotubes that are chirally and handedness similar to each when compared with a mass of nanotubes that are not in composite form.

41. The composite of claim 38, where nanotubes that are derived from the composites that have a higher percentage of nanotubes that are chirally similar to each other or handedness similar to each other when compared with nanotubes that are not in the composite.

42. The composite of claim 38, where the nanotubes comprise carbon, boron, nitrogen, phosphorus, silicon, germanium, palladium, sulfur, cadmium, tellurium, molybdenum, tellurium, tungsten, selenium or a combination thereof.

43. The composite of claim 38, where the nanotubes are tungsten disulfide nanotubes, molybdenum disulfide nanotubes, cadmium selenide nanotubes, cadmium sulfide nanotubes, cadmium telluride nanotubes, zinc sulfide nanotubes, palladium sulfide nanotubes, palladium selenide nanotubes, single wall carbon nanotubes, double wall carbon nanotubes, multiwall carbon nanotubes, boron-carbon nanotubes, boron-carbon-nitrogen nanotubes, carbon-nitrogen nanotubes or a combination comprising at least one of the foregoing nanotubes.

44. The composite of claim 38, where the nanotubes have a single wall, a double wall or multiple walls.

45. The composite of claim 38, where the small-molecular weight aromatic moieties are substituted flavin moieties.

46. The composite of claim 38, where the flavin moieties are substituted at the 7, 8 and 10 positions.

47. The composite of claim 45, where the substituent comprises a complex chiral center; the complex chiral center being a R- or L-ribityl, R- or L-ribityl phosphate, R- and L-ribityl diphosphatic adenine; R- or L-arabityl, R- or L-arabityl phosphate, R- and L-arabityl diphosphatic adenine; R- or L-xylityl, R- or L-xylityl phosphate, R- and L-xylityl diphosphatic adenine; R- or L-xylityl, R- or L-xylityl phosphate, R- and L-xylityl diphosphatic adenine; R- or L-lyxytyl, R- or L-lyxytyl phosphate, or R- and L-lyxytyl diphosphatic adenine.

48. The composite of claim 45, wherein the substituent is an oligomer, a homopolymer, a copolymer, a block copolymer, an alternating block copolymer, a random polymer, a random copolymer, a random block copolymer, a graft copolymer, a star block copolymer, a dendrimer, a liquid crystalline polymer, a lyotropic crystalline polymer, a dye, a pigment, a drug, a crystallizable drug, a therapeutic biologically active agent, a pharmaceutic biologically active agent, a protein, a nucleic acid or a protein nucleic acid oligomer.

49. The composite of claim 38, where the small-molecular weight aromatic moieties do not comprise nucleic acids and are 1-dodecyl-1H-pyrrolo[3,2-c]pyridine-4,6-diamine, 1-dodecyl-1H-benzo[h]quinazoline-2,4-dione, 2-amino-5-dodecyl-3,5-dihydro-pyrrolo[3,2-d]pyrimidin-4-one, 3-amino-5-dodecyl-5H-benzo[b][1,6]naphthyridin-1-one, 3-amino-5-dodecyl-5H-2,5-diaza-naphthacen-1-one, 3-amino-9-dodecyl-2,9-dihydro-2,4,9-triaza-fluoren-1-one, 3-amino-11-dodecyl-2,11-dihydro-2,4,1,1-triaza-benzo[b]fluoren-1-one, 3-amino-13-dodecyl-2,13-dihydro-2,4,13-triaza-indeno[1,2-b]anthracen-1-one, 3,7-diamino-9,10-didodecyl-2,6-diaza-anthracene-1,5-dione, 3,10-diamino-5,12-didodecyl-5,12-dihydro-2,5,7,9,12,14-hexaaza-pentacene-1,8-dione, 4-dodecyl-4H-benzo[f]quinazoline-1,3-dione, 5-dodecyl-5H-pyrido[4,3-b]indole-1,3-diamine, 5-dodecyl-5H-benzo[f]pyrido[4,3-b]indole-1,3-diamine, 5,10-dodecyl-pyrimido[4,5-g]quinazoline-2,4,7,9-tetraone, 7-amino-1-dodecyl-1H-[1,6]naphthyridin-5-one, 7-octyl-7H-pyrrolo[2,3-d]pyrimidin-4-ylamine, 7,14-didodecyl-7,14-dihydro-1,3,5,7,8,10,12,14-octaaza-pentacene-2,4,9,11-tetraone, 8-dodecyl-8H-pteridine-2,4-dione, 9-dodecyl-9H-1,3,9-triaza-fluoren-4-ylamine, 8,9-dimethyl-12-dodecyl-12H-1,3,5,12-tetraaza-naphthacene-2,4-dione, 11-dodecyl-9H-1,3,11-triaza-benzo[b]fluoren-4-ylamine, 12-dodecyl-12H-1,3,5,12-tetraaza-naphthacene and 14-dodecyl-4H-1,3,5,12-tetraaza-pentacene-2,4-dione.

50. The composite of claim 49, where any two of the molecular aromatic species from amongst 1-dodecyl-1H-pyrrolo[3,2-c]pyridine-4,6-diamine, 1-dodecyl-1H-benzo[h]quinazoline-2,4-dione, 2-amino-5-dodecyl-3,5-dihydro-pyrrolo[3,2-d]pyrimidin-4-one, 3-amino-5-dodecyl-5H-benzo[b][1,6]naphthyridin-1-one, 3-amino-5-dodecyl-5H-2,5-diaza-naphthacen-1-one, 3-amino-9-dodecyl-2,9-dihydro-2,4,9-triaza-fluoren-1-one, 3-amino-11-dodecyl-2,1,1-dihydro-2,4,1,1-triaza-benzo[b]fluoren-1-one, 3-amino-13-dodecyl-2,13-dihydro-2,4,13-triaza-indeno[1,2-b]anthracen-1-one, 3,7-diamino-9,10-didodecyl-2,6-diaza-anthracene-1,5-dione, 3,10-diamino-5,12-didodecyl-5,12-dihydro-2,5,7,9,12,14-hexaaza-pentacene-1,8-dione, 4-dodecyl-4H-benzo[f]quinazoline-1,3-dione, 5-dodecyl-5H-pyrido[4,3-b]indole-1,3-diamine, 5-dodecyl-5H-benzo[f]pyrido[4,3-b]indole-1,3-diamine, 5,10-dodecyl-pyrimido[4,5-g]quinazoline-2,4,7,9-tetraone, 7-amino-1-dodecyl-1H-[1,6]naphthyridin-5-one, 7-octyl-7H-pyrrolo[2,3-d]pyrimidin-4-ylamine, 7,14-didodecyl-7,14-dihydro-1,3,5,7,8,10,12,14-octaaza-pentacene-2,4,9,11-tetraone, 8-dodecyl-8H-pteridine-2,4-dione, 9-dodecyl-9H-1,3,9-triaza-fluoren-4-ylamine, 8,9-dimethyl-12-dodecyl-12H-1,3,5,12-tetraaza-naphthacene-2,4-dione, 11-dodecyl-9H-1,3,11-triaza-benzo[b]fluoren-4-ylamine, 12-dodecyl-12H-1,3,5,12-tetraaza-naphthacene and 14-dodecyl-4H-1,3,5,12-tetraaza-pentacene-2,4-dione can interact with one another via hydrogen interactions to form a helix around a nanotube.

51. The composite of claim 49, where the 1-dodecyl-1H-benzo[h]quinazoline-2,4-dione is substituted in the 1, 7, 8 and/or the 9 positions; the 2-amino-5-dodecyl-3,5-dihydro-pyrrolo[3,2-d]pyrimidin-4-one is substituted in the 5, 6 and/or the 7 positions; the 3-amino-5-dodecyl-5H-benzo[b][1,6]naphthyridin-1-one is substituted in the 5, 7, 8 and/or the 10 positions; the 3-amino-5-dodecyl-5H-2,5-diaza-naphthacen-1-one is substituted in the 5, 8, 9 and/or the 12 positions; the 3-amino-9-dodecyl-2,9-dihydro-2,4,9-triaza-fluoren-1-one is substituted in the 6, 7 and/or the 9 positions; the 3-amino-11-dodecyl-2,11-dihydro-2,4,11-triaza-benzo[b]fluoren-1-one is substituted in the 7, 8 and/or in the 11 position; the 3-amino-13-dodecyl-2,13-dihydro-2,4,13-triaza-indeno[1,2-b]anthracen-1-one is substituted in the 8, 9 and/or in the 13 positions; the 3,7-diamino-9,10-didodecyl-2,6-diaza-anthracene-1,5-dione is substituted in the 9 and/or in the 10 positions; the 3,10-diamino-5,12-didodecyl-5,12-dihydro-2,5,7,9,12,14-hexaaza-pentacene-1,8-dione is substituted in the 5 and/or in the 12 positions; the 4-dodecyl-4H-benzo[f]quinazoline-1,3-dione is substituted in the 4, 7, 8 and/or 9 positions; the 5-dodecyl-5H-pyrido[4,3-b]indole-1,3-diamine is substituted in the 5, 7 and/or 8 positions; the 5-dodecyl-5H-benzo[f]pyrido[4,3-b]indole-1,3-diamine is substituted in the 5, 8 and/or 9 positions; the 5,10-dodecyl-pyrimido[4,5-g]quinazoline-2,4,7,9-tetraone is substituted in the 5 and/or 10 positions; the 7-amino-1-dodecyl-1H-[1,6]naphthyridin-5-one is substituted in the 1, 2, 3 and/or 4 positions; the 7-octyl-7H-pyrrolo[2,3-d]pyrimidin-4-ylamine is substituted in the 4, 5 and/or the 7 positions; the 7,14-didodecyl-7,14-dihydro-1,3,5,7,8,10,12,14-octaaza-pentacene-2,4,9,11-tetraone is substituted in the 1, 7, 8 and/or the 14 positions; the 8-dodecyl-8H-pteridine-2,4-dione is substituted in the 5, 6, 7 and/or 8 positions; the 9-dodecyl-9H-1,3,9-triaza-fluoren-4-ylamine is substituted in the 6, 7 and/or 9 positions; the 8,9-dimethyl-12-dodecyl-12H-1,3,5,12-tetraaza-naphthacene-2,4-dione is substituted in the 5, 8 and 9 positions; the 11-dodecyl-9H-1,3,11-triaza-benzo[b]fluoren-4-ylamine is substituted in the 7, 8 and 11 positions; the 12-dodecyl-12H-1,3,5,12-tetraaza-naphthacene is substituted in the 12 position; and the 14-dodecyl-4H-1,3,5,12-tetraaza-pentacene-2,4-dione is substituted in the 14 position.

52. The composite of claim 49, where one molecular aromatic species from amongst 2-amino-5-dodecyl-3,5-dihydro-pyrrolo[3,2-d]pyrimidin-4-one, 3-amino-9-dodecyl-2,9-dihydro-2,4,9-triaza-fluoren-1-one, 3-amino-11-dodecyl-2,11-dihydro-2,4,11-triaza-benzo[b]fluoren-1-one, or 3-amino-13-dodecyl-2,13-dihydro-2,4,13-triaza-indeno[1,2-b]anthracen-1-one, and their respective derivatives and the other molecular aromatic species from amongst 7-amino-1-dodecyl-1H-[1,6]naphthyridin-5-one, 3-amino-5-dodecyl-5H-benzo[b][1,6]naphthyridin-1-one, 3-amino-5-dodecyl-5H-2,5-diaza-naphthacen-1-one, or 3-amino-5-dodecyl-5H-2,5-diaza-pentacen-1-one, and their respective derivatives can interact to form the helical around a carbon nanotube.

53. The composite of claim 49, where one molecular aromatic species that forms the helix is a flavin mononucleotide or d-ribityl alloxazine, while the other is selected from amongst 1-dodecyl-1H-pyrrolo[3,2-c]pyridine-4,6-diamine, 1-dodecyl-1H-benzo[h]quinazoline-2,4-dione, 2-amino-5-dodecyl-3,5-dihydro-pyrrolo[3,2-d]pyrimidin-4-one, 3-amino-5-dodecyl-5H-benzo[b][1,6]naphthyridin-1-one, 3-amino-5-dodecyl-5H-2,5-diaza-naphthacen-1-one, 3-amino-9-dodecyl-2,9-dihydro-2,4,9-triaza-fluoren-1-one, 3-amino-11-dodecyl-2,1,1-dihydro-2,4,1,1-triaza-benzo[b]fluoren-1-one, 3-amino-13-dodecyl-2,13-dihydro-2,4,13-triaza-indeno[1,2-b]anthracen-1-one, 3,7-diamino-9,10-didodecyl-2,6-diaza-anthracene-1,5-dione, 3,10-diamino-5,12-didodecyl-5,12-dihydro-2,5,7,9,12,14-hexaaza-pentacene-1,8-dione, 4-dodecyl-4H-benzo[f]quinazoline-1,3-dione, 5-dodecyl-5H-pyrido[4,3-b]indole-1,3-diamine, 5-dodecyl-5H-benzo[f]pyrido[4,3-b]indole-1,3-diamine, 5,10-dodecyl-pyrimido[4,5-g]quinazoline-2,4,7,9-tetraone, 7-amino-1-dodecyl-1H-[1,6]naphthyridin-5-one, 7-octyl-7H-pyrrolo[2,3-d]pyrimidin-4-ylamine, 7,14-didodecyl-7,14-dihydro-1,3,5,7,8,10,12,14-octaaza-pentacene-2,4,9,11-tetraone, 8-dodecyl-8H-pteridine-2,4-dione, 9-dodecyl-9H-1,3,9-triaza-fluoren-4-ylamine, 8,9-dimethyl-12-dodecyl-12H-1,3,5,12-tetraaza-naphthacene-2,4-dione, 11-dodecyl-9H-1,3,11-triaza-benzo[b]fluoren-4-ylamine, 12-dodecyl-12H-1,3,5,12-tetraaza-naphthacene and 14-dodecyl-4H-1,3,5,12-tetraaza-pentacene-2,4-dione, and their respective derivatives.

54. The composite of claim 49, where one molecular aromatic species that forms the helix is a flavin mononucleotide or d-ribityl alloxazine, while the other is selected from amongst 1-dodecyl-1H-pyrrolo[3,2-c]pyridine-4,6-diamine, 5-dodecyl-5H-pyrido[4,3-b]indole-1,3-diamine, 5-dodecyl-5H-benzo[f]pyrido[4,3-b]indole-1,3-diamine, 8-dodecyl-8H-pteridine-2,4-dione, 7-octyl-7H-pyrrolo[2,3-d]pyrimidin-4-ylamine, 9-dodecyl-9H-1,3,9-triaza-fluoren-4-ylamine, 11-dodecyl-9H-1,3,11-triaza-benzo[b]fluoren-4-ylamine, or 13-dodecyl-13H-1,3,13-triaza-indeno[1,2-b]anthracen-4-ylamine and their respective derivatives.

55. An article derived from the composite of claim 38.

* * * * *